(12) United States Patent
Casey et al.

(10) Patent No.: US 11,980,379 B2
(45) Date of Patent: May 14, 2024

(54) CLOT RETRIEVAL SYSTEM FOR REMOVING OCCLUSIVE CLOT FROM A BLOOD VESSEL

(71) Applicant: NEURAVI LIMITED, Galway (IE)

(72) Inventors: Brendan Casey, Barna (IE); David Vale, Barna (IE); Maeve Holian, Galway (IE); David Hardiman, Dublin (IE); Grainne O'Connor, Galway (IE)

(73) Assignee: NEURAVI LIMITED, Galway (IE)

( * ) Notice: Subject to any disclaimer, the term of this patent is extended or adjusted under 35 U.S.C. 154(b) by 80 days.

(21) Appl. No.: 17/566,003

(22) Filed: Dec. 30, 2021

(65) Prior Publication Data
US 2022/0117615 A1    Apr. 21, 2022

Related U.S. Application Data

(63) Continuation of application No. 16/021,505, filed on Jun. 28, 2018, now Pat. No. 11,253,278, which is a
(Continued)

(51) Int. Cl.
*A61B 17/22*    (2006.01)
*A61B 17/221*    (2006.01)
(Continued)

(52) U.S. Cl.
CPC ...... *A61B 17/22031* (2013.01); *A61B 17/221* (2013.01); *A61B 2017/00477* (2013.01);
(Continued)

(58) Field of Classification Search
CPC ............ A61B 17/22031; A61B 17/221; A61B 17/12109; A61B 2017/2215
See application file for complete search history.

(56) References Cited

U.S. PATENT DOCUMENTS

| 4,455,717 A | 6/1984 | Gray |
| 4,611,594 A | 9/1986 | Grayhack et al. |

(Continued)

FOREIGN PATENT DOCUMENTS

| CN | 2557083 Y | 6/2003 |
| CN | 101172051 A | 5/2008 |

(Continued)

OTHER PUBLICATIONS

Extended European Search Report issued in European Patent Application No. 22 20 0792 dated Dec. 21, 2022.
U.S. Pat. No. 6,348,062 A, Jul. 8, 2003, Hopkins, et al.

*Primary Examiner* — Alexander J Orkin
(74) *Attorney, Agent, or Firm* — TROUTMAN PEPPER HAMILTON SANDERS LLP

(57) ABSTRACT

A clot removal device for removing clot from a body vessel comprising an expandable structure and an elongate member. The elongate member can have a proximal end and a distal end, the elongate member being connected to the expandable structure at its distal end. The expandable structure can have a constrained delivery configuration, an expanded clot engaging deployed configuration, and an at least partially constrained clot pinching configuration. At least a portion of the expandable structure can be configured to engage clot in the expanded deployed configuration and to pinch clot on movement from the deployed configuration to the clot pinching configuration.

18 Claims, 53 Drawing Sheets

Related U.S. Application Data continuation-in-part of application No. 15/359,943, filed on Nov. 23, 2016, now Pat. No. 10,617,435, which is a continuation-in-part of application No. 14/952,202, filed on Nov. 25, 2015, now Pat. No. 10,363,054.

(60) Provisional application No. 62/526,005, filed on Jun. 28, 2017, provisional application No. 62/342,012, filed on May 26, 2016, provisional application No. 62/259,976, filed on Nov. 25, 2015, provisional application No. 62/084,960, filed on Nov. 26, 2014.

(51) Int. Cl.
　　A61B 17/00　　　(2006.01)
　　A61B 17/12　　　(2006.01)
　　A61B 90/00　　　(2016.01)

(52) U.S. Cl.
　　CPC .......... A61B 2017/00526 (2013.01); A61B 2017/00778 (2013.01); A61B 17/12109 (2013.01); A61B 2017/22034 (2013.01); A61B 2017/2212 (2013.01); A61B 2017/2215 (2013.01); A61B 2090/3966 (2016.02)

(56) References Cited

U.S. PATENT DOCUMENTS

| | | |
|---|---|---|
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | MacGregor et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |

(56) References Cited

U.S. PATENT DOCUMENTS

| | | |
|---|---|---|
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 3,021,380 A1 | 9/2011 | Thompson et al. |
| 8,021,379 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |

(56) References Cited

U.S. PATENT DOCUMENTS

| | | |
|---|---|---|
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Am et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1 | 11/2001 | Daniel et al. |

(56) References Cited

U.S. PATENT DOCUMENTS

| | | |
|---|---|---|
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavlovic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0069520 A1 | 4/2003 | Skujins et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0209678 A1* | 9/2005 | Henkes .............. A61F 2/91 623/1.2 |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |

(56) References Cited

U.S. PATENT DOCUMENTS

| | | |
|---|---|---|
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0022572 A1 | 1/2012 | Braun et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |

(56) References Cited

U.S. PATENT DOCUMENTS

| | | |
|---|---|---|
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |

(56) References Cited

U.S. PATENT DOCUMENTS

| | | |
|---|---|---|
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | 2008/135823 A1 | 11/2008 |
| WO | 2009/031338 A1 | 3/2009 |
| WO | 2009/076482 A1 | 6/2009 |
| WO | 2009/086482 A1 | 7/2009 |
| WO | 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/090472 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

* cited by examiner

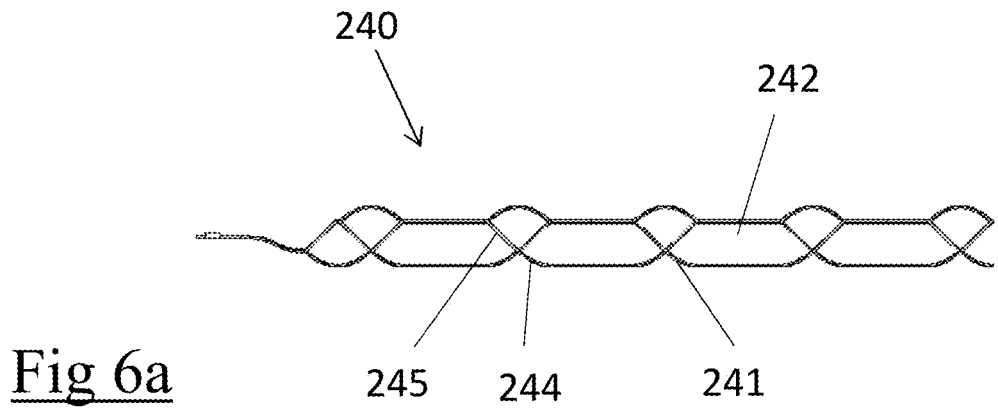
Fig 6a
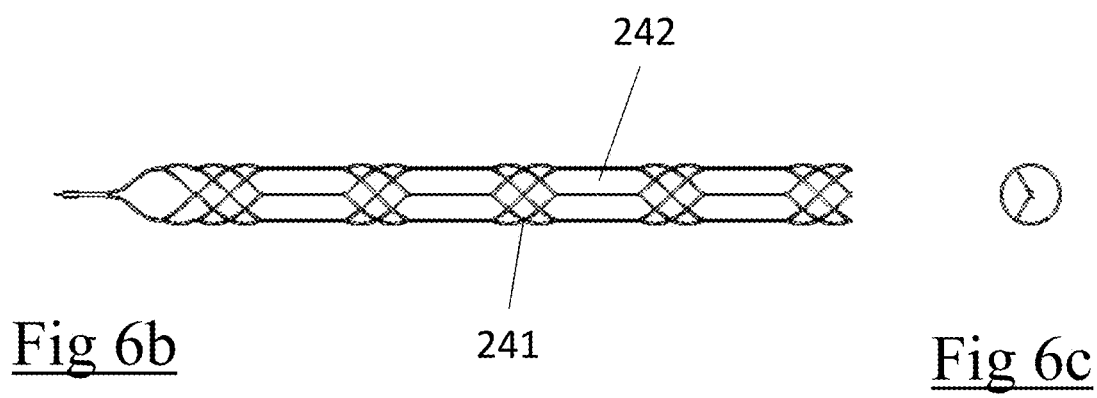
Fig 6b
Fig 6c
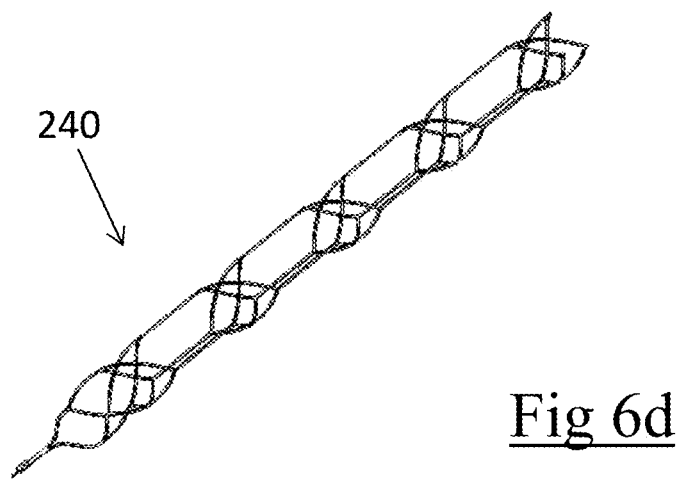
Fig 6d

CLOT RETRIEVAL SYSTEM FOR REMOVING OCCLUSIVE CLOT FROM A BLOOD VESSEL

CROSS REFERENCE TO RELATED APPLICATIONS

This application is a continuation of U.S. patent application Ser. No. 16/021,505 filed Jun. 28, 2018, which claims priority to U.S. Provisional Application No. 62/526,005 filed Jun. 28, 2017.

U.S. patent application Ser. No. 16/021,505 filed Jun. 28, 2018 is also a continuation-in-part of U.S. patent application Ser. No. 15/359,943, filed Nov. 23, 2016, now U.S. Pat. No. 10,617,435 issued Apr. 14, 2020, which claims priority to U.S. Provisional Patent Application No. 62/342,012 filed May 26, 2016 and claims priority to U.S. Provisional Patent Application No. 62/259,976 filed Nov. 25, 2015.

U.S. patent application Ser. No. 15/359,943, filed Nov. 23, 2016, now U.S. Pat. No. 10,617,435 issued Apr. 14, 2020, is a continuation-in-part of U.S. patent application Ser. No. 14/952,202 filed Nov. 25, 2015, now U.S. Pat. No. 10,363,054 issued Jul. 30, 2019, and U.S. patent application Ser. No. 16/446,749, filed Jun. 20, 2019, each of which claims priority to U.S. Provisional Patent Application No. 62/084,960 filed Nov. 26, 2014.

The contents of each application are incorporated herein by reference in their entirety as if set forth verbatim.

FIELD

This invention relates to devices intended for removing acute blockages from blood vessels. Acute obstructions may include clots, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clots from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

SUMMARY

According to the invention there is provided a clot removal device for removing a clot from a body vessel comprising an expandable structure and an elongate member, the elongate member having a proximal end and a distal end, the elongate member being connected to the expandable structure at its distal end, the expandable structure having a constrained delivery configuration, an expanded clot engaging deployed configuration, and an at least partially constrained clot pinching configuration, at least a portion of the expandable structure being configured to engage clot in the expanded deployed configuration and to pinch the clot on movement from the deployed configuration to the clot pinching configuration.

In one case the expandable structure comprises a clot pinching structure which is configured to pinch a clot on movement from the deployed configuration to the clot pinching configuration.

In one embodiment the expandable structure comprises a main body portion and a clot pinching structure and wherein a diameter of the clot pinching structure is less than a diameter of the main body portion. The clot pinching structure may be located at a proximal end of the expandable structure.

In one case the clot pinching structure is substantially tubular. The clot pinching structure may be of spiral form. The spiral may extend for 360° and may have an outer diameter of about 5 mm and a spiral pitch of about 14 mm.

In some cases, a longitudinal centre axis of the distal barrel section is offset from a centre line of the spiral or may be at an angle to the centre line of the spiral.

In one embodiment the clot pinching structure comprises a plurality of clot-receiving cells, a cell comprising struts extending between crowns, the struts being configured to pinch a clot located in the cell as the device is moved from the expanded deployed configuration to the at least partially constrained clot pinching configuration.

In one case adjacent struts define a channel which narrows distally towards the crown joining the struts.

Adjacent struts may define a necked region there between which is configured to close as the device is moved to the clot pinching configuration.

In one embodiment the crowns of adjacent cells are offset along the longitudinal axis of the device. Adjacent struts may be of differing lengths.

In one case the cell has a proximally facing crown and a distally facing crown and wherein the proximally facing crown has a diameter which is larger than a diameter of the distally facing crown.

In one embodiment the size of a clot-receiving cell towards a proximal end of the clot pinching structure is smaller than a cell towards a distal end of the clot pinching structure.

In some cases, adjacent struts comprise at least one bend or undulation, the bends are configured so that the bends in adjacent struts inter engage as the device is moved to the clot pinching configuration. The strut may comprise a plurality of bends along the length thereof.

The bends may be located towards a distal end of the strut.

In some embodiments the expandable structure is of a shape memory material such as Nitinol.

In some cases, the ratio of a diameter of the main body portion to a diameter of the clot pinching structure is from 1.5:1 to 4:1, in some cases from 2:1 to 3:1. In one case the diameter of the main body portion is about 4.5 mm or 5 mm and the diameter of the clot pinching structure is about 2 mm.

The device may comprise a radiopaque marker at a transition between the main body portion and the clot pinching structure.

A longitudinal axis of the main body portion may be co-linear with a longitudinal axis of the clot pinching structure.

In some cases, a longitudinal axis of the clot pinching structure is offset from a longitudinal axis of the main body portion.

In one embodiment the device has a longitudinal axis which extends through the main body portion and the clot pinching structure extends around the longitudinal axis in a spiral.

According to the invention there is also provided a clot removal device for removing organised clot from a body vessel the device comprising an expandable tubular structure and an elongate member, the elongate member comprising a proximal end and a distal end, the expandable tubular structure comprising a network of interconnected struts, said network configured to engage with a clot in an expanded state, the network configured such that in the expanded state at least a portion of the network interpenetrates the clot, the network further configured such that when the network is collapsed from a state of interpenetration with the clot that at least a portion of the network pinches at least a portion of the clot.

Also provided is a device as described above wherein the elongate member is configured to retract the network with the network both interpenetrating the clot and at least a portion of the network effecting a pinch on at least a portion of the clot.

According to the invention there is also provided a clot removal device for removing an organised clot from a body vessel, the device comprising an expandable tubular structure and an elongate member, the elongate member comprising a proximal end and a distal end and the elongate member connected to the tubular structure at its distal end, the expandable tubular structure configured to interpenetrate the organised clot when deployed into contact with the organised clot, the expandable tubular structure further comprising a plurality of first and second strut members interconnected at only one end, each pair of struts comprising a spring element biased to an expanded configuration and at least one first spring element comprising a soft spring element and at least one second spring element comprising a firm spring element such that the collapse of the tubular structure is asymmetric the asymmetric collapse of the structure effecting a pinch on a portion of the organised clot that is in interpenetration with at least a portion of the first spring element.

According to the invention there is also provided a clot removal device for removing a clot from a body vessel the device comprising an expandable structure and an elongate member, the elongate member comprising a proximal end and a distal end and the elongate member connected to the expandable structure at its distal end, the expandable structure comprising at least a first cell and at least one second cell each of said first and second cells comprising a collapsed delivery configuration and a deployed expanded configuration and in the expanded configuration each cell further comprising an orifice, the expandable structure configured to interpenetrate the clot, said interpenetration of the clot comprising the extrusion of at least a portion of the clot through at least one of said first cells, such that the orifice of at least some of the cells is configured to allow at least a portion of the clot body to interpenetrate the structure.

According to the invention there is also provided a clot retrieval device for removing an occlusive clot from a blood vessel comprising a clot engaging element, the clot engaging element having a constrained delivery configuration and an expanded deployed configuration, the clot engaging element being configured to exert an outward radial force when deployed within a lumen whose inner diameter is lower than that of the expanded deployed configuration, said outward radial force varying in a generally sinusoidal pattern along the length of the clot engaging element.

Also provided is a clot retrieval device as described above wherein the generally sinusoidal pattern comprises a wave pattern, and the amplitude of the wave pattern is generally consistent along the length of the device.

Also provided is a clot retrieval device as described above wherein the generally sinusoidal pattern comprises a wave pattern, and the amplitude of the wave pattern decreases along the length of the device, being higher at the proximal end and lower at the distal end of the device.

Also provided is a clot retrieval device as described above in which the clot engaging element comprises a plurality of adjacent segments, and the radial force of at least two adjacent segments differs from each other.

Also provided is a clot retrieval device as described anywhere above comprising a distal clot fragment protection section. Alternatively, or additionally a distal fragment protector is provided which may be mounted on a separate shaft extending through the device In some embodiments the distal end of the elongate member is connected to the proximal end of the expandable structure. There may be a proximal joint between the elongate member and the expandable structure. The proximal joint may comprise a step at the distal end of the elongate member. In one case the proximal joint comprises a locking collar for engagement with the elongate member and a proximal end of the expandable structure.

In one case the proximal end of the expandable structure comprises a recess or slot which is configured for engagement with the step at the distal end of the elongate member.

In one case the expandable structure comprises two or more legs which are configured for location partially around the step.

In some embodiments a longitudinal axis of the elongate member is radially offset from a longitudinal axis of the collar.

There may be a bond such as an adhesive bond or weld between the collar and the elongate member and between the collar and the proximal end of the expandable structure.

In some cases, the device comprises a radiopaque marker at the distal end of the expandable structure.

There may be two or more radiopaque markers at the distal end of the expandable structure, wherein the radiopaque markers are longitudinally offset from one another.

In some cases, the expandable structure comprises a distal main body portion and a proximal clot pinching structure and the device comprises two or more radiopaque markers at a transition between the main body portion and the clot pinching structure. The radiopaque markers at the transition are longitudinally offset from one another.

According to the invention there is provided a method of removing an occlusive clot from a blood vessel comprising the steps of: providing a clot retrieval device having a clot engaging section, the device having a constrained delivery configuration and an expanded deployed configuration; advancing a microcatheter across an occlusive clot; loading the device into the microcatheter and advancing to a distal portion of the microcatheter; retracting the microcatheter to deploy the device and engage the clot engaging section with the clot; re-advancing the microcatheter to re-sheath at least a portion of the clot engaging section; and retrieving at least a portion of the device and the captured clot into a retrieval catheter.

Also provided are additional variants of this method, including: a method as described above in which the retrieval catheter is an intermediate catheter; a method as described above in which the retrieval catheter is a balloon guide catheter, or a guide catheter, or a sheath; a method as described above wherein the act of re-sheathing a portion of the clot engaging section causes a portion of the clot to be pinched within a cell of the clot engaging section; a method as described above wherein the clot retrieval device is configured to pinch at least a portion of the clot; a method as described above comprising pulling the device proximally after deployment of the device within the clot; a method as described above comprising delaying pushing of the device distally after deployment to further embed in the clot prior to re-sheathing; a method as described above comprising pulling the device proximally into a larger vessel before retrieval into a retrieval catheter.

A further method is provided comprising a method of dislodging and removing an occlusive clot from a blood vessel segment comprising the steps of: providing a clot retrieval device wherein the clot retrieval device comprises a monolithic tubular structure and an elongate member, the monolithic tubular structure located at the distal end of the elongate member, the monolithic tubular structure having a most constrained delivery configuration, a partially collapsed pinching configuration and a clot engaging deployed configuration; engaging the occlusive clot with the monolithic tubular structure by expanding the monolithic tubular structure from its most constrained delivery configuration to its clot engaging deployed configuration with the elongate member extending through a proximal portion of the vessel segment and exterior of the patient, partially collapsing the monolithic tubular structure from the clot engaging deployed configuration to the partially collapsed pinching configuration to effect a pinch on at least a portion of the occlusive clot, restraining the monolithic tubular structure in the partially collapsed pinching configuration, dislodging the clot from the site of occlusion and removing it from the vessel segment by retracting the monolithic tubular structure while maintaining the restraint.

Also provided is a method of treating a patient with an occluded vessel, the occlusion comprising an organised clot, the method comprising the steps of:—providing a clot retrieval device and a removal catheter, wherein the clot retrieval device comprises an expandable element and an elongate member, the expandable element located at the distal end of the elongate member, the expandable element having a fully collapsed delivery configuration, a fully expanded deployed configuration and the expandable element comprising a clot pinching substructure, the clot pinching substructure configured to pinch at least a portion of the clot body as the expandable element is at least partially collapsed from the fully expanded configuration, the removal catheter comprising a collar at its distal end, delivering the clot retrieval device to the occluded vessel through a micro catheter in its collapsed configuration, deploying the expandable element into contact with at least a portion of the clot, while maintaining the position of the elongate member steadfast, advancing along the elongate member the removal catheter, engaging the collar of the removal catheter with the expandable element and effecting the pinching substructure so as to pinch at least a portion of the organised clot, withdrawing in unison from the vessel the removal catheter and the clot retrieval device, while maintaining engagement between the collar and the expandable element, and removing the clot retrieval device, the removal catheter and the pinched occlusive clot from the patient.

In some embodiments, the act of retrieving at least a portion of the device and captured clot into a retrieval catheter includes the step of aspirating through the retrieval catheter.

In some cases, the act of re-sheathing a portion of the clot engaging section causes a portion of the clot to be pinched within a cell of the clot engaging section.

In some embodiments, the method comprises pulling the device proximally after deployment of the device within the clot.

In some cases, the method comprises delaying pushing of the device distally after deployment to further embed in the clot prior to re-sheathing.

In some embodiments the method comprises pulling the device proximally into a larger vessel before retrieval into a retrieval catheter.

BRIEF DESCRIPTION OF THE DRAWINGS

The invention will be more clearly understood from the following description of some embodiments thereof, given by way of example only, with reference to the accompanying drawings, in which:

FIG. 3c illustrates force profile of three devices similar to the device of FIG. 3a;

FIGS. 6a to 6d are a series of views of another embodiment of the invention;

FIGS. 38 to 44(c) illustrate various strut patterns of the devices;

FIG. 43 is an illustration of the profile and the outer shape of a device according to the invention;

FIGS. 44a to c illustrate a strut/crown configuration which promotes clot pinching;

DETAILED DESCRIPTION

Figure 1A:
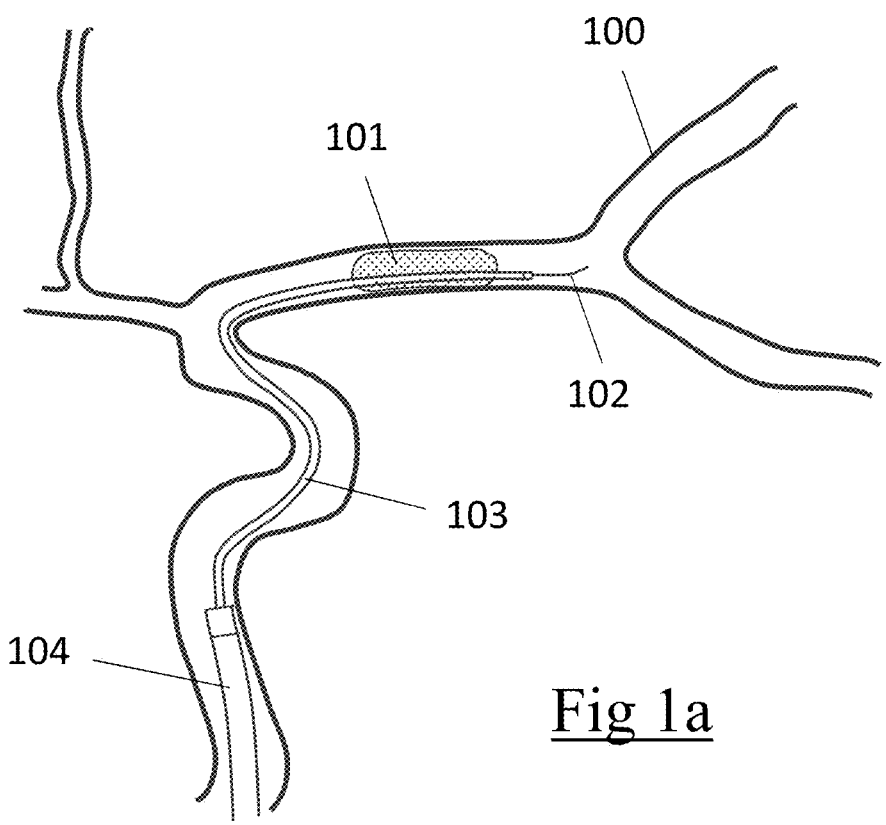
FIGS. 1a to 1e show the method of use of a clot retrieval device of the invention.

Specific embodiments of the present invention are now described in detail with reference to the Figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

The expandable members of the designs disclosed are desirably made from a material capable of recovering its shape automatically once released from a highly strained delivery configuration. A superelastic material such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a huge range of shapes as disclosed herein and may be rendered visible under fluoroscopy through the addition of alloying elements (such as Platinum for example) or through a variety of other coatings or marker bands.

Compression of the clot can alter the clot properties and make the clot less amenable to retrieval by making it firmer and "stickier" as described in our WO2012/120490A, the entire contents of which are herein incorporated by reference. The device of this invention is intended to facilitate clot retrieval by expanding between the clot and the vessel wall in such a way as to engage with the clot over a significant surface area and do so with minimal compression of the clot. The overall clot compression is minimised because the device is constructed to have rings of high compression with deep strut embedding interspersed with areas of minimal clot compression. A portion of the clot can protrude into the area of low compression and can be pinched between the tip of a catheter and the nitinol struts of the device. The pinch is achieved by forwarding a microcatheter or intermediate catheter over the device until a portion of the clot is compressed between the tip of the catheter and a crown or strut on the device. This pinch facilitates removal of the clot as it increases the grip of the device on the clot, particularly fibrin rich clots. It may also elongate the clot reducing the dislodgement force by pulling the clot away from the vessel wall during the dislodgement process. It potentially improves retention of the clot during retraction to the access guide catheter or sheath by controlling the proximal end of the clot and preventing it from snagging on a side branch vessel.

The device design to facilitate pinching of an occlusive clot detailed in this invention can be incorporated into the full length of the device or more typically in the proximal 30%-50% of the length of the device. The diameter of this pinch segment can vary from 30% to 150% of the diameter of the target vessel at the position of the occlusive clot, but in the preferred embodiment for the middle cerebral artery, it is more typically 50% to 100% of the target vessel diameter. This invention details how the clot pinch can be generated between the microcatheter tip and struts or crowns on a single tubular structure, or alternatively the clot can be pinched between the catheter tip and the struts on the outer cage or inner channel of an assembly.

The inner channel of the invention may also comprise a portion that compresses an area of the clot in order to form a blood communication channel across the clot. Such a channel serves two key purposes: 1) it reduces the pressure gradient across the clot, thus reducing one of the forces that must be overcome in order to retract the clot and 2) it provides a flow path for oxygenated, nutrient carrying blood to reach the ischaemic area distal of the clot.

All of the devices described herein may also comprise a distal fragment capture portion, such as illustrated in FIGS. 7, 8, 9, 10, 11, and 12. This portion is ideally deployed distal of the clot to prevent the distal migration of any clot fragments that might be liberated during retrieval.

Figure 1B:
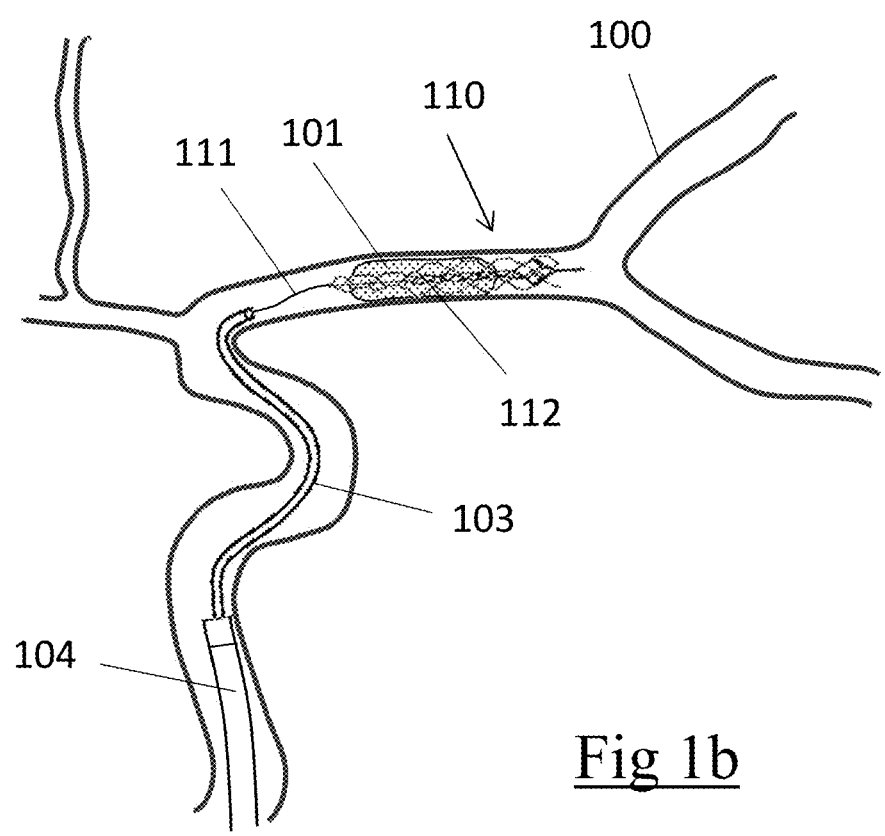
Figure 1C:
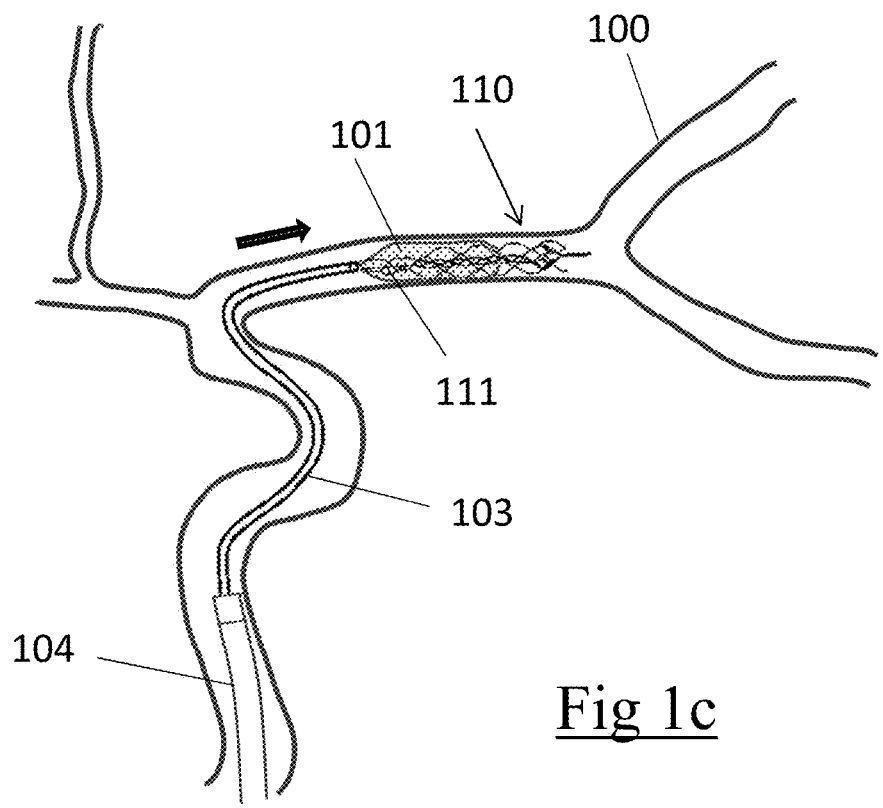
Figure 1D:
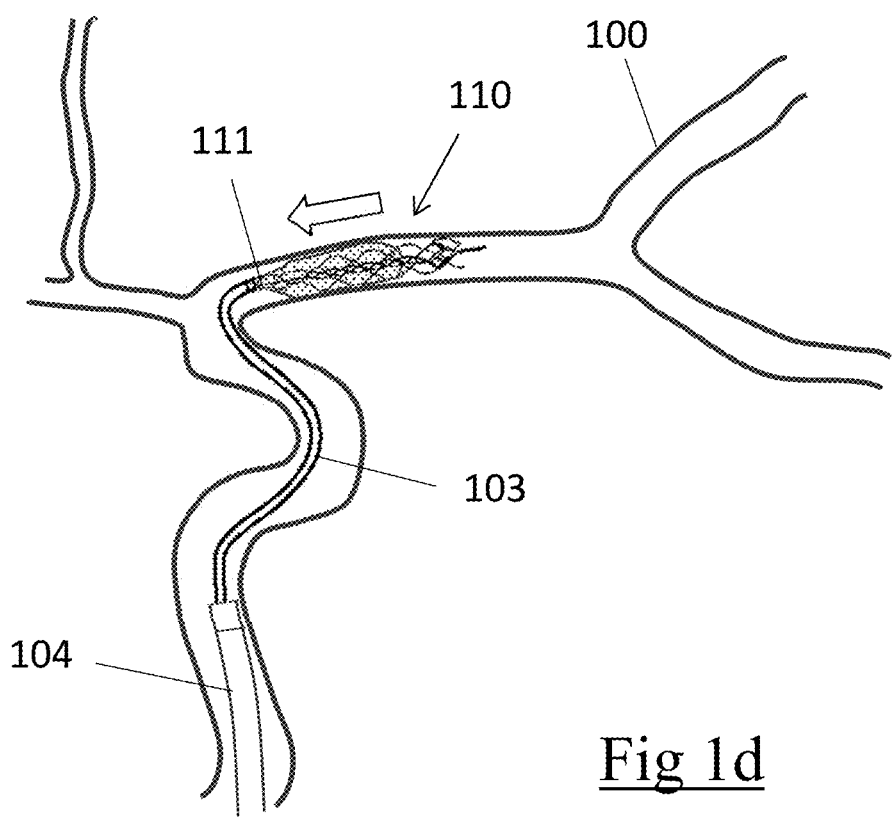

FIGS. 1a-1e show a method of use of a device of this invention. A guidewire 102 and microcatheter 103 are inserted in the vasculature 100 and are advanced across the obstructive clot 101 using conventionally known techniques. When the microcatheter 103 is positioned distal to the occlusive clot 101, the guidewire 102 is removed from the vasculature 100 to allow the clot retrieval device 110 be advanced through the microcatheter. The device 110 is advanced in a collapsed configuration until the distal tip of the device reaches the distal end of the microcatheter 103. The microcatheter is retracted while the position of device 110 is maintained to deploy the clot retrieval device across the clot 101 in a manner that the distal end of the device is preferably positioned distal of the clot 101 (FIG. 1b). The device 110 consists of a clot engagement portion 112 connected to an elongated proximal shaft portion 111.

Figure 1E:
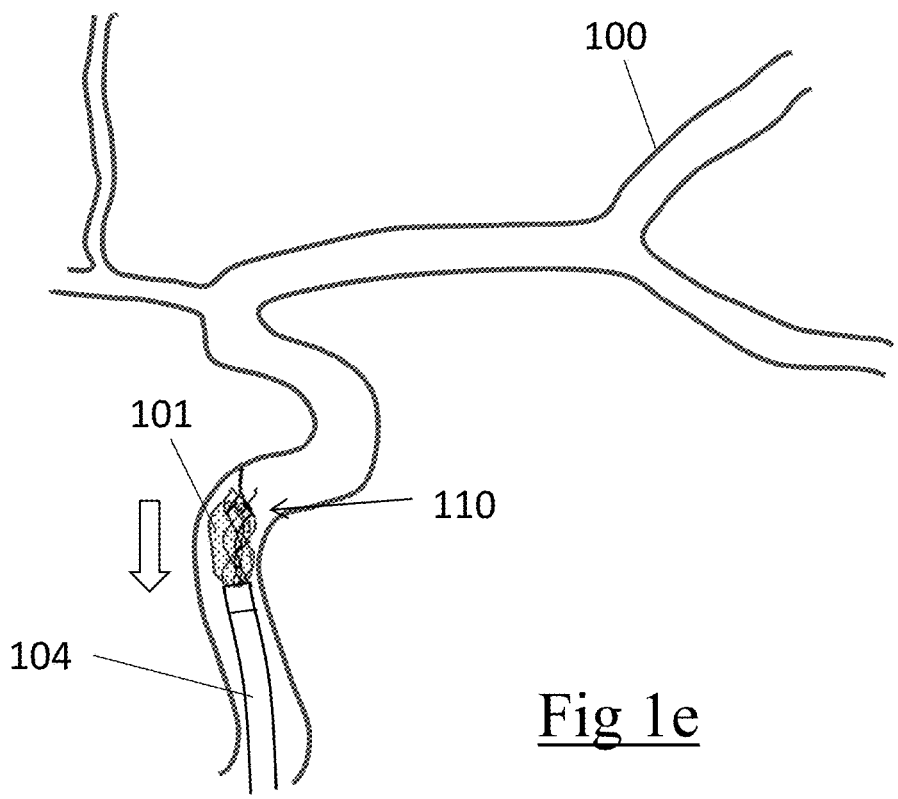

The device 110 expands so that it engages with the occlusive clot at the proximal end or along its length. The device has segments that have low levels of scaffolding and do not compress the clot but allow the clot to protrude into these low radial force areas. The device 110 may be allowed to incubate for a period of time within the clot 101 if desired. Prior to retracting the device, the microcatheter can be forwarded distally to pinch a portion of the clot between the tip of the microcatheter and the struts and crowns of the device adjacent to the low radial force area. This pinch provides additional grip and control of the proximal end of the clot during dislodgement and retention back to the access guide catheter or introducer sheath (FIG. 1e). The relative tension between the device and the microcatheter is maintained by the user during dislodgment and retraction to ensure the pinch on the clot is maintained. While the use of a microcatheter or intermediate catheter to pinch the clot is described as giving additional benefits when used with this invention, all the embodiments described here-in can also be used to dislodge and retrieve clots without the use of catheter pinching if required.

Flow arrest in the vessel may be utilised by inflating a balloon (not shown) on the guide catheter as per standard technique. FIG. 1e illustrates the clot engaged with the device during retrieval into the guide catheter 104. Flow occlusion, aspiration and other standard techniques may be used during the clot retrieval process. The device 110 may be rinsed in saline and gently cleaned before reloading in the insertion tool. The device 110 may be reintroduced into the microcatheter to be redeployed in additional segments of occlusive clot, if required.

Figure 2A:
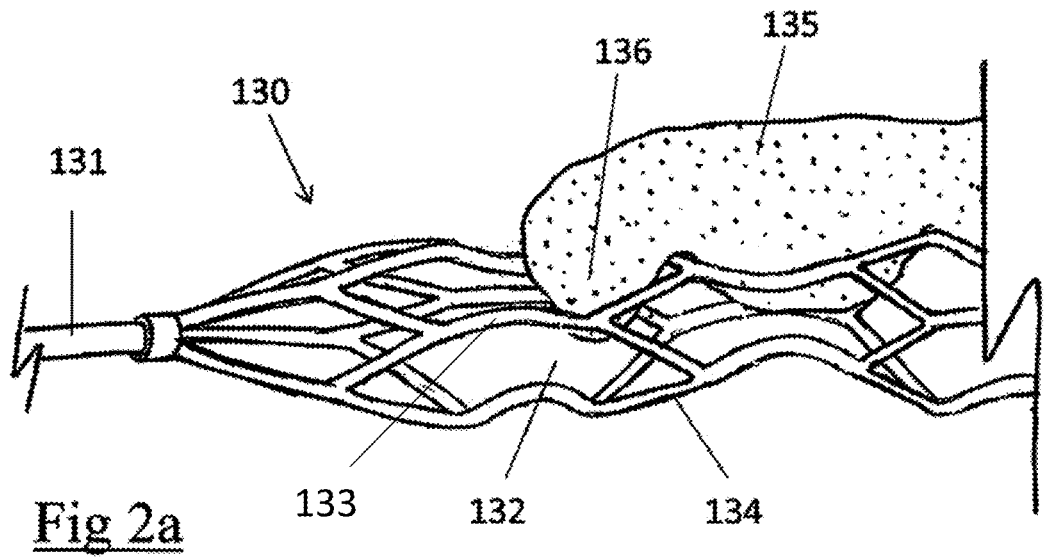
FIGS. 2a to 2c are additional views of the device shown in FIGS. 1a to 1e.
Figure 2B:
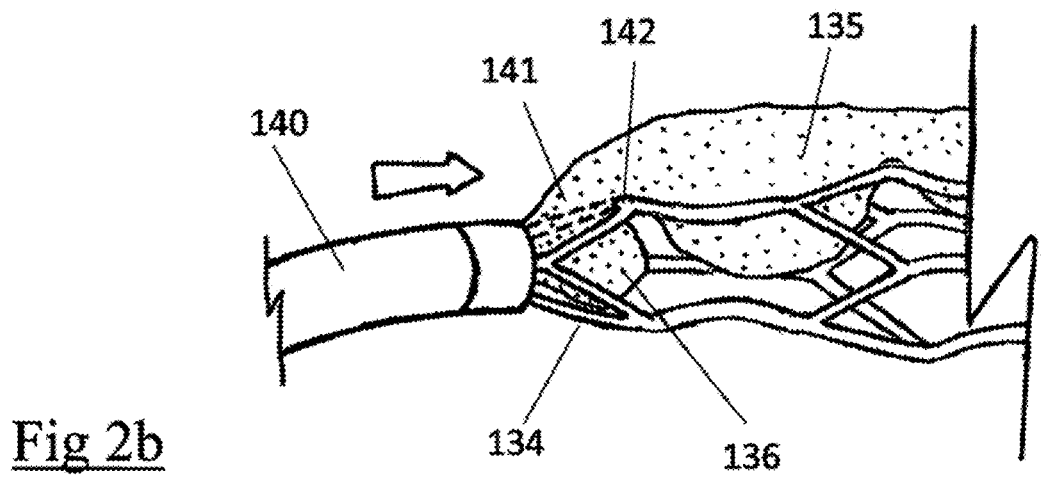
Figure 2C:
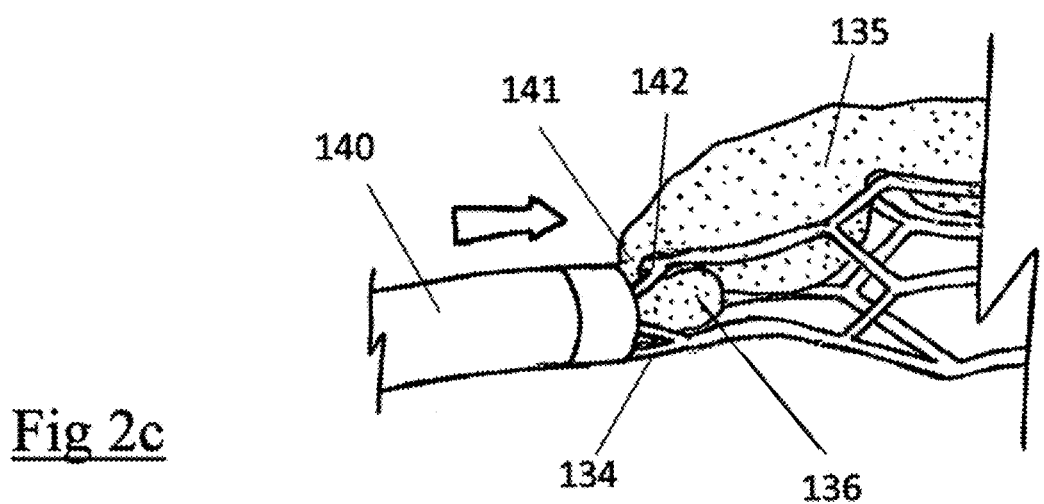

FIGS. 2a-2c show the proximal end of one embodiment of the device illustrated in FIGS. 1a-1e. The device is typically formed from a material with "Superelastic" properties such as nitinol and can be laser cut and expanded from a tube or flat sheet raw material. The self-expanding section of the device 130 is connected to a proximal elongated shaft 131. The device of this invention is designed to create a clot pinch and generate additional grip between the device 130 and the clot 135. The device 130 is constructed so that it consists of rings of struts 134 which have an adequate radial force to provide good clot embedding, interspersed with areas of low scaffolding and low radial force 132. The longitudinal distance between the rings of struts can vary from 2 mm to 8 mm, but in the preferred embodiment for use in the middle cerebral artery the longitudinal spacing is 3-6 mm.

While the struts 134 embed and provide some scaffolding of the clot, the area with low scaffolding 132 allows the clot 136 to protrude into this area. After an incubation time, if desired, of typically 1 to 5 minutes, the microcatheter 140 (used to introduce the device or an alternative microcatheter) can be advanced to pinch the protruding clot 136 between the tip of the microcatheter 144 and the struts and crown 142 of device 130. The struts 134 achieve good embedding in the clot as the freely expanded diameter of these struts can vary from 30% to 150% of the diameter of the target vessel at the position of the occlusive clot, but in the preferred embodiment is 50% to 100% of the target vessel diameter. In the embodiment shown the connecting struts 133 between the rings of struts 134 are curved with a reduced diameter towards the mid-section of the strut to minimise the radial force and scaffolding. This feature can also be seen in FIGS. 3a and 3b.

Further distal advancement of the microcatheter 140 relative to the device 130 will further compress the clot 141 between the catheter tip 144 and the struts of the device 142 increasing the pinch on the clot (FIG. 2c) and the security of the trapped clot segment 136. The user may feel this pinch as a resistance and stop advancing the microcatheter, or alternatively the user may advance the microcatheter a fixed distance over the device (for example 30% to 50% of the device length) before retracting the device and microcatheter together. The relative tension between the device 130 and the microcatheter 140 needs to be maintained to ensure the pinch between the device and clot does not deteriorate. By retracting the device 130 and the microcatheter 140 together, the occlusive clot can be dislodged and retracted back into the access guide catheter or introducer sheath and be removed from the patient. This invention is particularly suited to the dislodgement and retraction of clots which have a high fibrin content (typically higher than 40% fibrin content) and other clots which are difficult to dislodge and retrieve with known stent retriever designs and currently may require multiple passes to remove the clot from the vasculature. This invention may also create a clot pinch by advancing an intermediate catheter in the same manner as described here for the microcatheter 140.

Figure 3A:
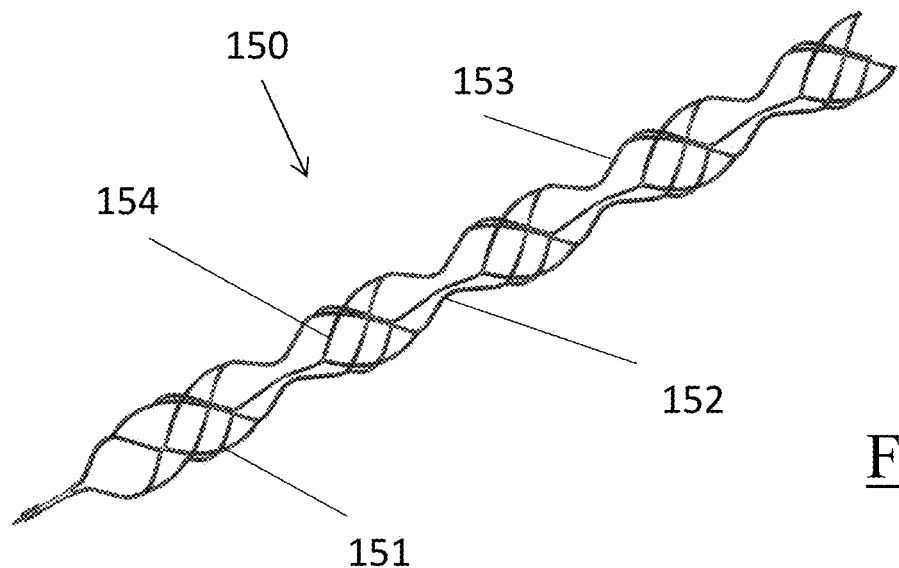
FIGS. 3a to 3b show an isometric view of a device configuration of the invention and a graph of radial force distribution along the length.

FIG. 3a shows an isometric view of another embodiment of the device. In this configuration the embedding section of the device consists of a ring of cells 151. This ring 151 consists of 3 circumferential cells in this embodiment. The number of cells in the circumferential ring can vary from 2 to 5, but in the preferred embodiment is 3 or 4 cells. As with the device shown in FIGS. 2a-2c, the portions of the device 152 between the embedding cells section have low radial force and a low level of scaffolding. The low level of scaffolding is achieved by minimising the potential surface contact area between the device struts and the clot in this area 152. In this embodiment the connecting struts 153 are curved towards the centre-line of the device at the mid-point to further reduce the strut contact force and area with the clot. This low surface contact area and radial force allows the clot to protrude into this section of the device when it is deployed in an occlusive clot. Partial re-sheathing of the device with a microcatheter or intermediate catheter can then pinch this protruding clot between the tip of the catheter and the proximal struts 154 of the embedding ring of cells.

Figure 3B:
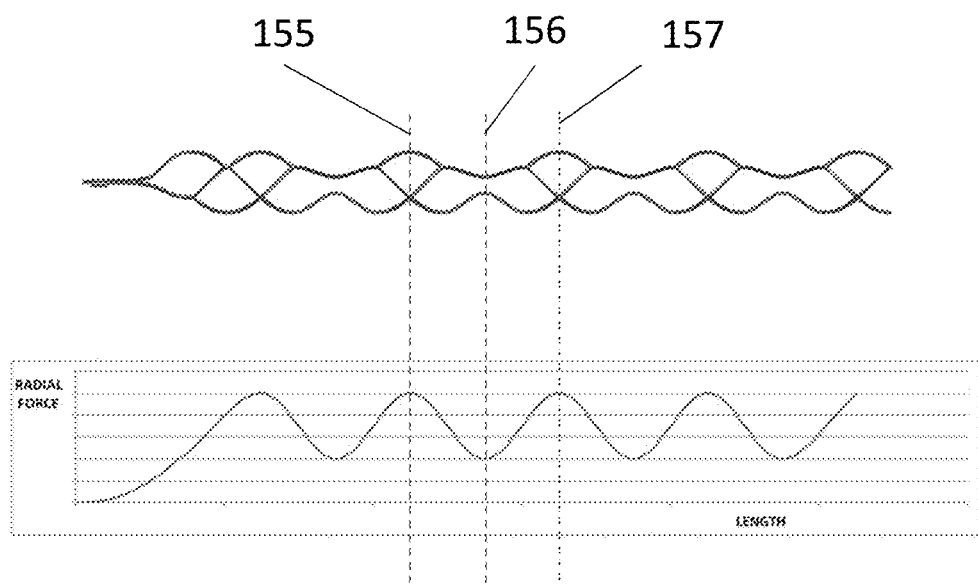

FIG. 3b shows a side view of the device illustrated in FIG. 3a with a corresponding graph of radial force plotted against device length. The dotted lines 155 and 157 show how the rings of cells that embed in the clot have a higher radial force compared with the sections 152 between the rings. Dotted line 156 indicates the reduced radial force of this section.

Figure 3C:
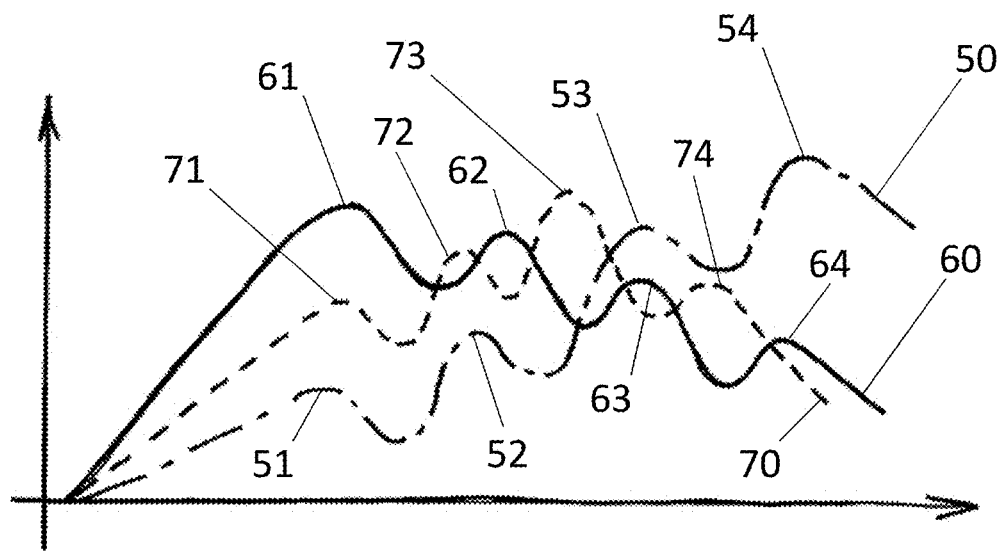

FIG. 3c illustrates the outward radial force profile of three devices of this invention similar to device 150 of FIG. 3a, when constrained in a lumen of less than 50% of their freely expanded diameters. All three exhibit the generally sinusoidal pattern described previously, but the magnitude (or amplitude) of the radial force peaks and troughs varies along the length of these devices. Profile 50 represents a radial force profile that tapers up along the length of the device, with the radial force of the first peak 51 being lower than that of subsequent peaks 52-54. Profile 60 represents a radial force profile that tapers down along the length of the device, with the radial force of the first peak 61 being higher than that of subsequent peaks 62-64. Profile 70 represents a radial force profile that tapers up and then down along the length of the device, with the radial force of the first peak 71 being lower than that of the second peak 72, but the radial force of the last peak 74 being lower than that of the second from last peak 73.

Figure 3D:
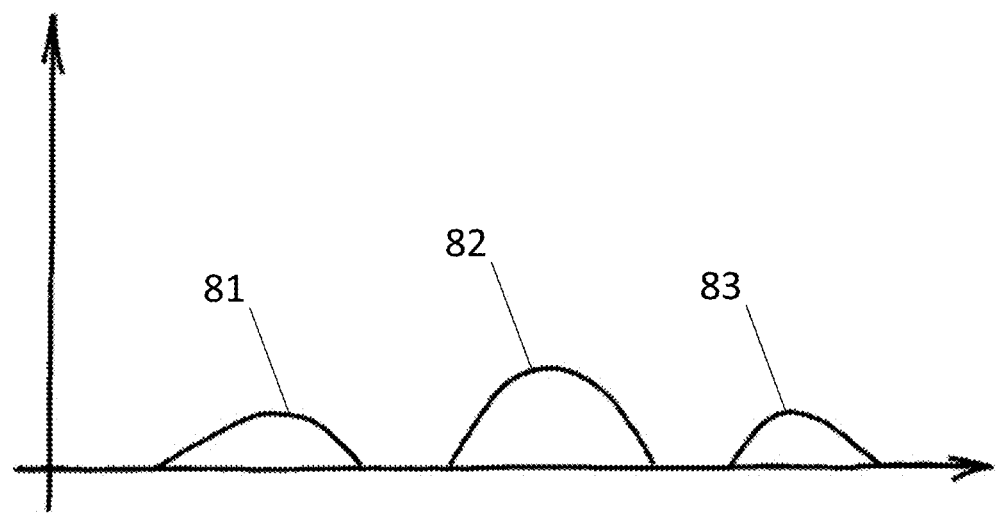
FIG. 3d illustrates an example radial force profile if the device were constrained instead in a lumen in one embodiment.

FIG. 3d illustrates what radial force profile 70 could look like if the device were constrained instead in a lumen of more than 50% of its freely expanded diameter (80% for example). In this case we see that the device exerts no outward radial force whatsoever on its constraining lumen in areas either side of the three peaks 81, 82, 83 shown. Thus, the device is maintaining its grip on the clot in the area of the peaks, while exerting minimal compression on the clot in the areas between the peaks, which helps to minimize the force required to retract the clot, and thus increases the likelihood of a successful clot retrieval.

The FIGS. 3c and 3d also represent the radial pressure of the strut elements of these three different devices. Radial pressure differs from radial force in that it refers to the force per unit area exerted by the device. Thus, if two devices have the same radial force over a given area, and one device has a lower strut surface area than the other in that given area, then the device with the lower strut surface area will exert a higher radial pressure. This is very important for clot grip because radial pressure is what enables a strut to embed itself into the clot material—somewhat akin to the difference between a stiletto heel and an elephant's foot: when standing on soft sand the stiletto heel will sink deeply into the sand while the elephant's foot will not sink as deeply in. For a given level of radial force, the radial pressure of a device can thus be increased by reducing the strut surface area, which can be done by reducing strut width or number of struts.

Figure 7A:
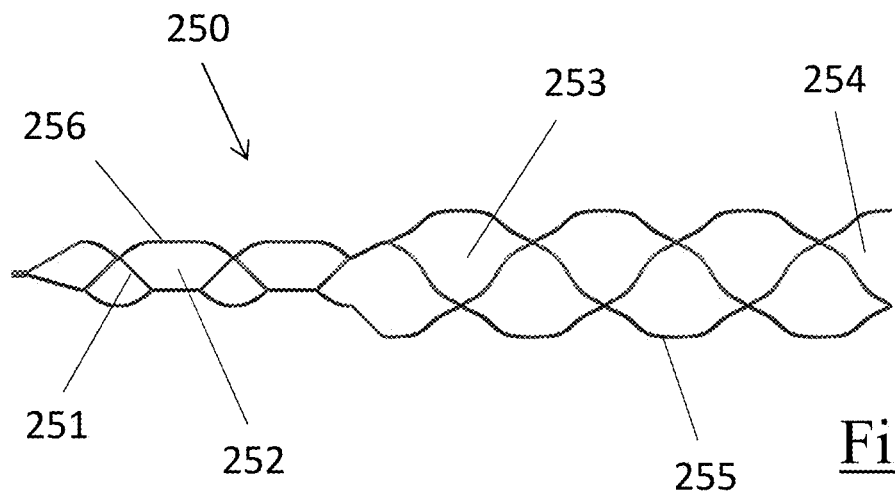
FIGS. 7a to 7e show a device assembly of the invention consisting of an inner and outer radial construction.

The effectiveness of this increased radial pressure at clot gripping can be further increased by maximising the angle of the struts to the longitudinal axis of the vessel. The greater the angle of the strut the greater the ability of the strut to grip the clot rather than slide past it. Ideally the strut would approach a 90-degree angle with the vessel axis for optimum grip, but this can be difficult to achieve in practice for a number of reasons. One major reason for this is the fact that the device is typically expanded to only a fraction of its freely expanded diameter when deployed under the clot initially. This is because it is advantageous for the device to be able to expand to a large diameter as it is retracted so that it can retain its grip on the clot and remain in contact with the vessel wall as it is retracted into larger more proximal vessels. The inventors have discovered an effective solution to this problem: namely a two-stage diameter device as shown in various Figs. throughout this disclosure, such as for example FIG. 7a. The proximal smaller diameter can be used to embed struts firmly in the clot for a secure grip at a steep opening angle, while the larger diameter distal section can expand to remain in contact with the vessel wall and protect against distal migration of the clot as it is retracted into larger vessels. This configuration enables strut angles of the proximal section to be larger than 30 degrees, or preferably larger than 45 degrees or even more preferably as large as 60 degrees to the vessel axis. FIG. 7d illustrates this point in greater detail.

Figure 4A:
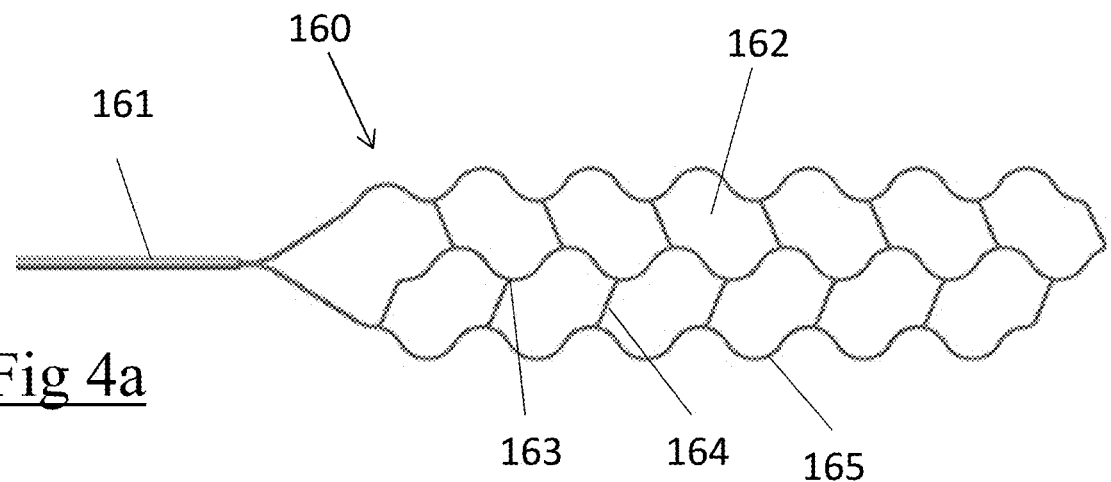
FIGS. 4a to 4e show the method of use of a flat configuration of the clot retrieval device of the invention.
Figure 4B:
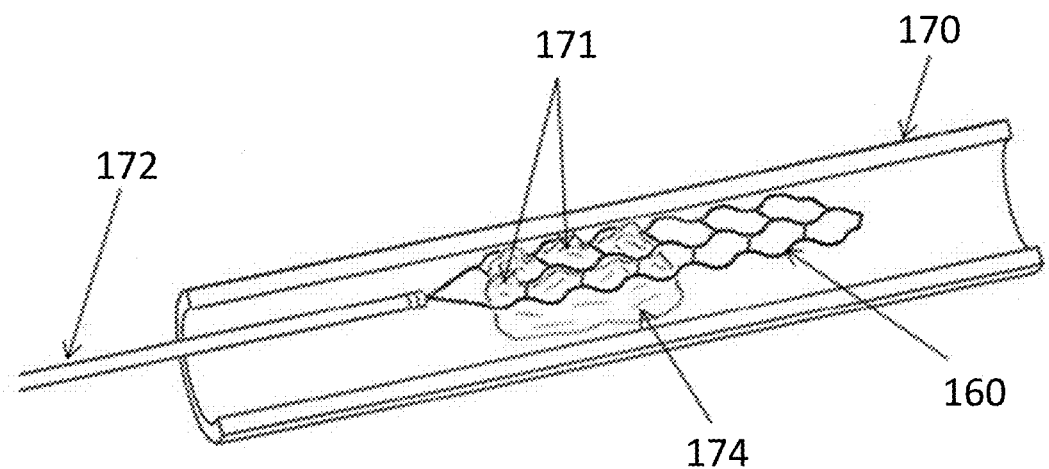
Figure 4C:
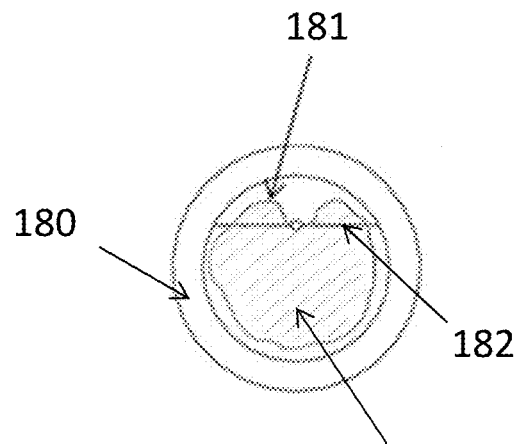

FIGS. 4a to 4e show another embodiment of the device formed from a flat sheet. FIG. 4a shows a plan view of the device 160 which in this embodiment is formed of two rows of cells 162 bounded by sinusoidal edges 165 and connected by cross struts 164. The device is connected to a proximal shaft 161. FIG. 4b shows an isometric type view of the device 160 deployed in an occlusive clot 174 which is located in a vessel 170. A cut away view of the vessel 170 has been provided for clarity. A microcatheter 172 is shown positioned on the proximal shaft with the tip of the microcatheter located at the joint between the clot engagement section of the device and the shaft. Where the clot 174 is in contact with the device 160, portions of clot 171 protrude through the cells. FIG. 4c shows a cross section view of the vessel 180, including the clot 183 and the device 182. This view illustrates the clot protruding through the cells of the device 181.

Figure 4D:
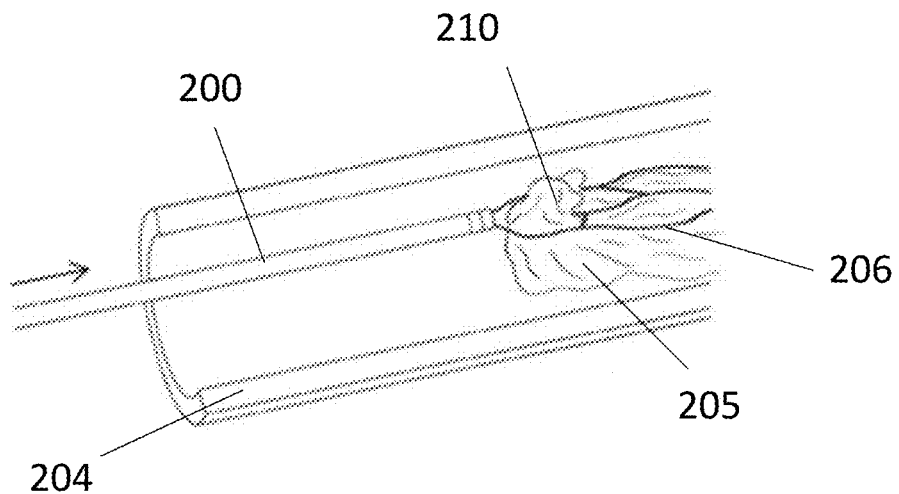
Figure 4E:
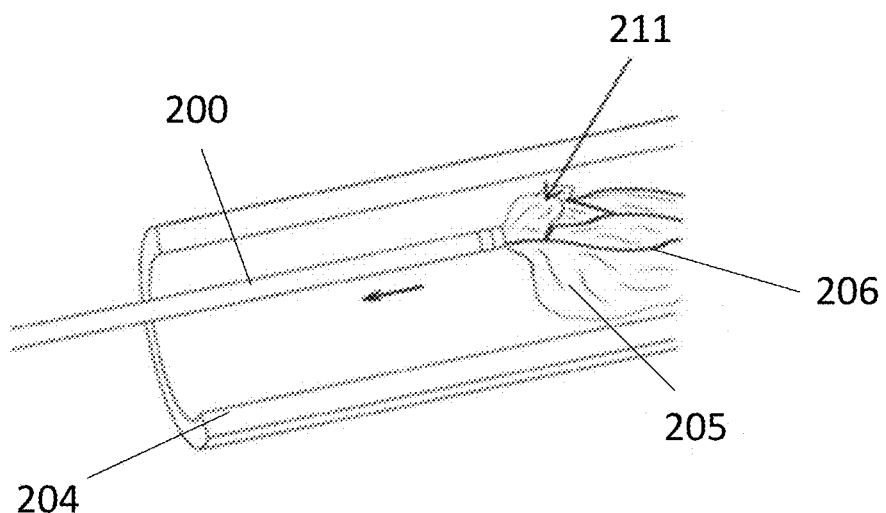
Figure 5A:
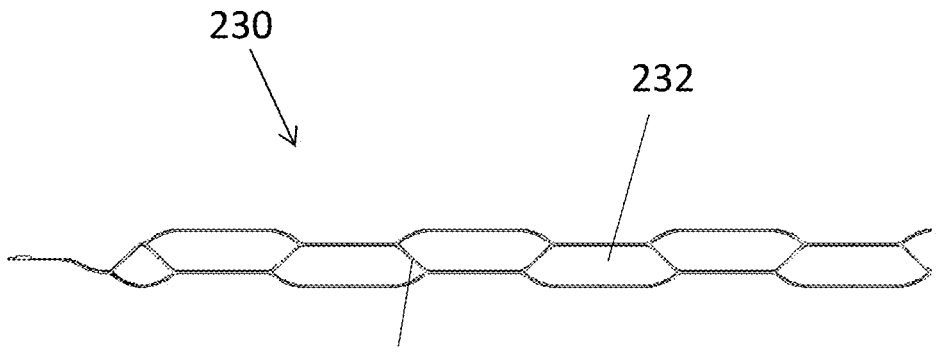
FIGS. 5a to 5d are a series of views of another embodiment of the invention.
Figure 5B:
Figure 5C:
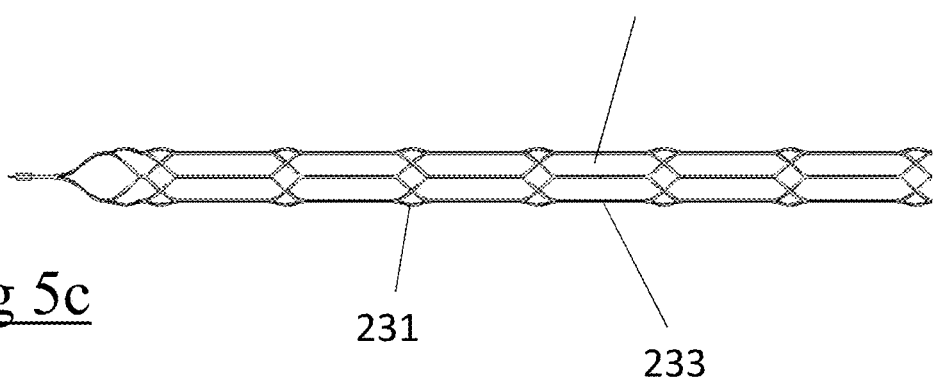
Figure 5D:
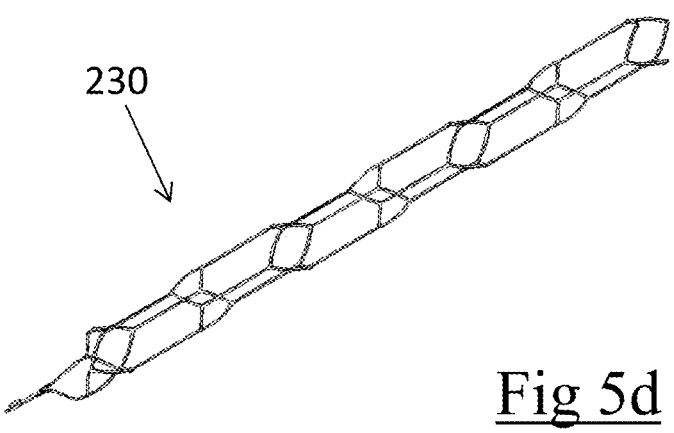

FIG. 4d is a magnified view of the proximal end of the device 206 showing how the clot is pinched as the microcatheter 200 is forwarded to partially re-sheath the device in the cut away vessel 204. The protruding portion of the clot 210 is trapped between the struts of the device and the microcatheter 200. FIG. 4e shows the device 206 and the microcatheter 200 being retracted at the same time, dislodging the body of the clot 205 from the vessel 204, due to the pinched grip on the protruding piece of clot 211.

FIGS. 5a-5d show an alternative tubular embodiment of the device of the invention. FIGS. 5a-5d show a side view, end view, plan and isometric view of device 230. This device has alternating rings of embedding struts 231 with low radial force segments 232, along its length. The preferred embodiment contains between 4 and 8 struts in a radial pattern for optimum embedding in the clot. The connecting struts 233 in section 232 in this embodiment are straight for optimum pushability to ensure the device can be delivered through tortuous anatomy.

FIGS. 6a-6d show another embodiment of the invention. FIGS. 6a-6d show a side view, plan, end view and isometric view of device 240. This device has alternating rings of embedding cells 241 with low radial force segments 242. The preferred embodiment contains between 2 and 4 cells in a radial pattern for optimum embedding in the clot. The use of a ring of cells instead of a ring of struts in this embodiment may improve clot pinching as the distal ring of struts 244 in each segment stays expanded for longer even as the more proximal ring of struts 245 is wrapped down by the microcatheter as it advances. This maintains strut embedding in the clot for longer improving the pinch of the clot between the struts and the microcatheter.

FIGS. 7a-7d illustrate an embodiment which consists of an assembly of an outer cage and an inner component. In this embodiment the proximal part 256 of the outer component 250 is designed to pinch clot in the same manner as described for FIGS. 1 and 2 and contains alternating segments of cells 251 for embedding in the clot, and segments 252 of low radial force and low scaffolding. This proximal part 256 of the outer component is joined to a body section 255 which has an increased diameter and larger cells 253 for additional clot retention as it is retrieved into larger vessel diameters in the Internal Carotid Artery before retraction of the device and clot into the access guide catheter or introducer sheath. The ratio of the body section 255 diameter to the proximal section diameter can vary from 1.5:1 to 4:1, and in the preferred embodiment is between 2:1 and 3:1.

Figure 7B:
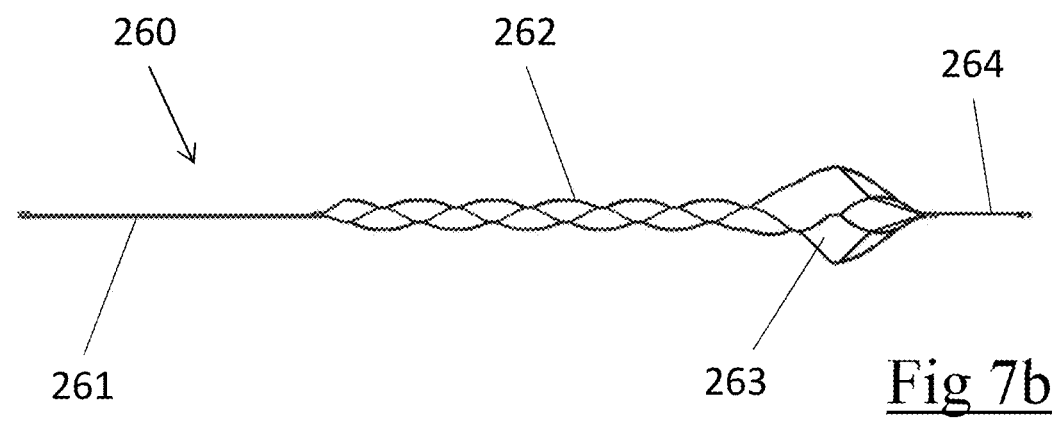
Figure 7C:
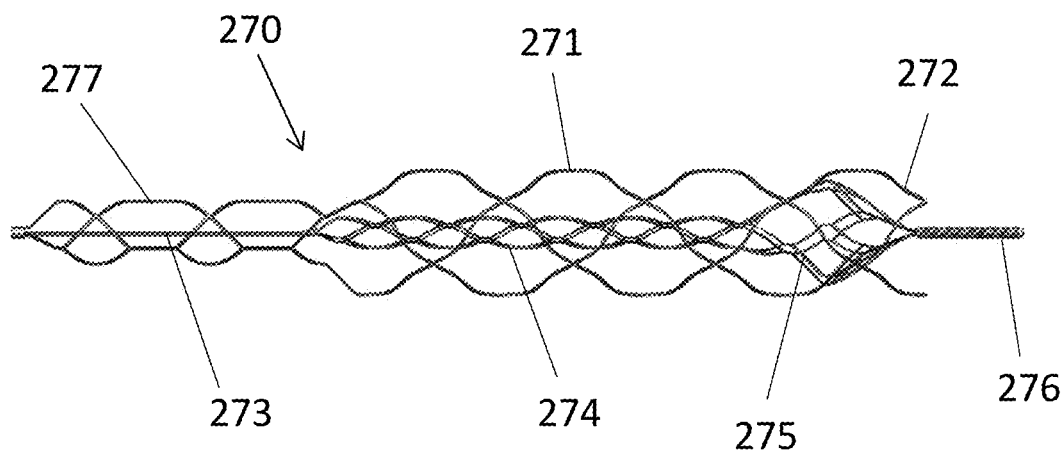
Figure 7D:
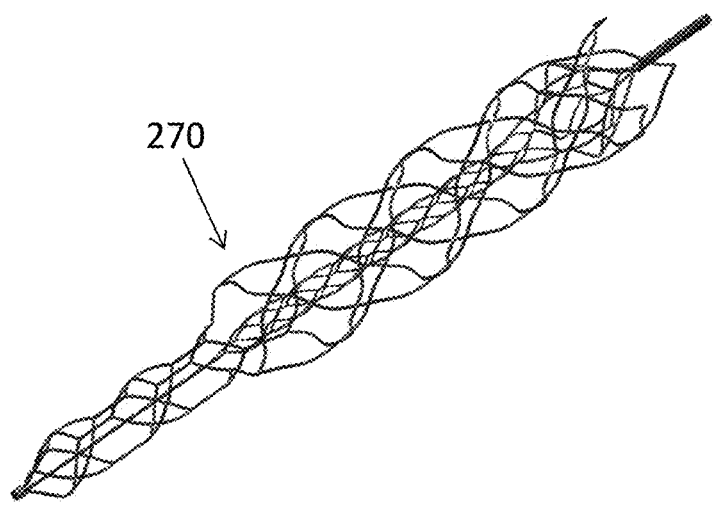

FIG. 7b shows the inner component 260 of the assembly. This component contains an elongated proximal strut 261 which connects the body section 262 to the shaft (not shown). The component 260 also contains a fragment protection structure 263 and a distal atraumatic tip 264. FIG. 7c shows how the two components are aligned in the assembly 270. The elongated proximal strut 273 is positioned under the proximal part of the outer cage 277 so that there is minimal restriction to clot protrusion into the low radial force segments. The body section of the inner component 274 is positioned in the body section of the outer component 271 and provides a flow channel to break the pressure gradient across the clot and provide flow restoration. The distal fragment protection structure 275 sits inside the end of the outer cage which has an open end 272 and provides protection against the loss of clot fragments and emboli. FIG. 7d shows an isometric view of this assembly 270.

Figure 7E:
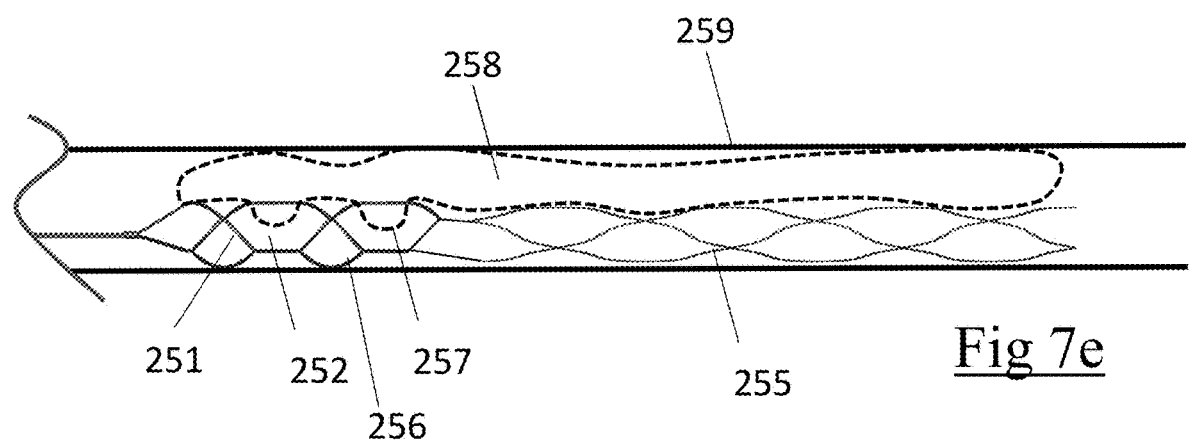

FIG. 7e shows device 250 deployed within a clot 258 in a vessel 259, illustrating a key advantage of a stepped diameter design such as that of the clot engaging element 250 of FIG. 7a. The relatively high radial force and radial pressure of the struts of the proximal section 256 allow the struts 251 of the section to embed deeply into the clot, creating clot bulges 257 which can subsequently be pinched within cells 252 by the advancement of a microcatheter (not shown). In addition, the smaller freely expanded diameter of the proximal section 256 means that the struts 251 of this section are inclined at a much steeper angle than those of the distal section 255, which enables them to much more effectively grip the clot for secure retraction. The description in relation to FIGS. 3c and 3d describes the significance of these strut angles in more detail.

Figure 8:
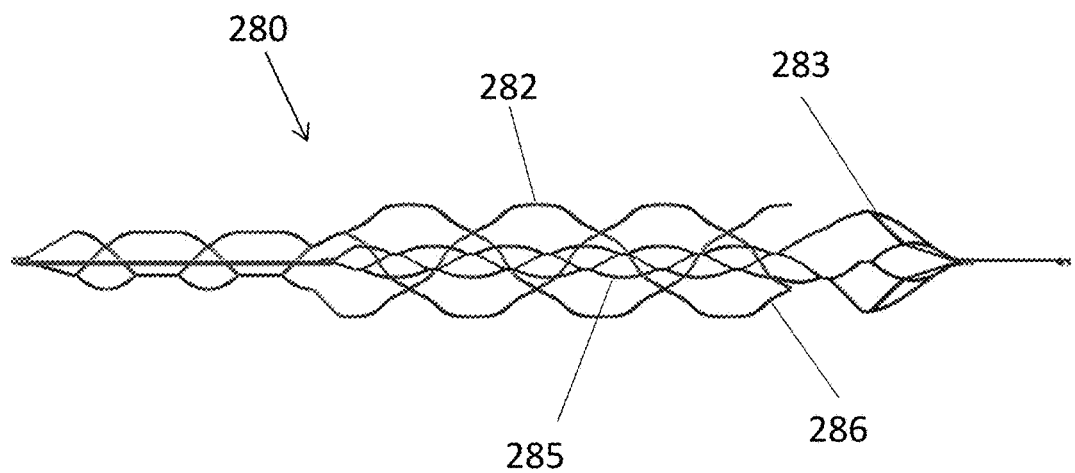
FIG. 8 is a side view of another configuration of the device shown in FIGS. 7a to 7e.

FIG. 8 shows another configuration 280 of the assembly shown in FIGS. 7a to 7e where the fragment protection structure 283 connected to the inner component 285 is positioned distal of the end of the outer cage 282. Ensuring there is a gap between the end of the outer cage 286 and the fragment protection structure 283 may improve the fragment protection performance particularly as the device is retracted in tortuous vessels. It may also be beneficial as the device is retrieved into a catheter as the fragment protection zone 283 will still be fully expanded and provide protection as the outer cage is fully retrieved.

Figure 9:
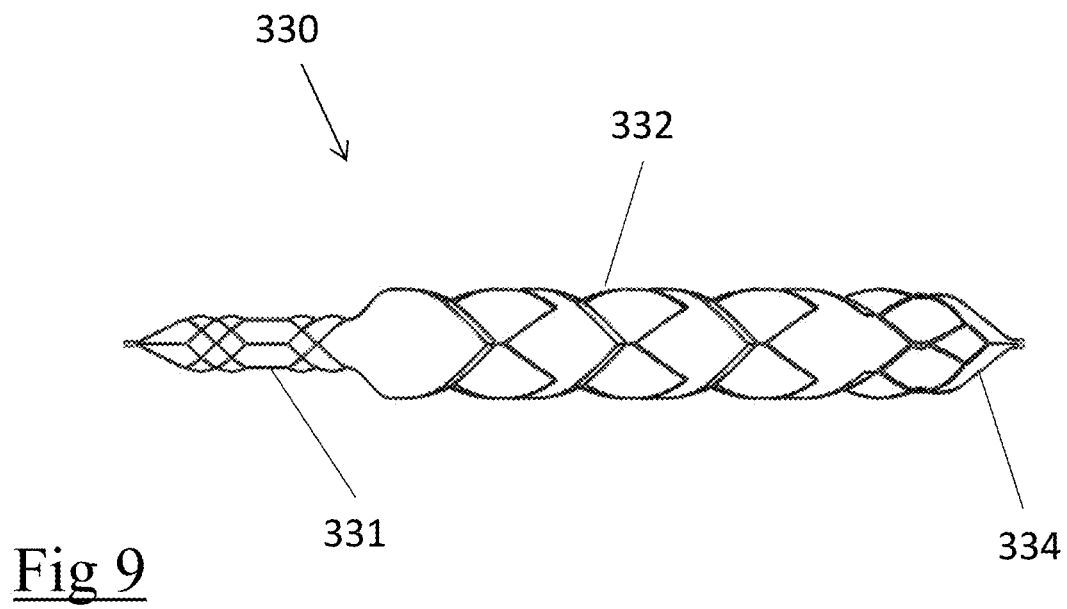
FIG. 9 is an image of the invention formed as part of an outer cage.
Figure 10:
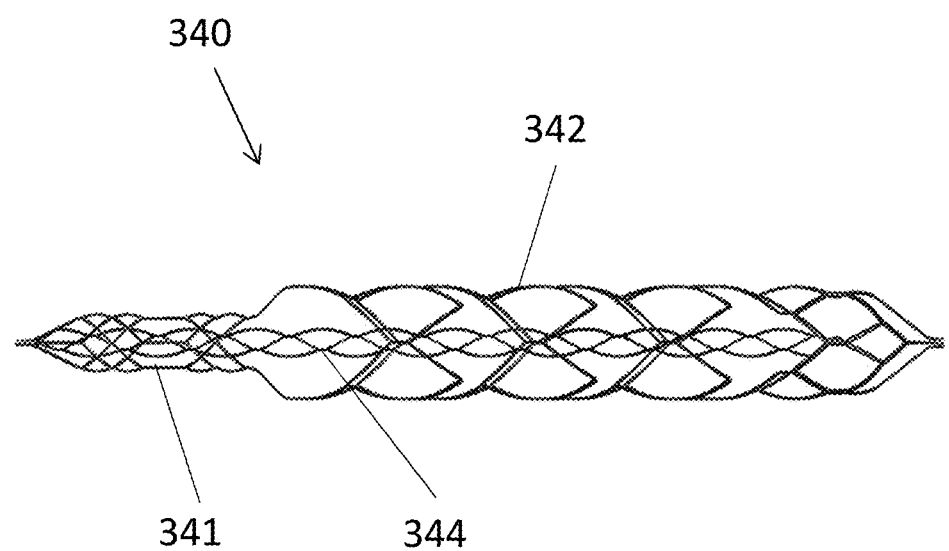
FIG. 10 illustrates an assembly of the device containing the outer cage shown in FIG. 11 and an inner channel.

FIG. 9 is a side view of another outer cage configuration 330 where the proximal part 335 of the component is designed to pinch the clot as described in FIGS. 7a to 7e, when a catheter is forwarded distally. In this configuration the component 330 also contains a body section 332 for clot retention during retrieval and a distal fragment zone 334. FIG. 10 shows an assembly 340 of the outer cage 342 described in FIG. 9 and an inner channel 344. The inner channel 344 in this assembly 340 runs the full length of the outer cage 342 including under the proximal section 341.

Figure 11:
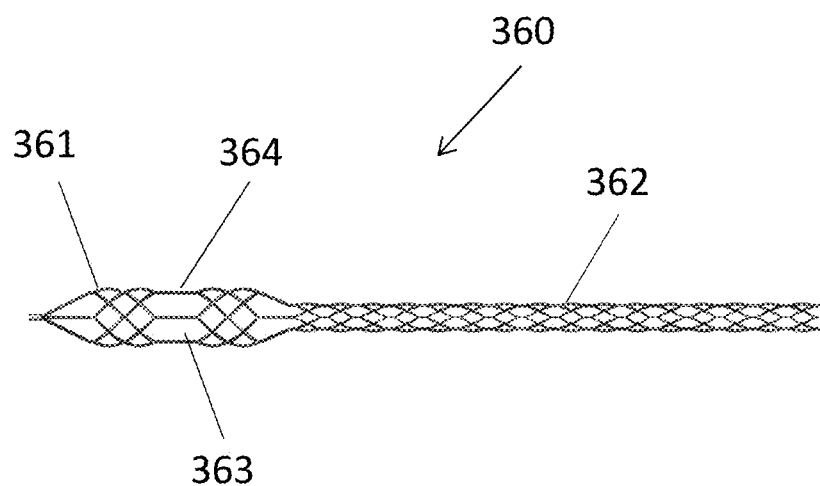
FIG. 11 is a view of the invention formed as part of an inner channel.
Figure 12:
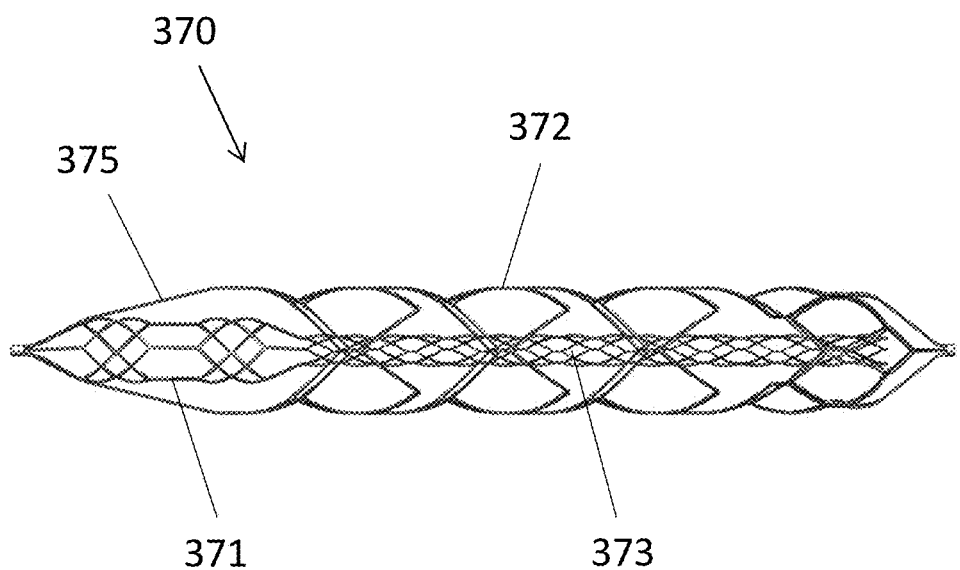
FIG. 12 illustrates an assembly of the device containing the inner channel shown in FIG. 11 and an outer cage.

FIG. 11 shows an inner component 360 which consists of a body section 362 and a proximal section 364 which contains alternating segments of embedding cells 361 and low scaffolded areas 363 to promote clot protrusion and clot pinching. FIG. 12 illustrates how this inner channel design 373 can be integrated in an assembly 370 with an outer cage 372. The outer cage 372 has extended proximal struts 375 to minimise any obstructions to the clot engaging with the proximal section 371 of the inner component.

Figure 13:
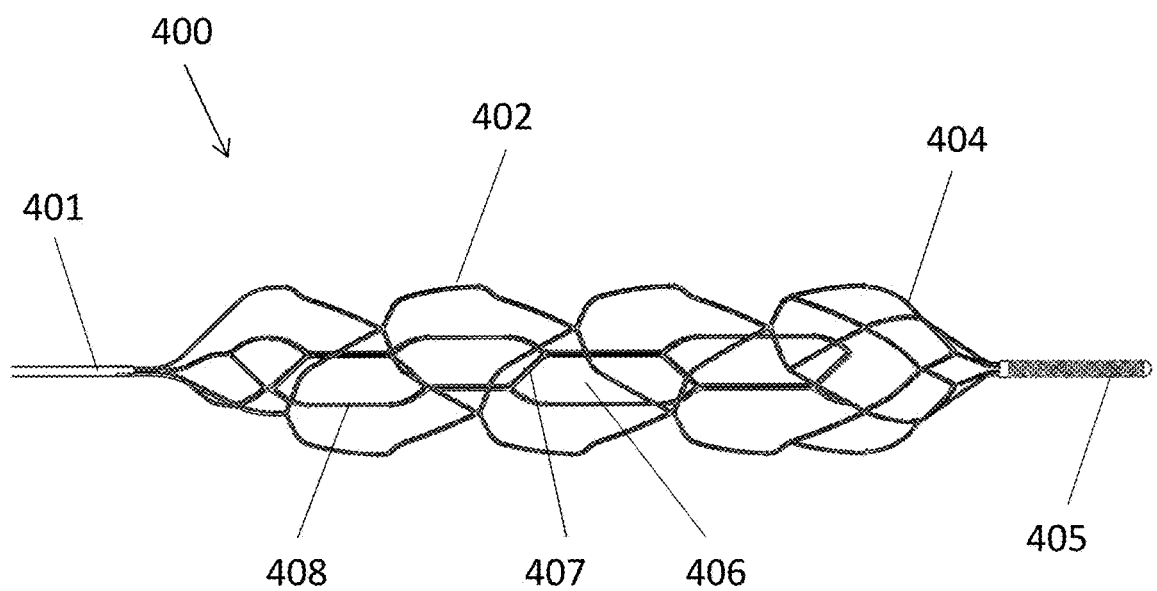
FIG. 13 illustrates another embodiment of the invention where the outer cage cells align with the inner channel cells.

FIG. 13 shows another embodiment of the invention 400 consisting of an assembly of an outer cage 402 and an inner channel 408. These two components are connected to a proximal shaft 401 and a distal radiopaque tip 405. In this embodiment the inner channel 408 is designed to facilitate clot pinching as described elsewhere in this specification by having alternate rings of struts 407 for deep embedding in the clot, adjacent to areas of low strut density or scaffolding 406. As this inner component 408 is positioned inside of the outer cage 402, there is the potential for the struts of the outer cage to obstruct clot embedding and protrusion in the inner channel 408. To eliminate this issue, the outer cage 402 is designed so that the struts of the outer cage align with the struts of the inner channel 408, when the outer cage is partially expanded to the same diameter as the freely expanded inner channel.

Figure 14A:
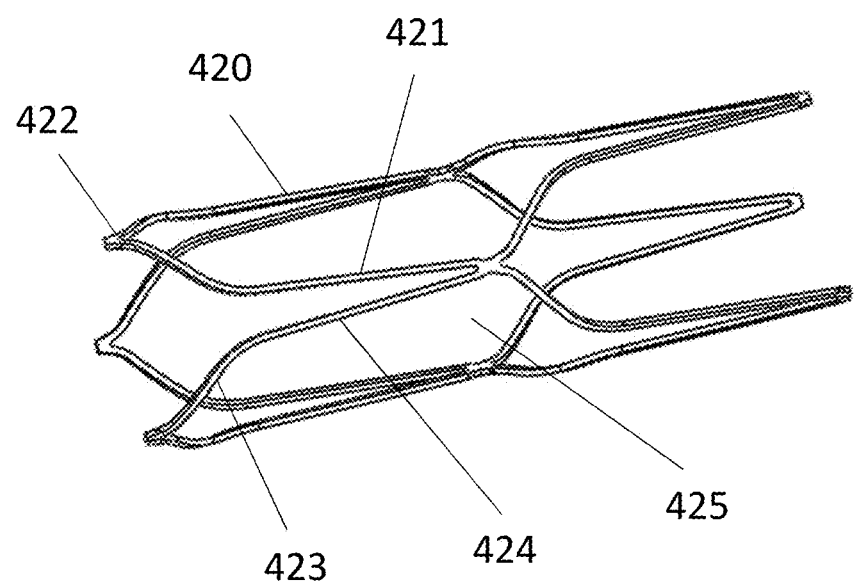
FIGS. 14a to 14b shows a segment of the outer cage shown in FIG. 13.
Figure 14B:
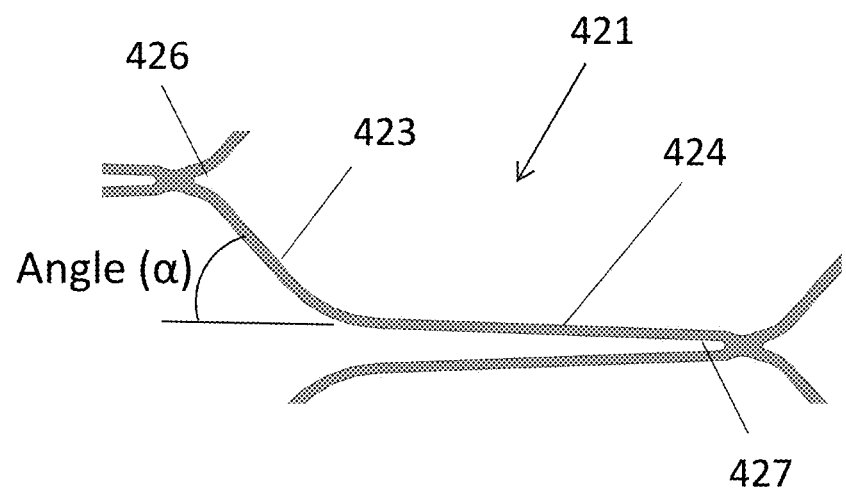

FIGS. 14a and 14b show a segment 420 of the outer cage illustrated in FIG. 13. The segment 420 is shown expanded to a diameter greater than the freely expanded diameter of the inner channel but below the freely expanded diameter of the outer cage in FIG. 14a. The 'dog-leg' shape of the strut 421 can be seen in the image and this shape strut is repeated around the circumference and along the length to form cells 425. FIG. 14b shows how the strut shape consists of a short segment 423 connected to a longer segment 424 at an angle (A) as shown. This angle can vary from 20° to 90° and in the preferred embodiment is 30° to 60°. The short segment of strut 423 may also have an increased strut width compared to the longer segment 424. In this configuration the short strut segment 423 has a higher expansion force than the longer strut segment 424 therefore it will have preferential expansion and the crown 426 will open before the crown 427 expands. This gives the outer cage a two-stage expansion process with struts 423 and crown 426 fully expanding before the struts 424 and crown 427 expand. This two-stage expansion process also results in a radial force profile that reduces when the first stage expansion is complete. This strut configuration can be produced by laser cutting this strut profile form a nitinol tube which has a diameter equal to or greater than the first stage expansion diameter. Alternatively, the part can be laser cut from a smaller tube and the struts constrained in this shape during heat-setting.

Figure 15:
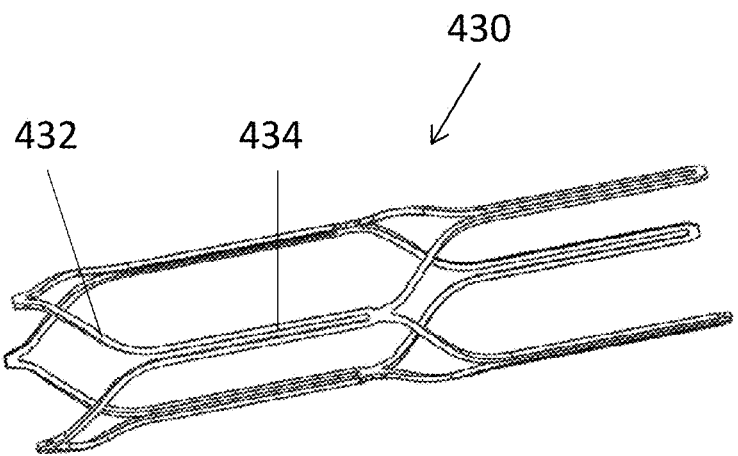
FIG. 15 shows a segment of the outer cage shown in FIG. 13 at reduced diameter.
Figure 16:
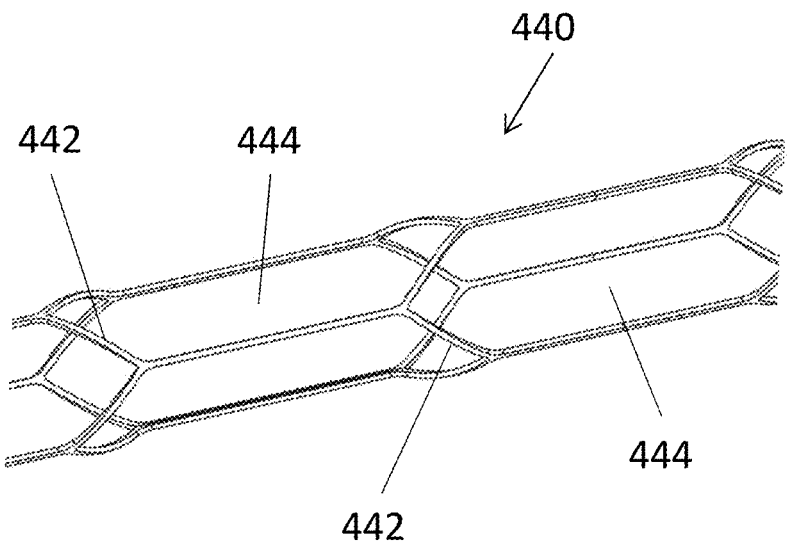
FIG. 16 shows a segment of the inner channel shown in FIG. 13.

FIG. 15 shows the same outer cage segment as FIG. 14. In this image however, the segment 430 is at the same diameter as the freely expanded inner channel. This is the same diameter as the end of the first stage expansion step when struts 432 are fully expanded but struts 434 are still collapsed. FIG. 16 shows the segment of the inner channel which aligns with the outer cage segment illustrated in FIGS. 14 and 15. As discussed in FIG. 13 this segment 440 contains rings of struts 442 and areas of low radial force and strut density 444.

Figure 17:
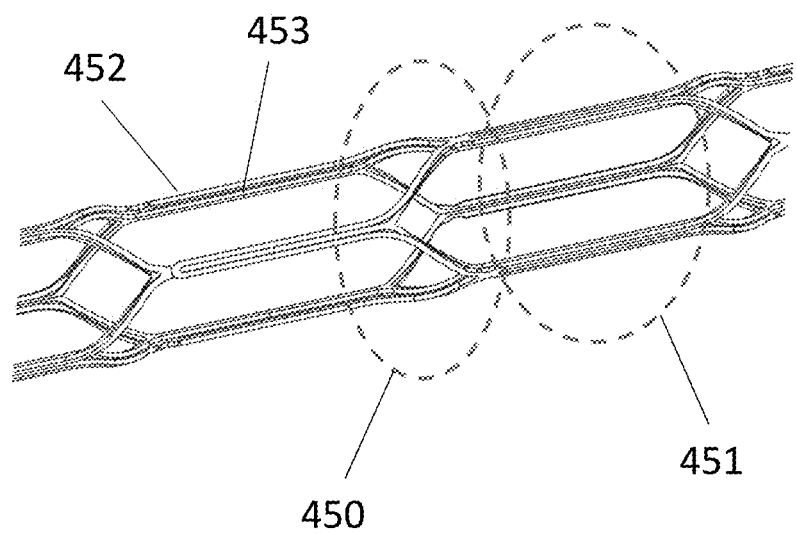
FIG. 17 shows the alignment of the inner and outer component segments.

FIG. 17 shows the outer cage segment 452 (described in FIG. 15) overlapping the inner channel segment 453 (described in FIG. 16). The benefit of this design is that the struts of both segments fully align as shown, so there is no obstruction to the strut section 450 embedding in the clot. Similarly, there is no obstruction to the clot protruding into cell area 451, thereby facilitating a pinch when the microcatheter is forwarded distally. In addition, as the device is retracted proximally towards the guide catheter or sheath, the outer cage can continue to expand and maintain contact with the clot even as the vessel diameter increases.

Figure 18:
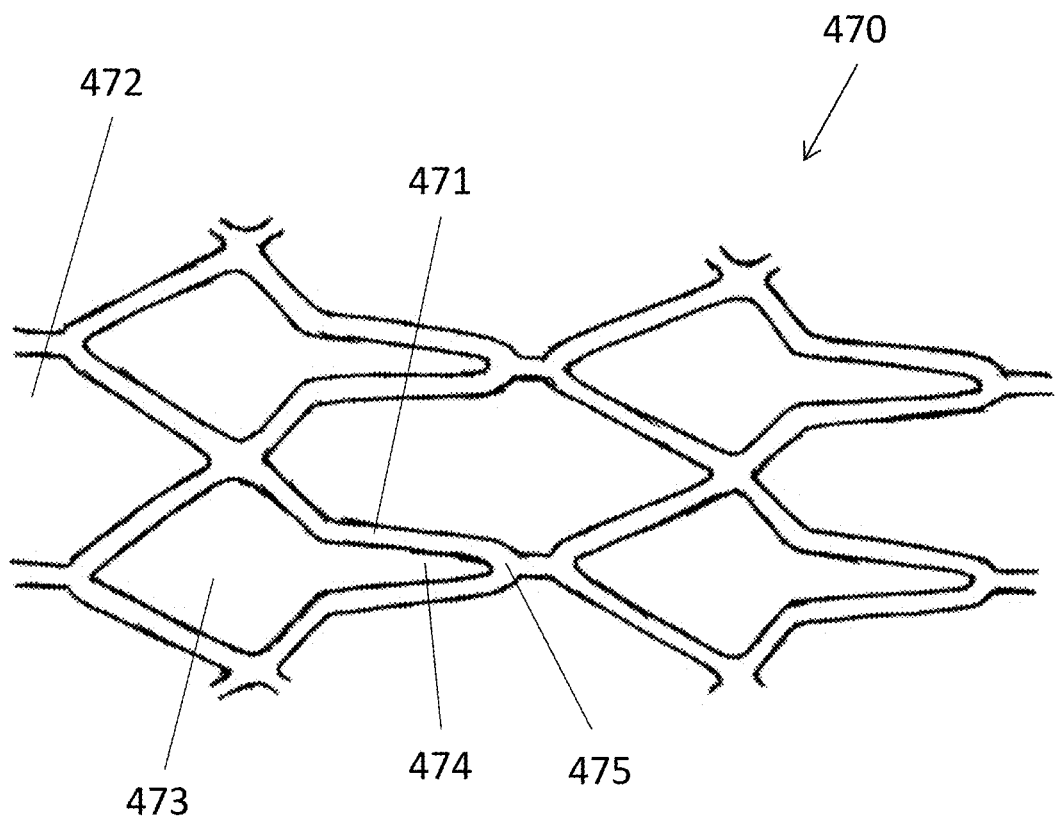
FIG. 18 illustrates an example of a cell pattern of the invention.

FIG. 18 shows a cell pattern 470 beneficial to clot pinching. This pattern 470 can be incorporated in a tubular or flat device configuration. When deployed across an occlusive clot in the vasculature, clot protrusion occurs in the large cell area 473. After a suitable incubation time, the microcatheter can be advanced from the proximal side 472 to partially re-sheath the device. When the microcatheter contacts the clot protruding into cell 473 it forces the clot to move distally in the cell into area 474 between the struts 471. The narrowing struts channel the trapped clot towards crown 475 creating an improved pinch on the clot between the catheter tip and the device.

Figure 19:
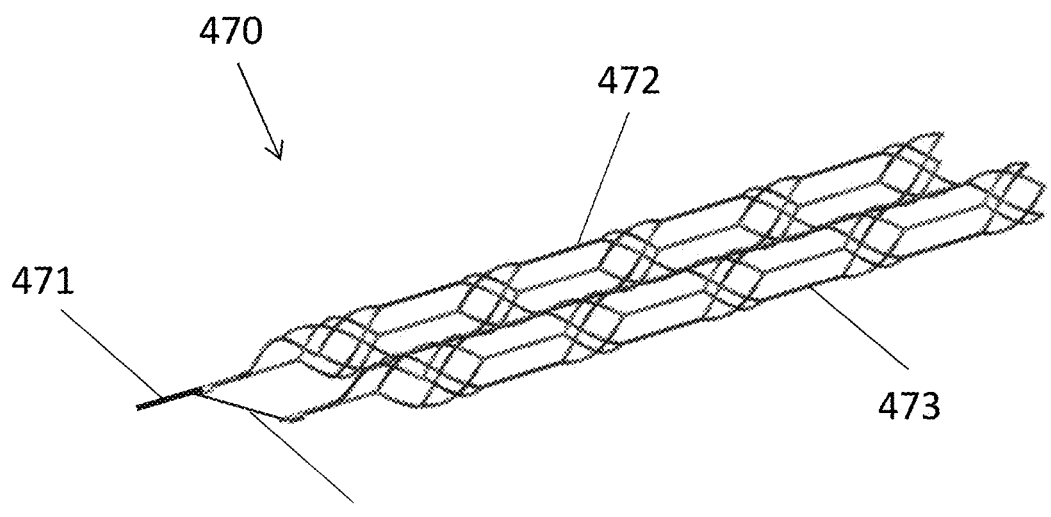
FIG. 19 shows an embodiment of the invention consisting of multiple structures.

FIG. 19 illustrates a configuration of the invention that consists of an assembly 470 of multiple tubular components connected in parallel. In the configuration shown two components 472 and 473 are connected at the proximal end by a strut 474 and subsequently to the proximal shaft 471. Both the components shown here, 472 and 473, are similar to the embodiments described in FIGS. 3 and 6. The alignment of these components may be staggered as shown in this image and the components may twist around each other along the length. More than two components may be connected together in this manner and the different components may have different diameters or be tapered along the length. The assembly of these components has the potential to improve clot pinching and grip when the device is partially re-sheathed with a microcatheter or intermediate catheter.

Figure 20A:
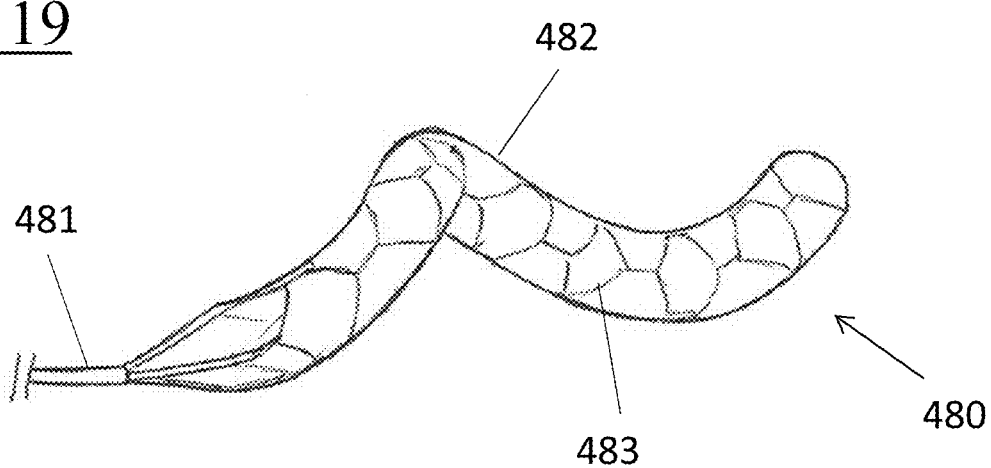
FIGS. 20a and 20b shows a clot retrieval device of the invention which spirals along the length of the device and the centre-line position on a mandrel.

FIG. 20a shows a configuration of the device where the tubular component 480 is formed into a helical or spiral shape 482 and is connected to a proximal shaft 481. The cut pattern of the component 483 is designed to promote clot embedding and grip as described in FIGS. 3 and 6. However in this configuration, the centreline of the component follows a helical track such as that shown in FIG. 20b, where the track 491 follows the surface of a cylindrical mandrel 490.

Figure 21:
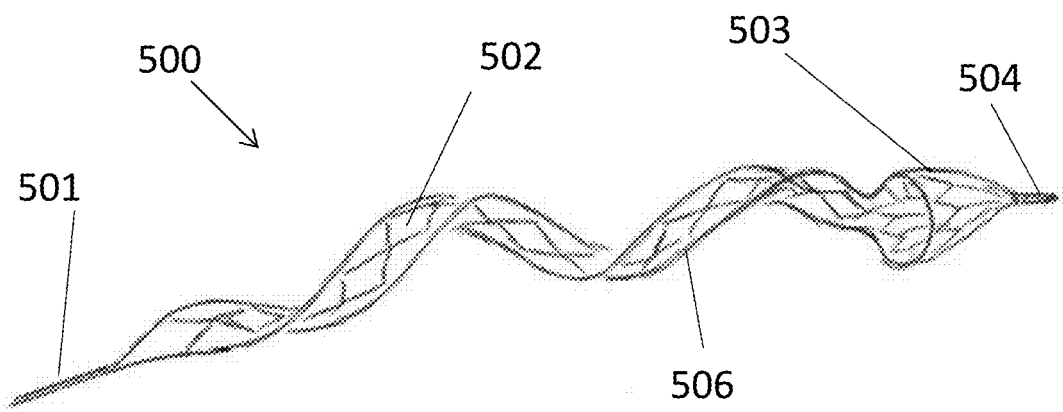
FIG. 21 is a view of another helical clot retrieval device with a flat mid-section.
Figure 22:
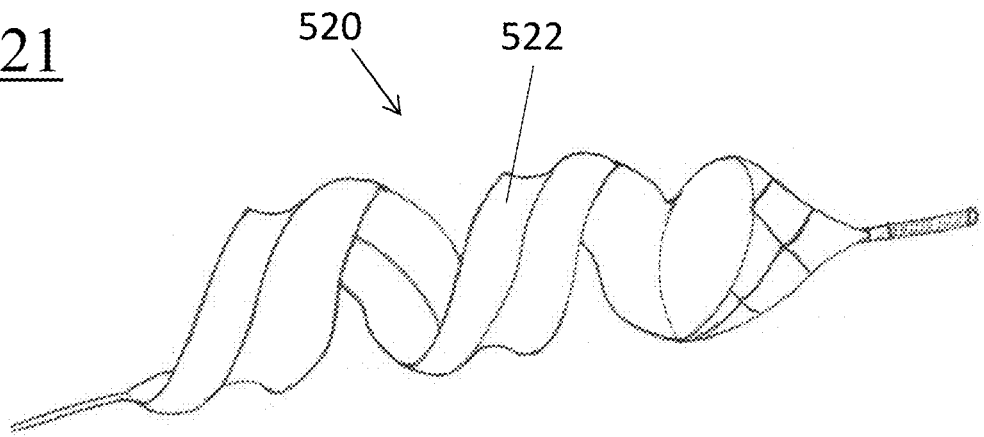
FIG. 22 shows another helical clot retrieval device of the invention with a profiled mid-section.
Figure 23A:
FIGS. 23a to 23c show cross section views of the mid portion of a series of spiral devices.
Figure 23B:
Figure 23C:

In another embodiment of the device shown in FIG. 21, a flat device 500 is formed so that the centreline of the device also forms a helical path in this case. This device can be formed by laser cutting the required strut pattern 502 from a tube or by cutting a flat sheet and then wrapping the flat part around a cylinder prior to heat-setting. Therefore, the device has a similar shape to wrapping a wide ribbon around a cylinder. When this device is deployed across as occlusive clot, the clot can protrude into the areas of low strut density but also into the central lumen of the helical coils. On device retraction this can improve clot grip and dislodgement performance and can also facilitate clot pinching if a microcatheter or intermediate catheter is forwarded distally over the device until it contacts the clot. The embodiment 500 shown has a flat cross section in the body part 506 of the device. The helical body section is connected to a proximal shaft 501 and a distal fragment protection structure 503 with a distal tip 504. FIG. 22 shows another device embodiment 520 similar to FIG. 21 except with a curved or profiled cross section shape for the body segment 522. FIGS. 23a-23c illustrate different examples of cross section shapes that may be incorporated in this configuration of the invention. FIG. 23a shows a flat cross section 531, FIG. 23b shows an 'S' shaped cross section 532 and FIG. 23c shows a curved cross section 533.

Figure 24A:
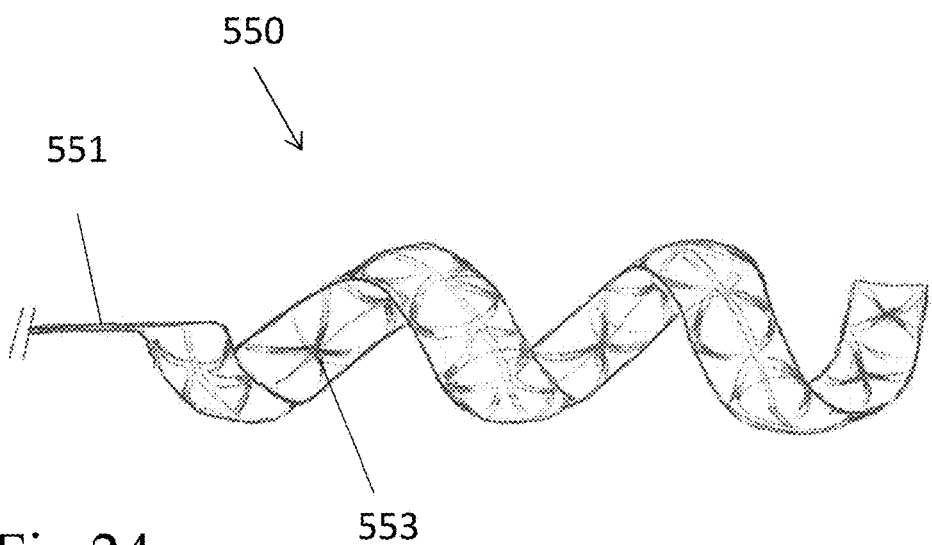
FIGS. 24a to 24b are views of another helical clot retrieval device of the invention.
Figure 24B:
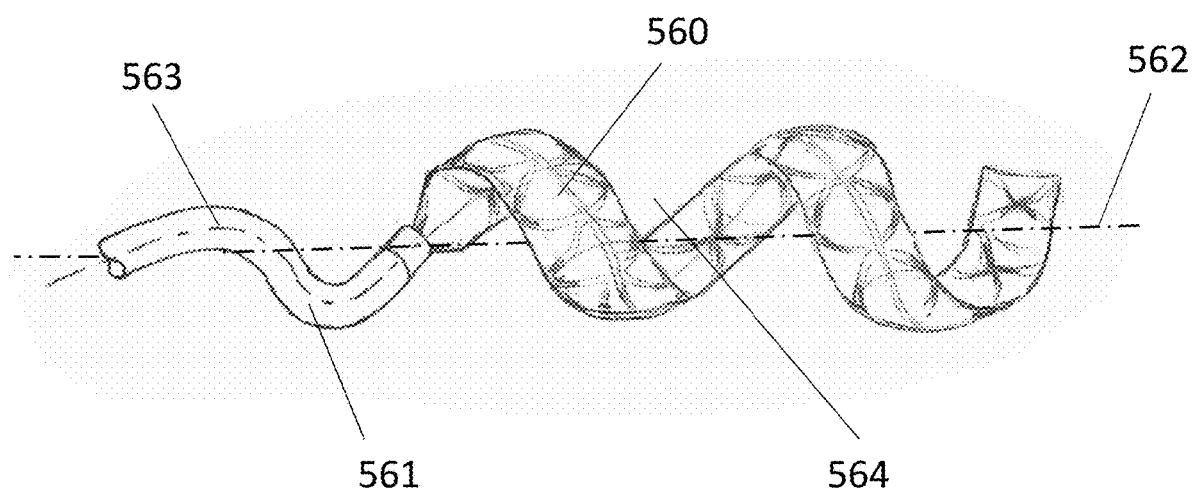
Figure 25:
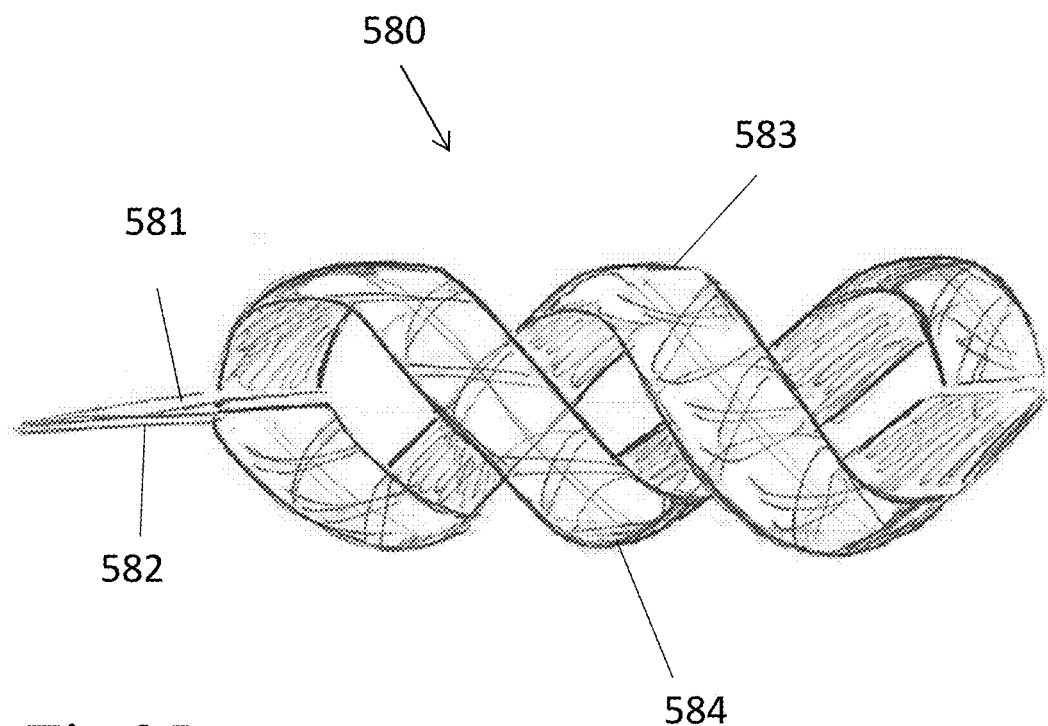
FIG. 25 illustrates a device formed from multiple helical components.

FIG. 24a shows another helical configuration of the device 550 with a curved cross section similar to that shown in FIG. 23c. The laser cut or wire formed clot engagement section 553 is connected to a proximal shaft 551. A microcatheter can be used with this device to pinch the clot and generate improved grip on the clot as described in FIG. 1. When the micro or intermediate catheter is forwarded over the device to pinch the clot it can follow the centreline of the vessel or alternatively it can follow the centreline of the device and follow a helical track as shown in FIG. 24b. If the catheter 561 follows the centreline of the vessel 562 during re-sheathing it can generate good pinching of the clot in the luminal space 564 within the helical coil. Alternatively, if the catheter 561 follows the centreline of the device 563 as shown, it can generate good pinching of the clot in the cells of the cut pattern 560. FIG. 25 shows an embodiment of the device 580 that is constructed from two helical components 583 and 584 to form a double helix type construction.

Figure 26:
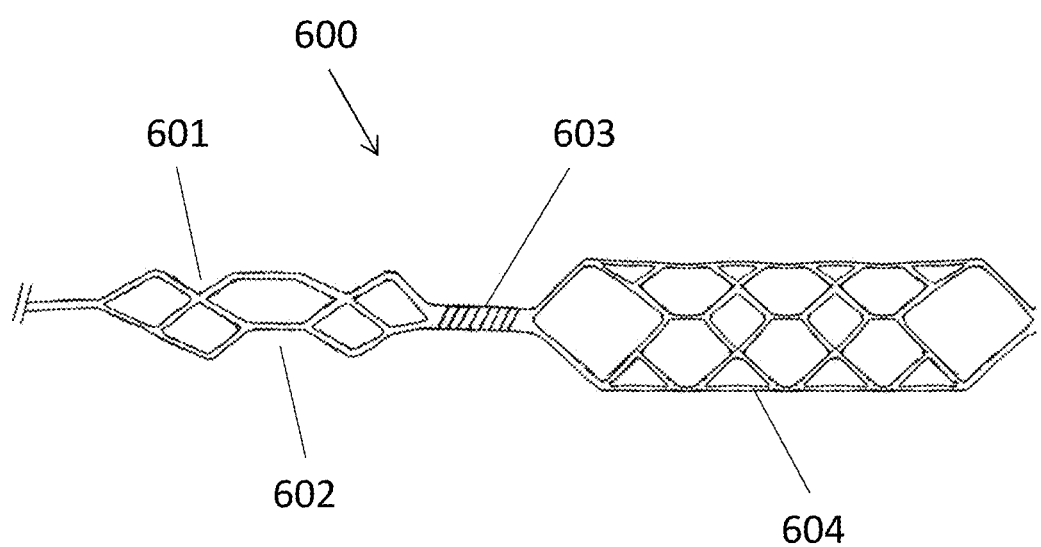
FIG. 26 shows an embodiment of the device that can elongate under tension.

FIG. 26 illustrates another embodiment of the invention 600 where the proximal part of the device 601 is designed to facilitate clot pinching if required, similar to that described in FIG. 7. The body section 604 is also similar to that described in FIG. 7, however in this embodiment the connection 603 between the proximal and body sections can elongate under tension. This facilitates the stretching of the clot during dislodgement by the device. The proximal end of the clot will be pinched and constrained on the proximal part of the device 601 while the distal end of the clot will be positioned on the body section 604. When the device is retracted the proximal end 601 will move first pulling the proximal end of the clot. If the distal end of the clot is stuck in the vessel, the body section of the device will remain static and the connector 603 will elongate. This will also elongate the clot peeling it from the vessel wall and reducing the dislodgement force. When the tension in the connector 603 equals the dislodgement force of the distal section of the clot the remainder of the clot will start moving. In this embodiment the elongating connector 603 is formed of a coil spring, however in another embodiment this elongating element could form part of the cut pattern of the outer cage.

Figure 27A:
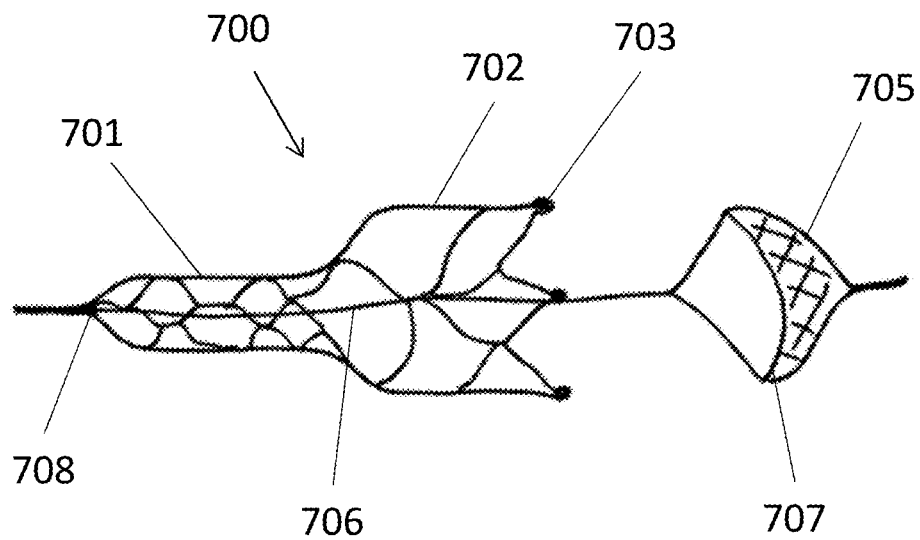
FIGS. 27a and 27b illustrate an embodiment of the invention containing a distal fragment protection structure.
Figure 27B:
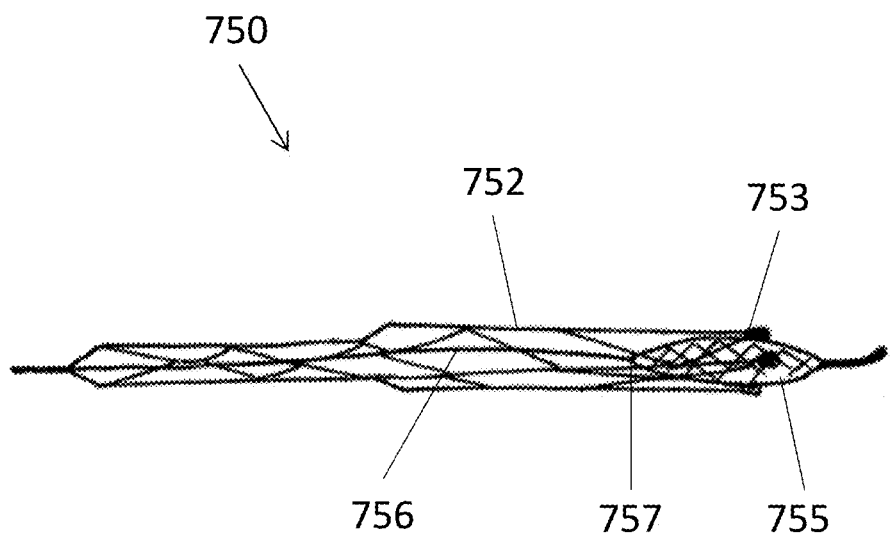

FIGS. 27a and 27b illustrate another embodiment of the device. FIG. 27a shows the device 700 in the freely expanded configuration. In this iteration of the invention the proximal part of the outer cage 701 is configured to promote clot embedding and clot protrusion to facilitate clot pinching. The body section 702 of the outer cage has an increased diameter compared to the proximal section, to ensure good clot retention as the device is retracted past bends and branches in the vasculature. The outer cage has an open distal end with radiopaque markers 703 shown on the distal crowns. The inner component in this assembly consists of a wire 706 connecting the fragment protection structure 705 with the proximal joint 708. In the freely expanded configuration there is distinct gap between the distal struts of the outer cage 703 and the leading edge of the fragment protection structure 707. This gap can vary from 1 mm to 20 mm and in the preferred embodiment will range from 5-10 mm.

FIG. 27b shows the same device as FIG. 27a except in this image the device 750 is at the diameter of the target vessel at the location of the occlusive clot. At this diameter the leading edge 757 of the fragment protection structure 755 is located inside the outer cage 752 and proximal of the distal crowns 753. This change in position of the fragment protection structure 755 relative to the outer cage 752 is due to the length differential of the outer cage 752 in the freely expanded configuration and at reduced diameters. Positioning the fragment protection structure inside the outer cage at small diameters minimises the parking space required distal of the clot for device deployment. In addition, positioning the fragment protection structure 755 distal of the outer cage 752 during device retraction in large vessels and during retrieval into a guide or intermediate catheter improves the efficacy of the fragment protection.

Figure 28:
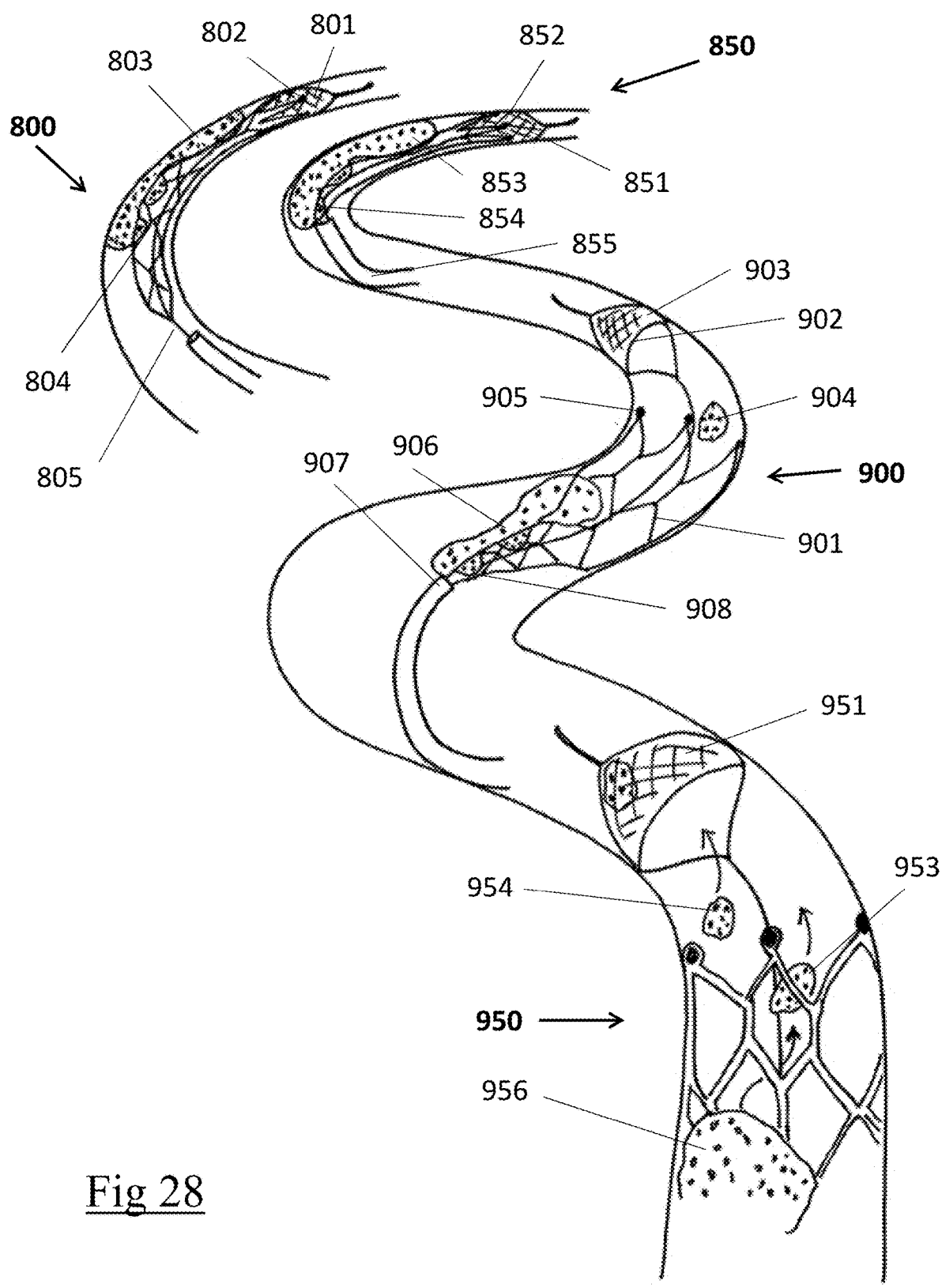
FIG. 28 shows the method of use of the device illustrated in FIG. 27.

FIG. 28 shows a method of use of the device embodiment described in FIG. 27. Device 800 is deployed across the clot 803 using standard interventional techniques and positioned so that the distal end of the device 802 and fragment protection structure 801 is positioned distal of the clot 803. The device 800 also contains a clot pinch portion 804 and is connected to an elongated proximal shaft portion 805.

Device image 850 shows the device in the vessel after the microcatheter 855 has been advanced to generate a pinch between the clot 853 and the proximal portion of the device 854. At this diameter in the target vessel location, the distal fragment protection structure 851 is partially inside the outer cage 852.

Device image 900 shows the device as it is retracted back into a larger diameter vessel. As the vessel diameter increases, the diameter of the outer cage 901 also increases and the outer cage length shortens. This creates a gap between the proximal edge 902 of the fragment protection structure and the distal end of the outer cage 905. This facilitates the capture of any fragments or emboli 904 liberated during the dislodgement and retrieval process. The clot 906 is still held pinched between the distal tip of the microcatheter 907 and the device 908.

Device image 950 also illustrates the effectiveness of the fragment protection structure 951 as it captures the clot fragments 954 and 953 released from the clot body 956 during the retrieval process.

Figure 20B:
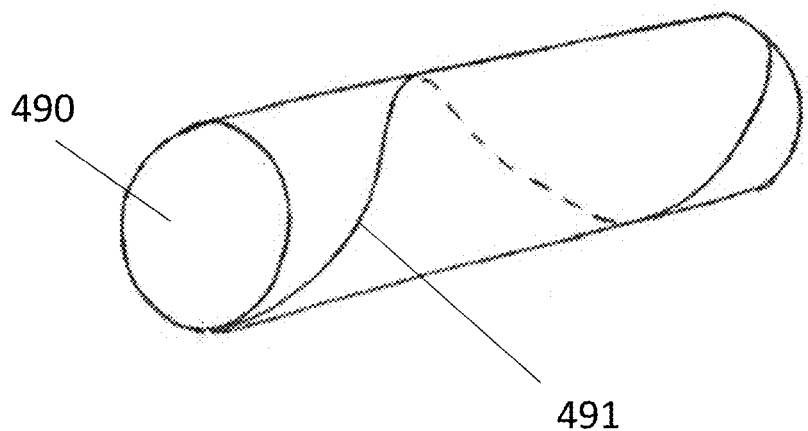
Figure 29:
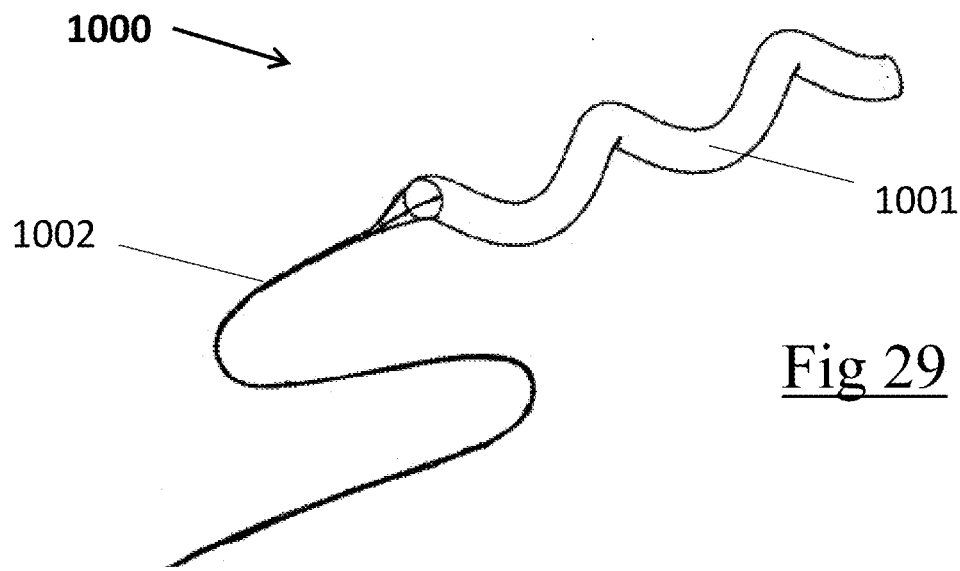
FIG. 29 illustrates another embodiment in which a tubular component is formed in a helical or spiral configuration.

The device 1000 shown in FIG. 29 is another embodiment of the device shown in FIGS. 20a and 20b where a tubular component 1001 is formed in a helical or spiral configuration and connected to a proximal shaft 1002. In this configuration the centreline of the component forms a helical track which follows the surface of a tapered or cylindrical mandrel as shown in FIG. 20b. The diameter of the tubular component can vary from 0.5 to 8.0 mm and in the preferred embodiment ranges from 1.0 to 4.0 mm. The diameter of the cylindrical mandrel that the helix track follows can vary from 1.0 to 10.0 mm and in the preferred embodiment ranges from 2.0 to 7.0 mm. The pitch of the helix can vary from 3.0 to 30 mm and in the preferred embodiment ranges from 10.0 mm to 20.0 mm.

Figure 30:
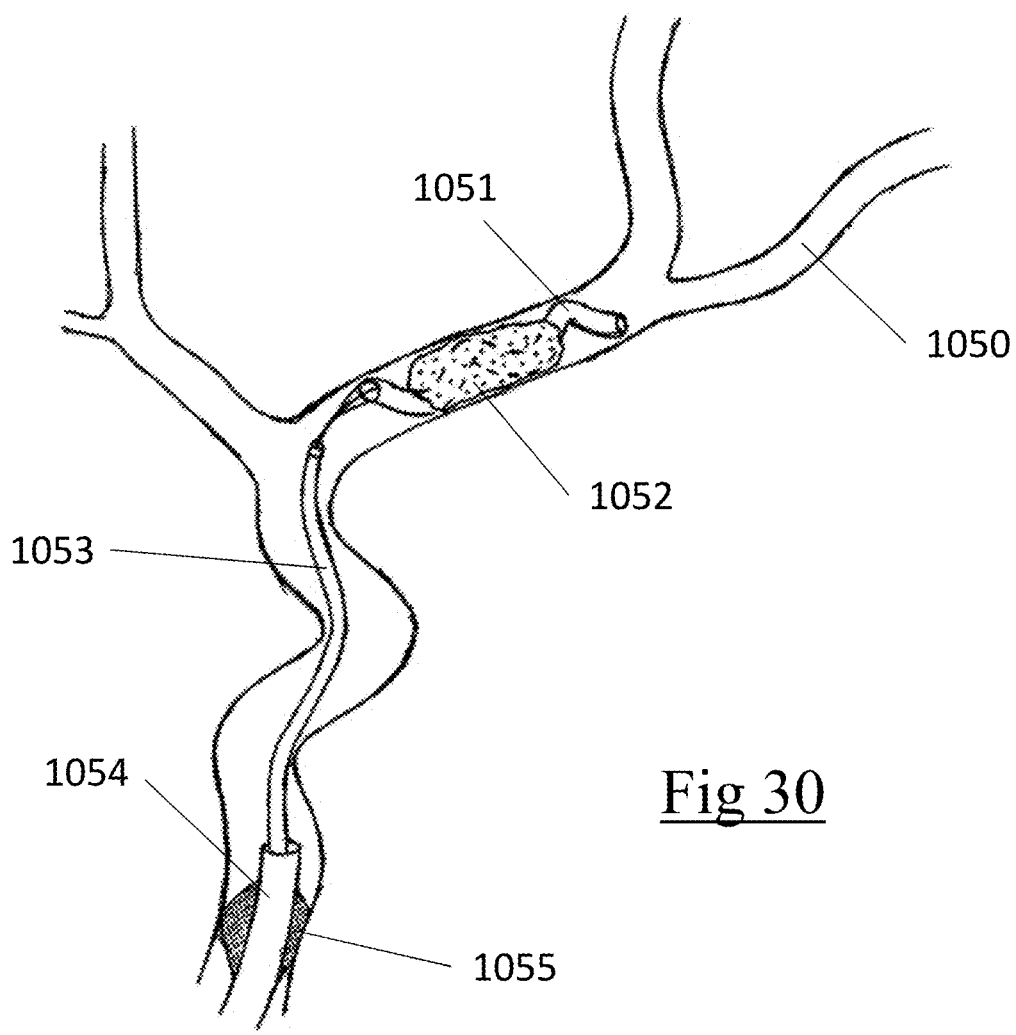
FIG. 30 illustrates the device of FIG. 29, in use.

The helical configuration of this device provides performance benefits for clot dislodgement as the device engages more with the clot than for a straight configuration. The clot embeds deeper in the cells and between the struts of the device improving the grip of the device on the clot. This occurs due to the helical shape which positions portions of the device away from the surface of the vessel and in the body of the clot. This is shown in FIG. 30 where the spiral device 1051 is deployed within the clot 1052 in the neurovascular vessels 1050. The device 1051 is deployed as per standard procedure for deploying a stent retriever, by delivering it through and then retracting the microcatheter 1053. In one method of use, the device 1051 can be retracted directly to dislodge the clot 1052 and retrieve it into the access catheter 1054. Aspiration may be utilised during the procedure and flow arrest may be provided by inflating the balloon 1055 on the access catheter 1054. Alternatively, after deployment of the device 1051 in the clot, the microcatheter 1053 can be forwarded again to partially re-sheath the device 1051 and generate a pinch on the clot between the distal tip of the microcatheter and the struts and crowns of the device 1051 as described elsewhere in this specification. The device, microcatheter and clot can then be retracted as a unit into the access catheter, utilising flow arrest and aspiration, if required.

Figure 31:
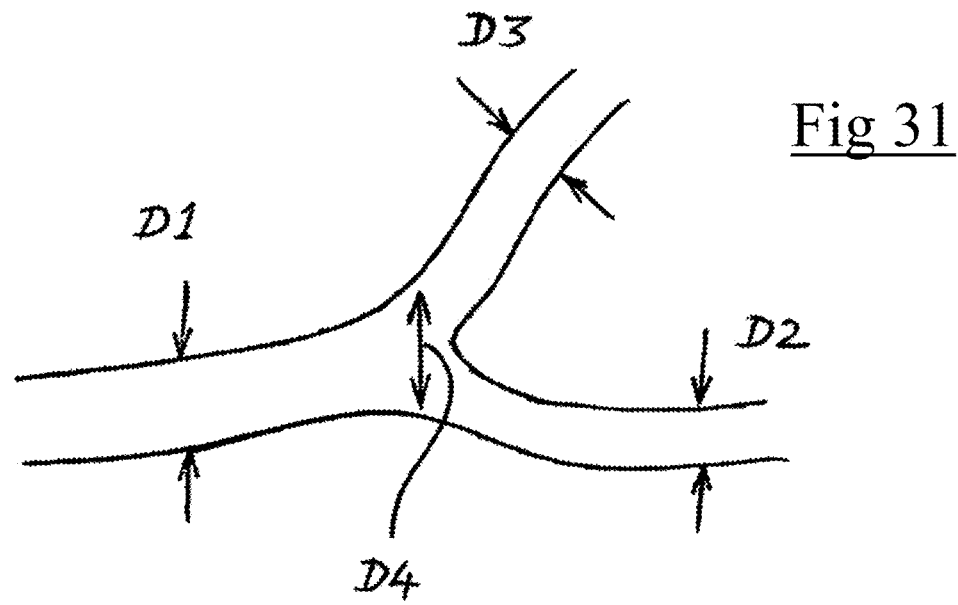
FIG. 31 is a view of a vessel bifurcation.
Figure 32A:
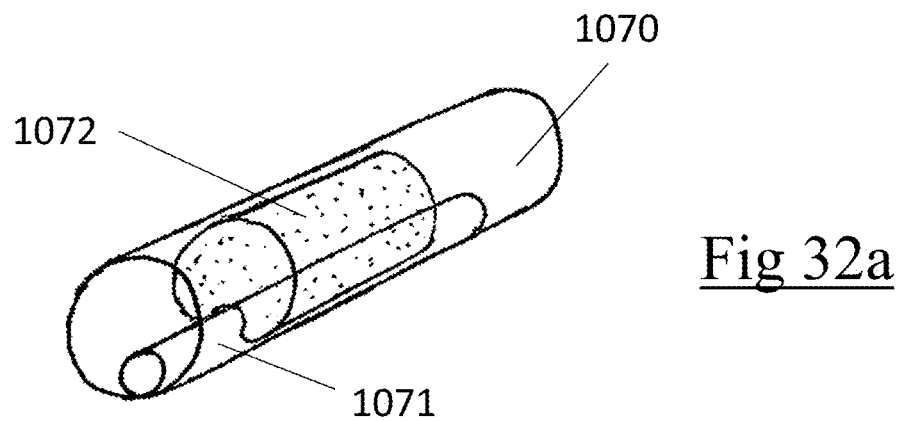
FIGS. 32a and 32b illustrate the differences in engagement in a clot of a straight tubular component (FIG. 32a) and a tubular component in a helical configuration (FIG. 32b)
Figure 32B:
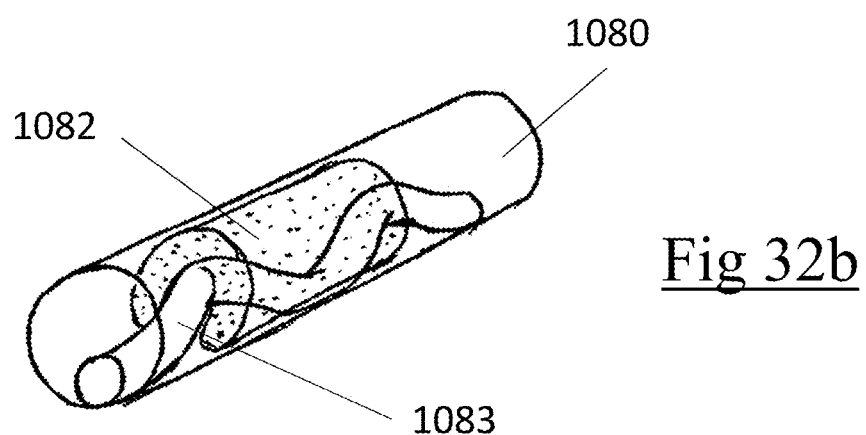

The increased depth of clot embedding in a device with a helical or corkscrew configuration is particularly useful for obtaining a pinch on clots in difficult vessel tortuosity and in vessel bifurcations as shown in FIG. 31 where the effective diameter of the bifurcation (D4) is larger than the diameter of the proximal (D1) or distal (D2, D3) vessels. This is further illustrated in FIGS. 32a and b, where FIG. 32a illustrates a straight tubular component 1071 deployed in a clot 1072 within a vessel 1070. FIG. 32b shows improved engagement and embedding in the clot 1082 when the tubular component 1083 (with the same diameter as component 1071 in FIG. 32a) is formed with a helical configuration. The helical configuration increases the depth the device 1083 engages within the clot and also the surface area of the device in contact with the clot.

Figure 33:
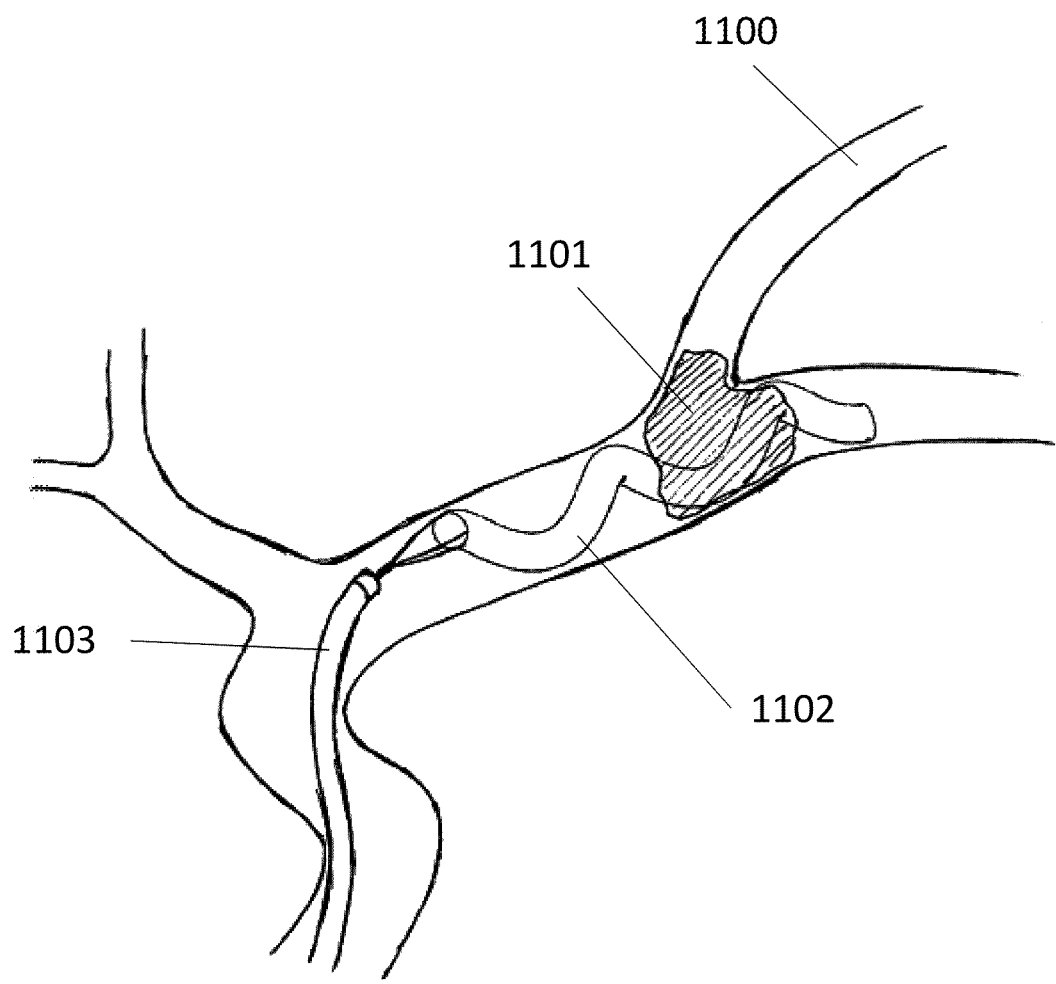
FIG. 33 is a view of a helical tubular component deployed in a clot located at a vessel bifurcation.

FIG. 33 shows a helical tubular component 1102 deployed in a clot 1101 which is located in a bifurcation of the anatomical vessels 1100. The microcatheter 1103 can be forwarded to re-sheath the device 1102 until the physician feels a resistance to movement indicating that the clot has been pinched in the device. The microcatheter 1103, device 1102 and clot 1101 can then be removed simultaneously while maintaining the pinch between the device and clot.

Figure 34:
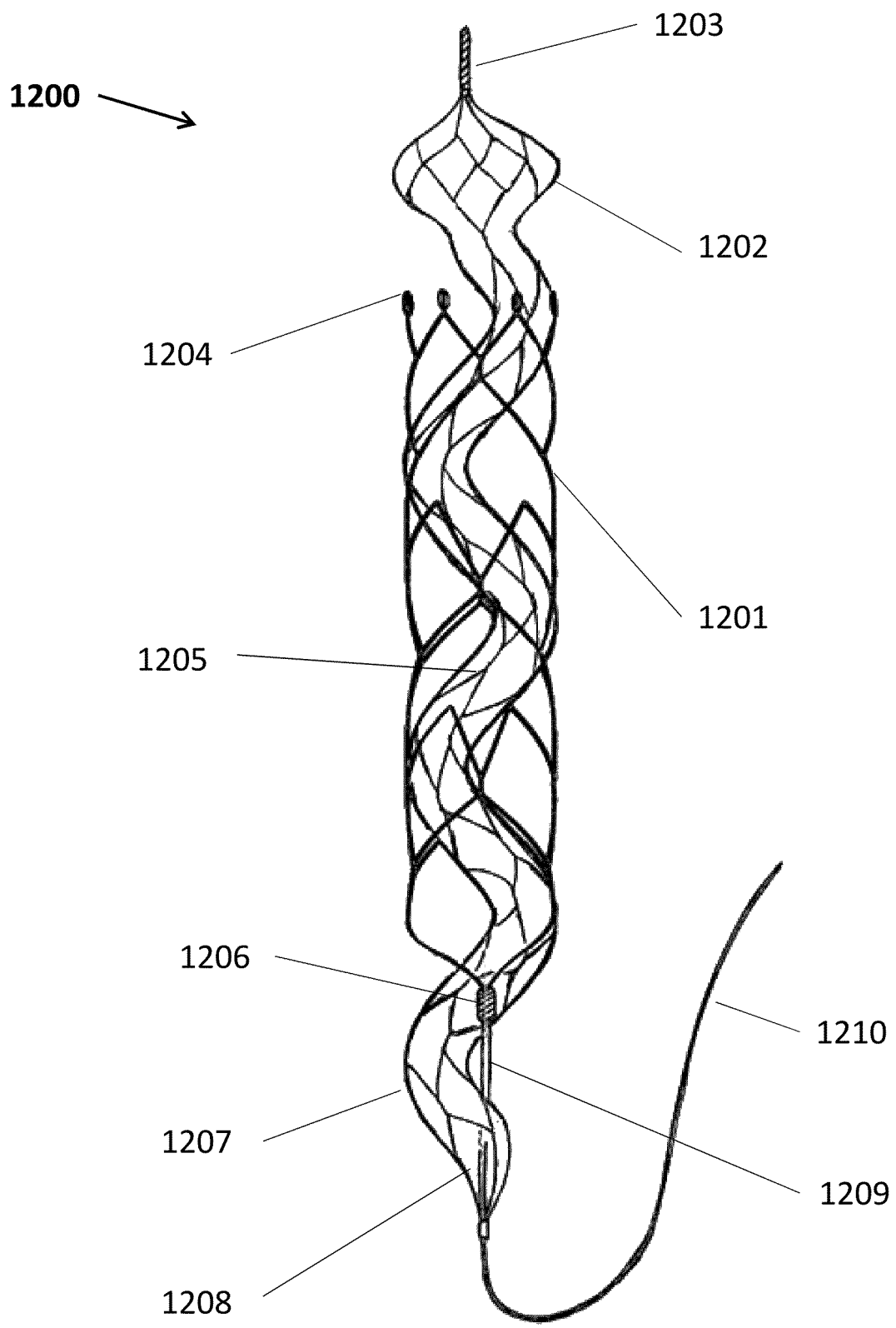
FIG. 34 is a view of another device according to the invention which is suitable for dislodgement and retention of a range of clot tyres.

The helical tubular component shown in FIGS. 29 to 33 is particularly good at generating a pinch on clots which are difficult to dislodge and retrieve from the vessel such as organised clots with a moderate to high fibrin content. FIG. 34 shows a device 1200 which can be used for dislodgement and retention of all clot types. This device 1200 incorporates a helical tubular component 1205 which can be used to generate a pinch on the clot by partial re-sheathing with the microcatheter as described previously. The outer cage component 1201 also engages with the clot on deployment providing additional grip for dislodgement and retention of the clot as the device is retracted proximally to the intermediate catheter, guide catheter or sheath. The outer cage component 1201 provides dislodgement and retention capability for a full range of clot types including soft erythrocyte rich clots and hybrid clots with varying elements. The helical component 1205 also provides additional radial force to the inner surface of the outer cage 1201 helping it to expand within the clot on deployment. The outer cage component 1201 has distal radiopaque markers 1204 to mark the distal end of the component under fluoroscopy. The radiopaque markers 1204 would typically consist of wire coils, rivets or inserts produced from Platinum, Tungsten, Gold or a similar radiopaque element.

The outer cage 1201 is connected to the proximal shaft 1210 in this configuration by a proximal strut 1209. This strut 1209 has minimal impact on the pinch performance of the helical component 1205 and can be positioned inside or outside of the proximal section of the helical tube 1207. To generate a pinch on the clot with this device, it can be partially re-sheathed with a microcatheter, diagnostic or intermediate catheter until the physician feels a resistance to pushing the catheter any further distal over the device. At this point the physician knows he has a successful pinch and the catheter and device can be removed with the clot as a unit. If no resistance is felt or a pinch is not generated then the device 1200 can be retrieved as a standard stent retriever to retrieve the clot to the access catheter. The radiopaque marker 1206 is visible under fluoroscopy and is an indicator to the physician on when to retrieve the device as a standard stent retriever, i.e. re-sheath the device with the microcatheter (not shown) until a definite resistance (pinch) is felt or until the tip of the microcatheter is aligned with marker 1206. Then retrieve the device as per standard procedure.

This device 1200 also incorporates a fragment protection feature 1202 to capture clot fragments or emboli that may be generated during the clot dislodgement and retrieval. In this configuration the fragment protection feature 1202 is an integral part of the helical component 1205 and is positioned distal to the outer cage component 1201 when fully expanded. A distal radiopaque tip 1203 is connected to the end of the fragment protection feature 1202.

Figure 35A:
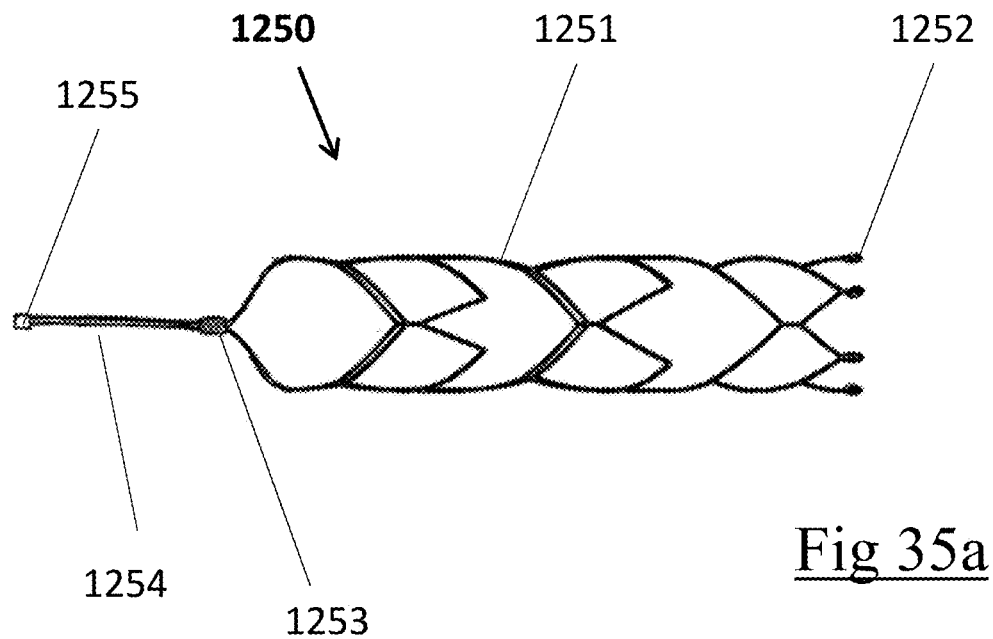
FIGS. 35a and 35b illustrate the outer cage component (FIG. 35a) and the helical component (FIG. 35b) of the device of FIG. 34.
Figure 35B:
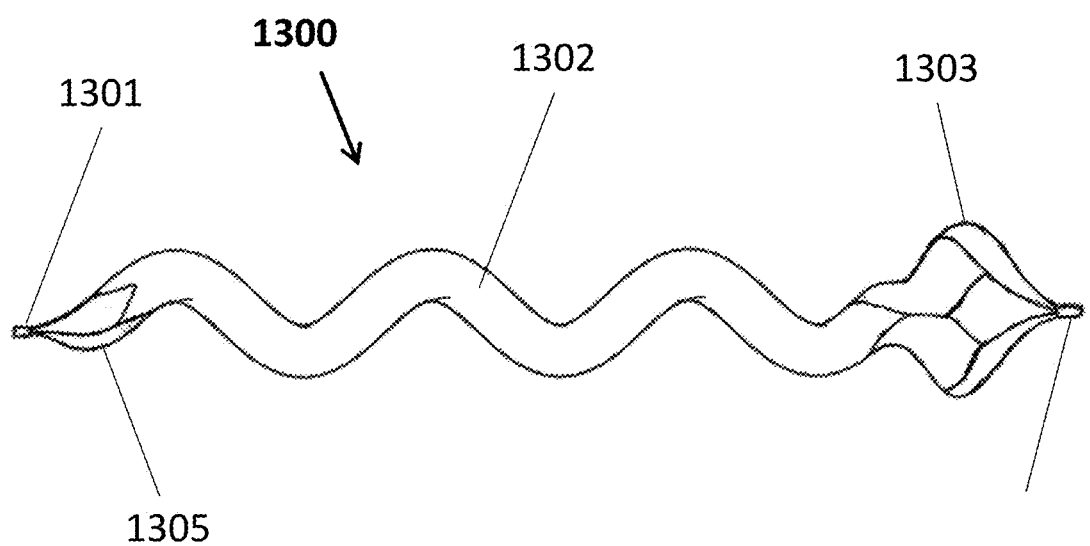

For additional clarity the outer cage component 1201 and helical component 1205 shown in the device assembly 1200 in FIG. 34 are illustrated separately in FIGS. 35a and 35b. The outer cage component 1250 in FIG. 35a has a mid-section construction in this configuration similar to that described in our WO2014/139845A, the entire contents of which are incorporated herein by reference. Distal markers 1252 are connected to the distal crowns of this section for visibility under fluoroscopy and radiopaque marker 1253 is positioned on the elongated proximal strut 1254. The radiopaque marker 1253 can be formed from a coil of radiopaque material and can be bonded, welded or soldered in place. Alternatively it can be formed from a ring of radiopaque material and be radially crimped, or formed from a flat sheet and be riveted in an eyelet on the strut. The proximal collar 1255 can be used to assemble the outer cage component 1250 and the helical tube component 1300 (shown in FIG. 35b) to the proximal shaft of the device (not shown).

FIG. 35b illustrates the helical component 1300 that is included in the assembly 1200 in FIG. 34. For clarity no strut details are shown along the body section 1302 of the component 1300 in this image. Proximal struts 1305 and the proximal collar 1301 used for device assembly are shown. The fragment protection section 1303 and the distal radiopaque marker 1304 are also shown. In this configuration the body section 1302 has a fixed diameter along its length, however in other configurations (not shown) the diameter may increase or decrease along the length. Similarly in other configurations the helical diameter and pitch may vary along the length or the component may have a combination of straight and helical sections. In addition to the pinch capability of this component, it also provides inner channel functionality such as; immediate restoration of blood flow on deployment, breaking the pressure gradient across the clot, facilitating contrast flow and distal visualisation and acting as an aspiration channel for distal emboli. The strut and crown pattern of the device 1300 may vary along the length of the body section 1302 so that the proximal portion provides a pinch capability while the mid and distal portions are more densely scaffolded to provide inner channel functionality.

Figure 36:
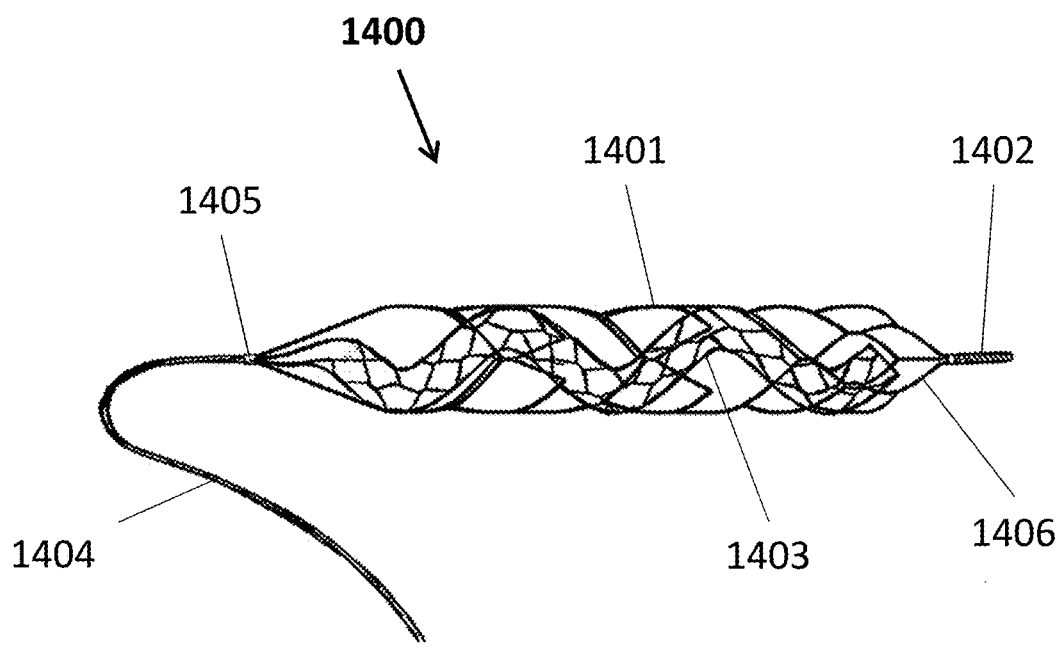
FIG. 36 is a view of another device of the invention which comprises an inner helical component and an outer cage.

Another embodiment of the invention is shown in FIG. 36. This device 1400 is also an assembly of an inner helical tubular component 1403 and an outer cage 1401. In this configuration the fragment protection feature 1406 is integral to the outer cage 1401. The outer cage 1401 and the helical component 1403 are connected to the proximal shaft 1404 at the proximal joint 1405. The distal radiopaque tip 1402 is joined to the outer cage 1401 in this assembly.

Figure 37:
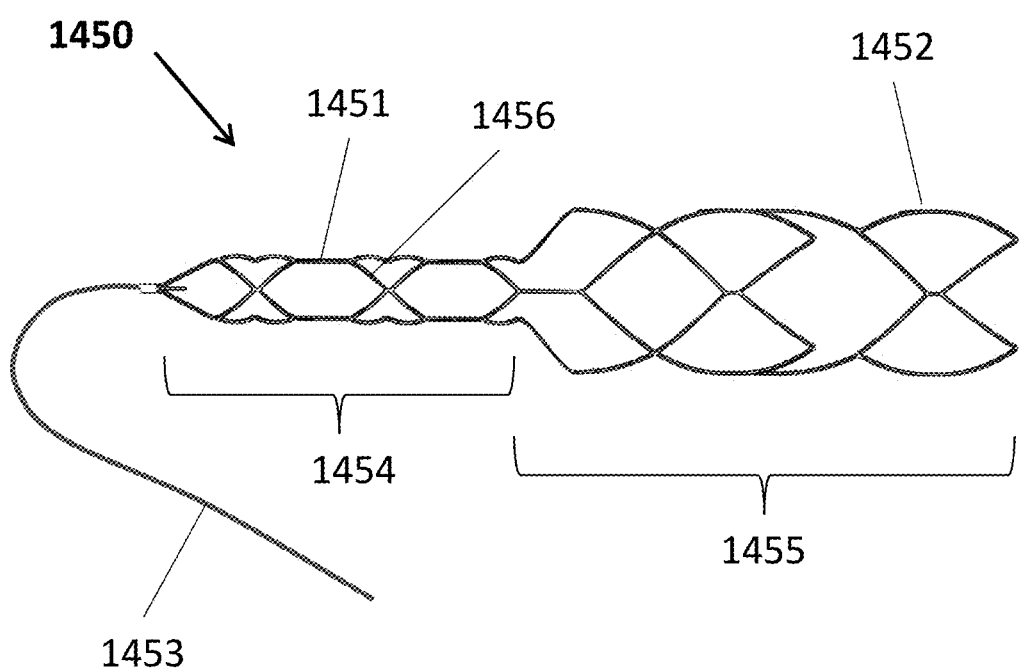
FIG. 37 illustrates another device according to the invention in which a proximal section is configured to pinch the clot when partially re-sheathed by a microcatheter.

FIG. 37 shows another embodiment of the device shown in FIG. 7a. In this device 1450, the proximal section 1451 is configured to pinch the clot when partially re-sheathed by the microcatheter. As before the proximal struts 1456 have large opening angles and the cell size promotes clot protrusion to facilitate pinching between the microcatheter and the device 1450 during re-sheathing. The mid-section 1452 is configured to expand to a larger diameter than the proximal section to provide clot grip and retention during retraction of the clot past vessel bends and branches. The proximal 1451 and mid sections 1452 have different strut lengths and cut patterns and hence different radial force characteristics. In one embodiment the radial force of the proximal section 1454 is larger than the corresponding radial force of the mid-section 1455, for a fixed deployment diameter (e.g. 1.0 mm), while in another embodiment the radial force of the mid-section 1452 is larger than the radial force of the proximal section 1451 for the same deployment diameter.

Figure 38:
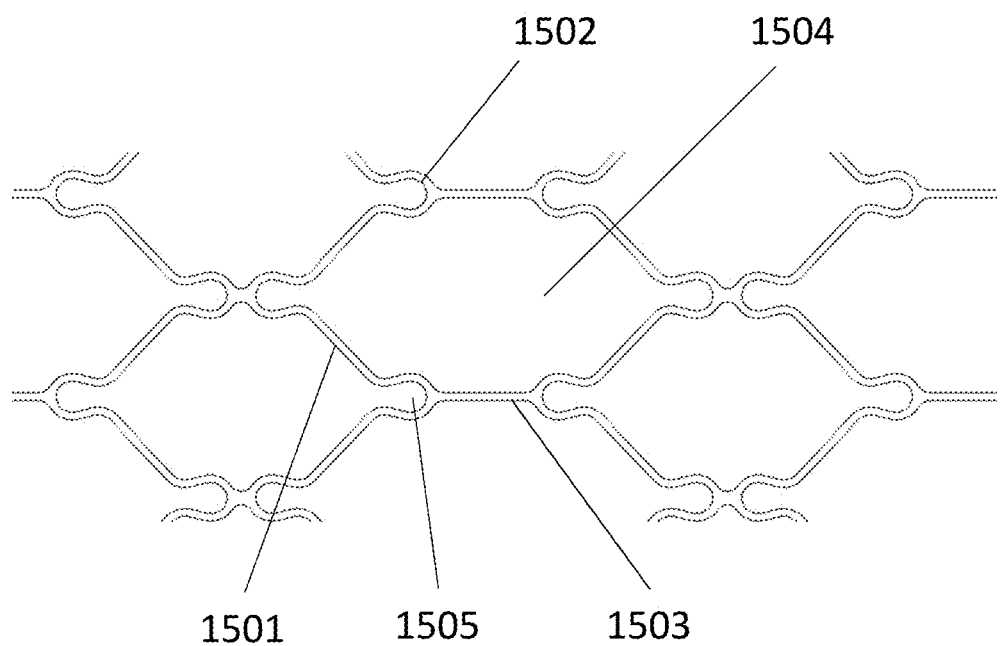

FIG. 38 illustrates a typical strut cut pattern of the pinch portion of any of the devices detailed in this invention. The struts 1501 have a large opening angle relative to the longitudinal vessel axis which promotes improved clot grip as the greater the angle of the strut to the direction of movement, the greater the ability of the strut to grip the clot rather than slide past it. Similarly the inner diameter of the crown 1502 is increased to also improve clot grip by maximising the length of the crown that is near perpendicular to the direction of travel within the clot. The length of the strut connector 1503 increases the total cell area 1504 to provide rings of cells in the device with low radial force and low strut surface area to promote clot embedding and protrusion into these cells. When the device is re-sheathed with the microcatheter the protruding clot is pushed against the struts 1501 and into the crown space 1505 trapping it and pinching it in position.

Figure 39:
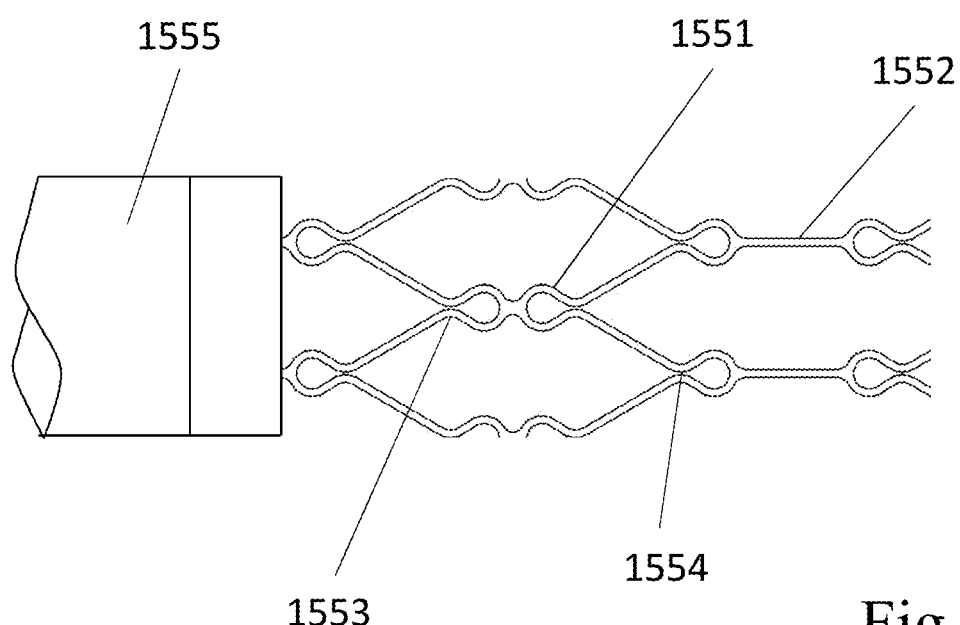

Another embodiment of the device cut pattern is shown in FIG. 39. In this configuration the strut shape and bend angle 1553 adjacent to the crown 1551 is sized so that on re-sheathing with the microcatheter 1555, the adjoining struts close together 1554 creating another pinch point to help grip the clot that is protruding into the cell area (not shown).

Figure 40:
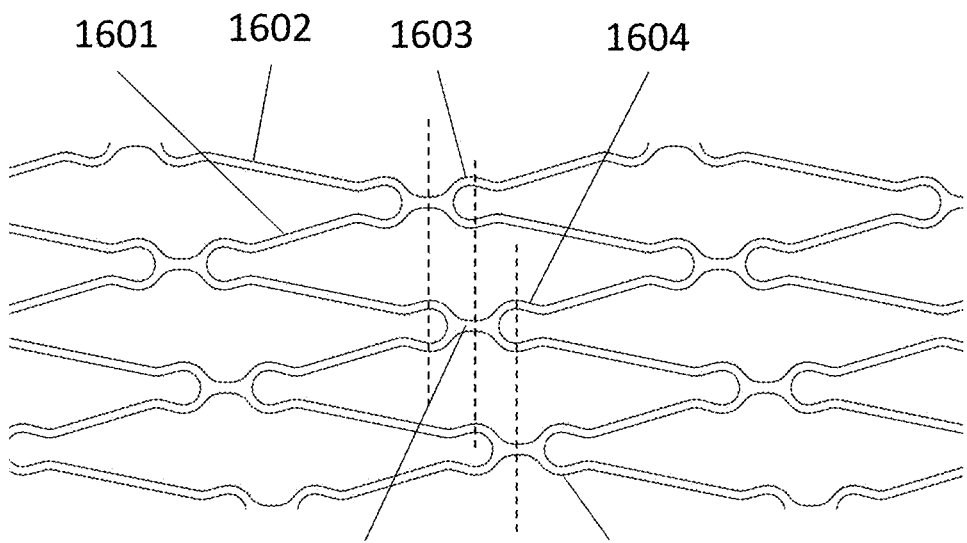

As described in FIG. 38, the larger the crown inner diameter in the cut pattern the longer the portion of the crown which is near perpendicular to the longitudinal axis of the vessel (and the direction of clot movement), the better the clot dislodgement capability. FIG. 40 shows a crown configuration which allows the crown diameter to be maximized while enabling the device to be wrapped into the loaded configuration for delivery through the microcatheter to the target vessel location. To minimize the wrapped diameter, the crowns 1603, 1604 and 1605 are offset along the longitudinal axis so that in the collapsed configuration the crowns fit into the space either side of the short connector, for example 1606. To generate this crown offset the adjoining struts 1601 and 1602 have different lengths.

Figure 41:
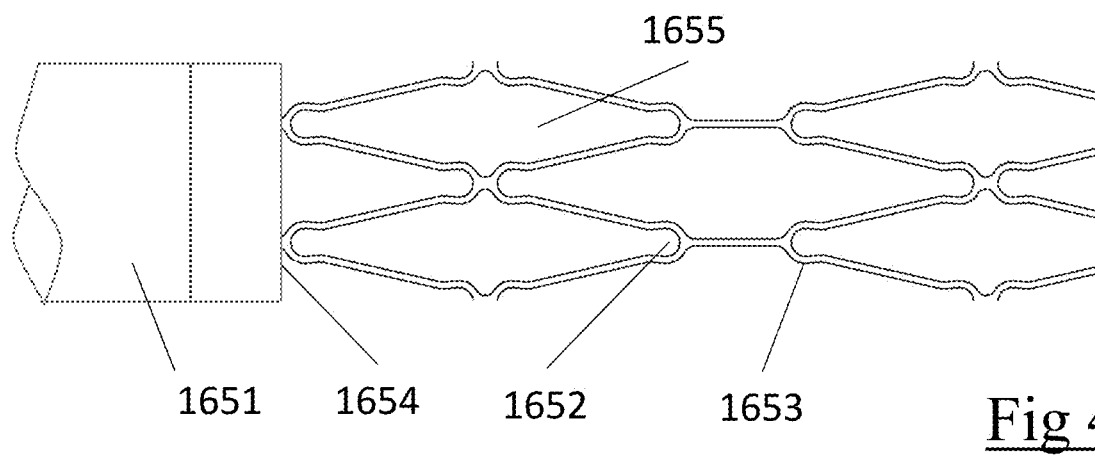
Figure 42:
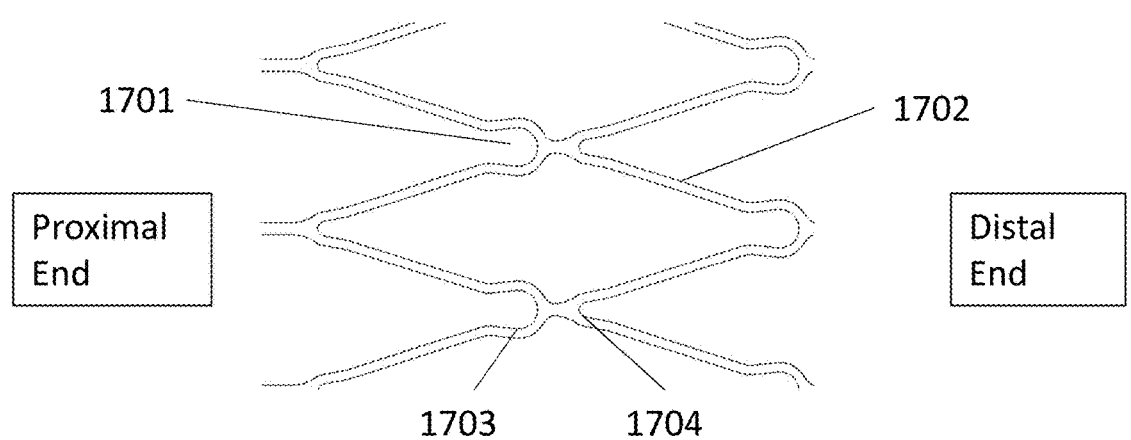

FIG. 41 shows another embodiment of the device where the cut pattern is configured so that the crown 1653 maintains its full diameter during re-sheathing by the microcatheter 1651 so that the maximum quantity of clot can be pushed from the cell 1655 into the crown space 1652 by the microcatheter tip 1654 creating a pinch. FIG. 42 shows an embodiment of the cut pattern where the proximal facing crowns 1703 are similar to those described in FIG. 41 where the crown space 1701 is maximised for improved clot pinching. In this configuration the distal facing crown diameter 1704 is reduced as the crown is not required for clot pinching and the reduced diameter may facilitate a lower re-sheathing force and increased radial force in the adjacent struts 1702.

Figure 43:
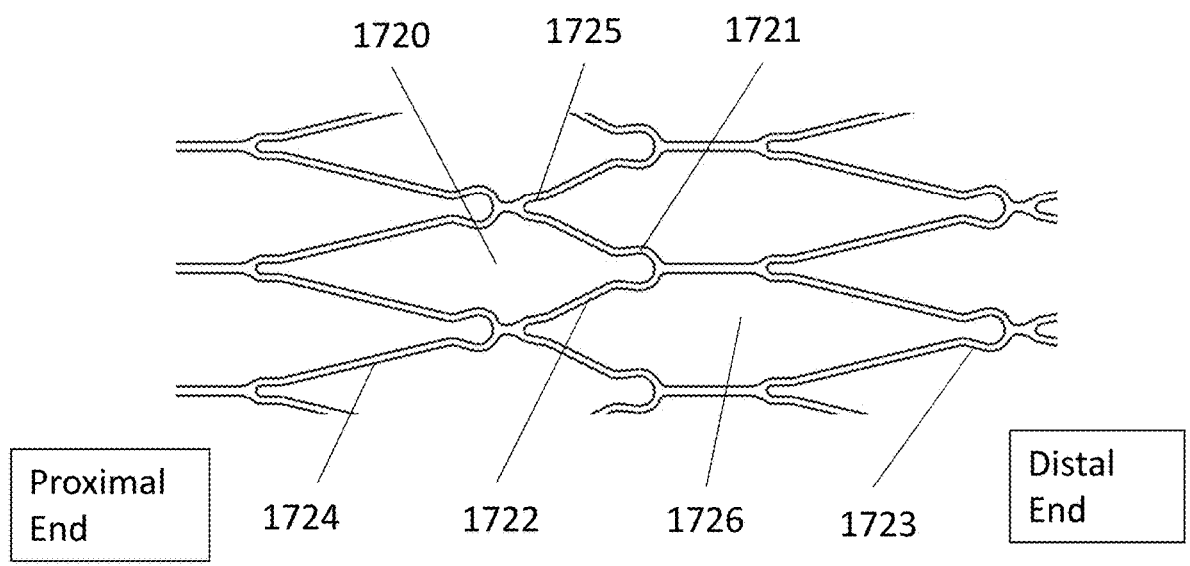

FIG. 43 shows an embodiment of the device where the proximal facing crowns 1721, 1723 have a larger diameter than the distal facing crowns 1725 for improved clot pinching as detailed in FIG. 42. The alternating rings of cells along the longitudinal axis of this device have different areas with cell 1726 having a larger area than 1720. Hence more clot is likely to embed and protrude into cell 1726. The clot protruding into the cell 1726 will get pushed towards crown 1723 by the microcatheter when re-sheathing. To ensure this re-sheathing is smooth with good tactile feedback to the physician, the length of strut 1724 is increased to reduce the feeling of 'bumping' as the catheter goes from low radial force segments to high radial force segments. In addition the length of strut 1722 is shortened to increase radial force in the ring of struts which is supporting crown 1723. This keeps the crown 1723 expanded for longer during re-sheathing by the microcatheter increasing the pinch effectiveness.

Figure 44A:
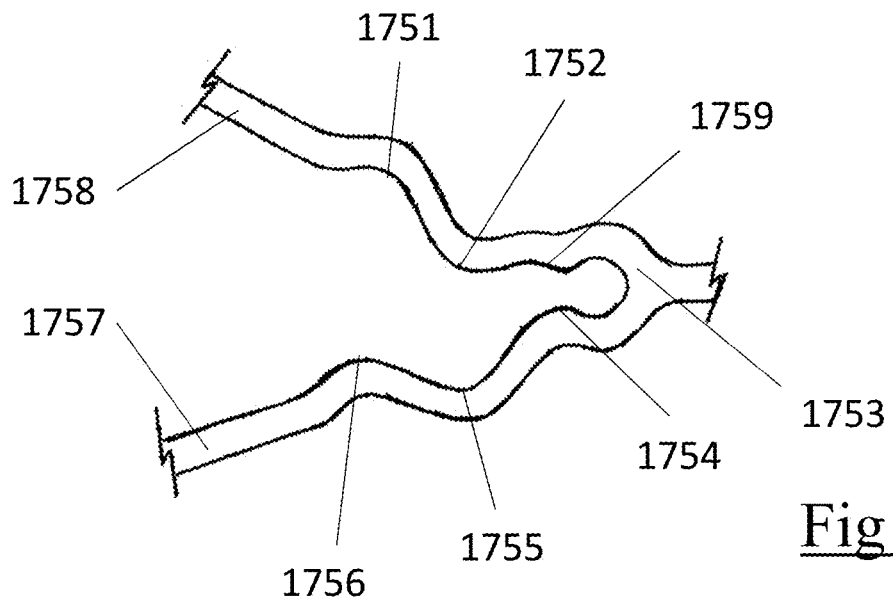
Figure 44B:
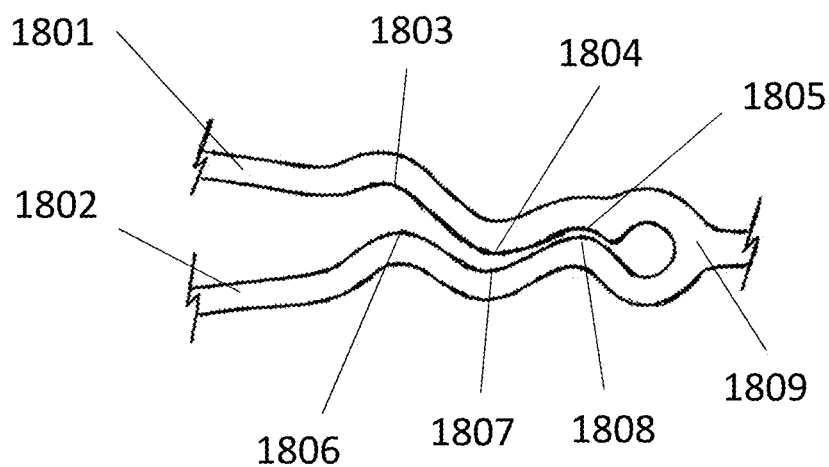
Figure 44C:
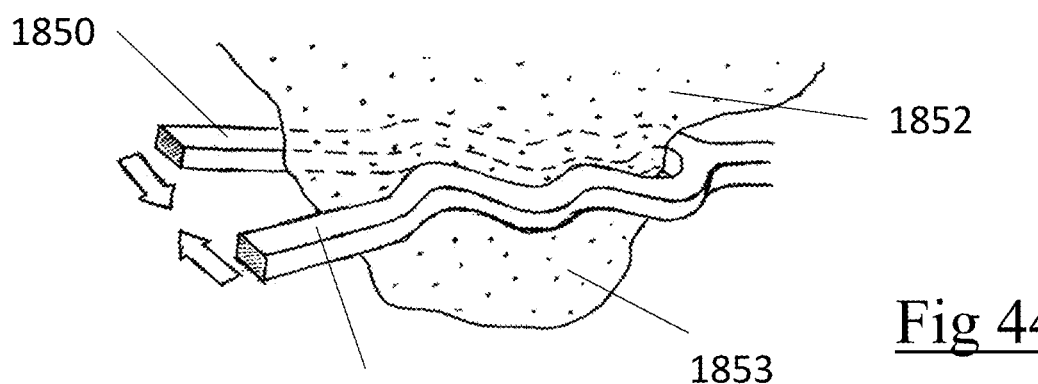

FIGS. 44*a-c* show a strut/crown configuration which promotes clot pinching along the length of the strut. FIG. 44*a* shows the struts 1757 and 1758 in the freely expanded configuration. Strut 1758 is produced so that it contains a series of bends 1751, 1752 and 1759 approaching the crown 1753. Similarly strut 1757 contains a series of matching bends 1754, 1755 and 1756. As the device is re-sheathed in the microcatheter, the diameter of the device reduces and the struts move closer together. FIG. 44*b* illustrates that as the diameter reduces, the bends in the struts interlock creating pinch points such as between points 1808 and 1805, and between 1804 and 1807. This helps to grip the protruding clot which is embedded between the two struts as shown in FIG. 44*c*. In FIG. 44*c* part of the clot 1852 protrudes into the cell between the struts. As the device is re-sheathed by the microcatheter (not shown), struts 1850 and 1851 move closer together generating a pinch on the protruding clot 1853. This clot pinching improves device efficacy with enhanced clot dislodgement capability and safe clot retrieval into the access catheter.

Figure 45:
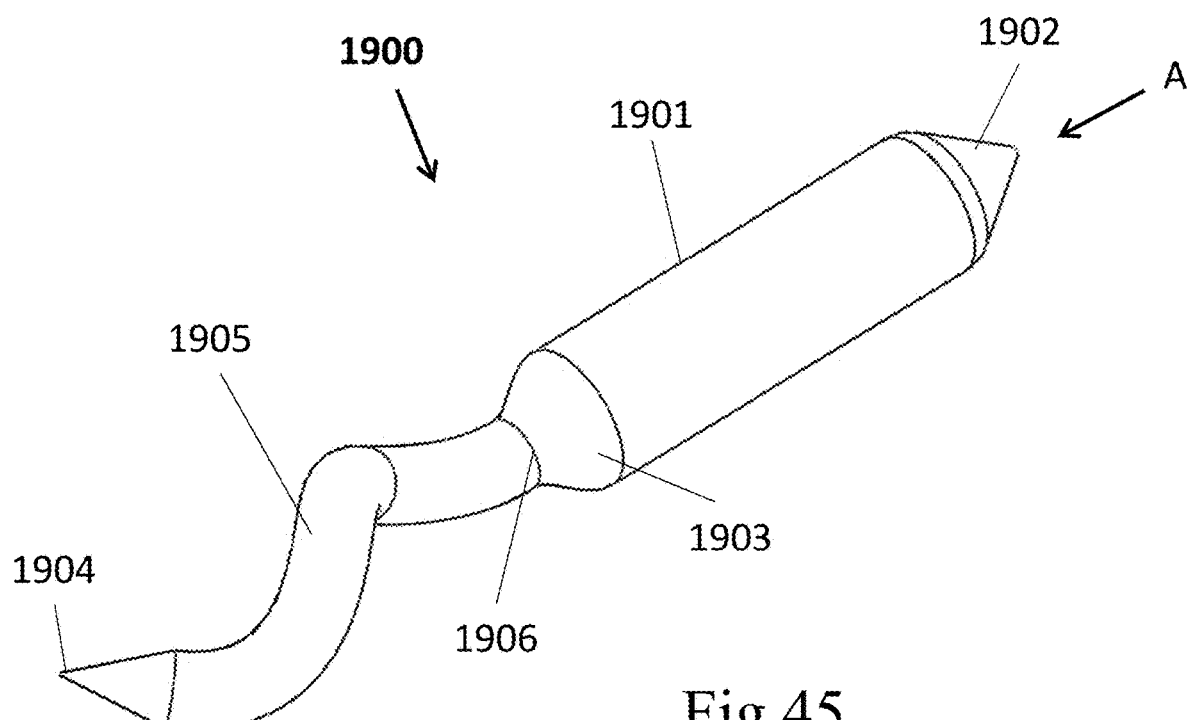
FIG. 45 is an illustration of the profile and the outer shape of another device of the invention.

Another embodiment of the invention is shown in FIG. 45. This figure illustrates the profile and outer shape of the device 1900 but does not show the strut pattern for clarity. In this embodiment the proximal section of the device 1905 is formed into a spiral configuration as described in FIGS. 29 to 33. This proximal section 1905 is also configured to pinch the clot when partially re-sheathed by the microcatheter. As before the struts have opening angles and crowns to facilitate clot pinching and the cell size promotes clot protrusion to further improve pinching between the microcatheter and the device during re-sheathing. The body section 1901 is configured to expand in a cylindrical or uniform shape to provide clot grip and retention during retraction of the clot past vessel bends and branches. The body section is also particularly suited to the grip and retention of softer clot with red blood cell content in the range of 30-100% but particularly clots with red blood cell content greater than 50%. In this configuration the device is effective at dislodging and retaining fibrin rich and red blood cell rich clots by gripping the fibrin rich clot by partial re-sheathing with the microcatheter over the proximal section 1905, while gripping and retaining the softer or heterogeneous clots by the body section 1901. The device 1900 shown in this figure is connected to a proximal shaft (not shown) at the proximal joint 1904 and has a fragment protection zone 1902. The proximal spiral section 1905 is connected to the body section 1901 at 1906. This connection may be centred and be concentric with the body section or may be eccentric, for example aligning with the outer surface of the body section. The flared section 1903 between the proximal tubular section and the body section can include large cell openings to facilitate clot migrating into the body section for improved retention and fragment protection.

Figure 46:
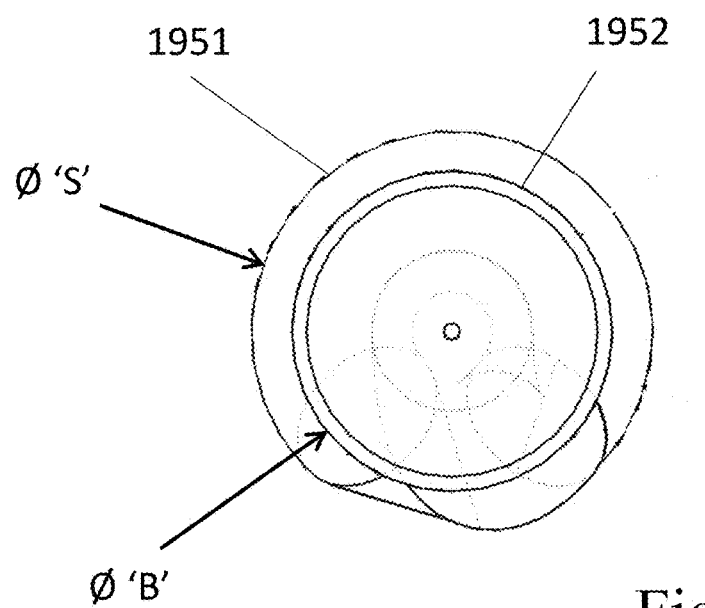
FIG. 46 is an end view of the device of FIG. 45 when viewed from the direction of arrow A in FIG. 45.

FIG. 46 shows an end view of the device 1900 illustrated in FIG. 45 when viewed from direction 'A' as shown. In this figure the spiral outer surface 1951 has a larger diameter (Ø'S') than the body section diameter 1952 (Ø'B'). In other embodiments (not shown) the spiral outer diameter may be equal or smaller than the body section diameter. The spiral outer diameter is typically between 2.0 and 8.0 mm diameter and in the preferred embodiment is between 4.0 and 6.0 mm. The body section diameter can vary from 1.0 to 8.0 mm and in the preferred embodiment is between 3.0 and 6.0 mm. The body section is shown in a cylindrical configuration in this embodiment however this section may also be formed into a spiral or curved shape with a different pitch, tubing diameter and spiral diameter to the proximal section.

Figure 47:
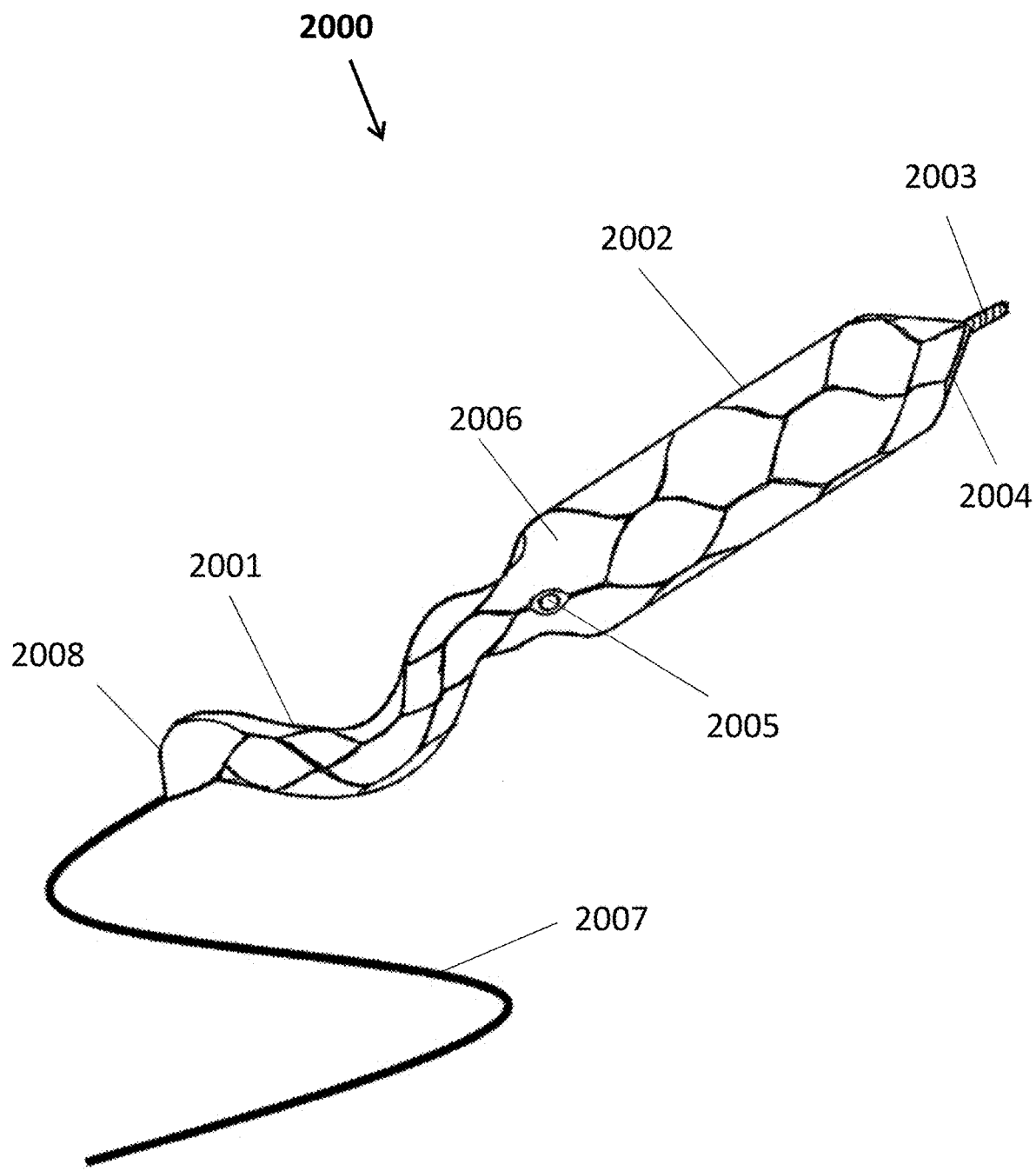
FIG. 47 shows a device of similar shape to the device of FIG. 45 with additional strut and connection details.

The embodiment 2000 shown in FIG. 47 has a similar shape to the device illustrated in FIGS. 45 and 46 with additional strut and construction details. This embodiment is shown connected to a proximal shaft 2007 by the proximal struts 2008. The proximal section 2001 is formed in a spiral configuration and the body section 2002 is formed in a cylindrical shape. The distal end of the device forms a cone shape to provide fragment protection capabilities. A radiopaque coil or marker 2003 is added to the distal tip for visibility under fluoroscopy. An additional radiopaque marker 2005 is added to the device at or near the transition from the spiral section to the body section. This marker 2005 highlights the end of the spiral section 2001 and can be used to distinguish the optimum point to stop re-sheathing with the microcatheter. This radiopaque marker may also be used to align the device with the proximal face of the clot for red blood cell rich clots. Similarly a radiopaque coil (not shown) on the distal end of the shaft 2007 can be used to align the spiral pinch section 2001 with the proximal face of fibrin rich clots. The proximal spiral section is typically 5 to 30 mm in length and in the preferred embodiment is between 8 and 15 mm in length. Additional radiopaque markers can be added along the spiral section to provide increased visual feedback and clarity for the re-sheathing process with the microcatheter. FIG. 47 also illustrates the cell openings 2006 at the diameter transition from the spiral tube to the body section which are designed to facilitate clot entering partially or fully inside the body section 2002.

Figure 48:
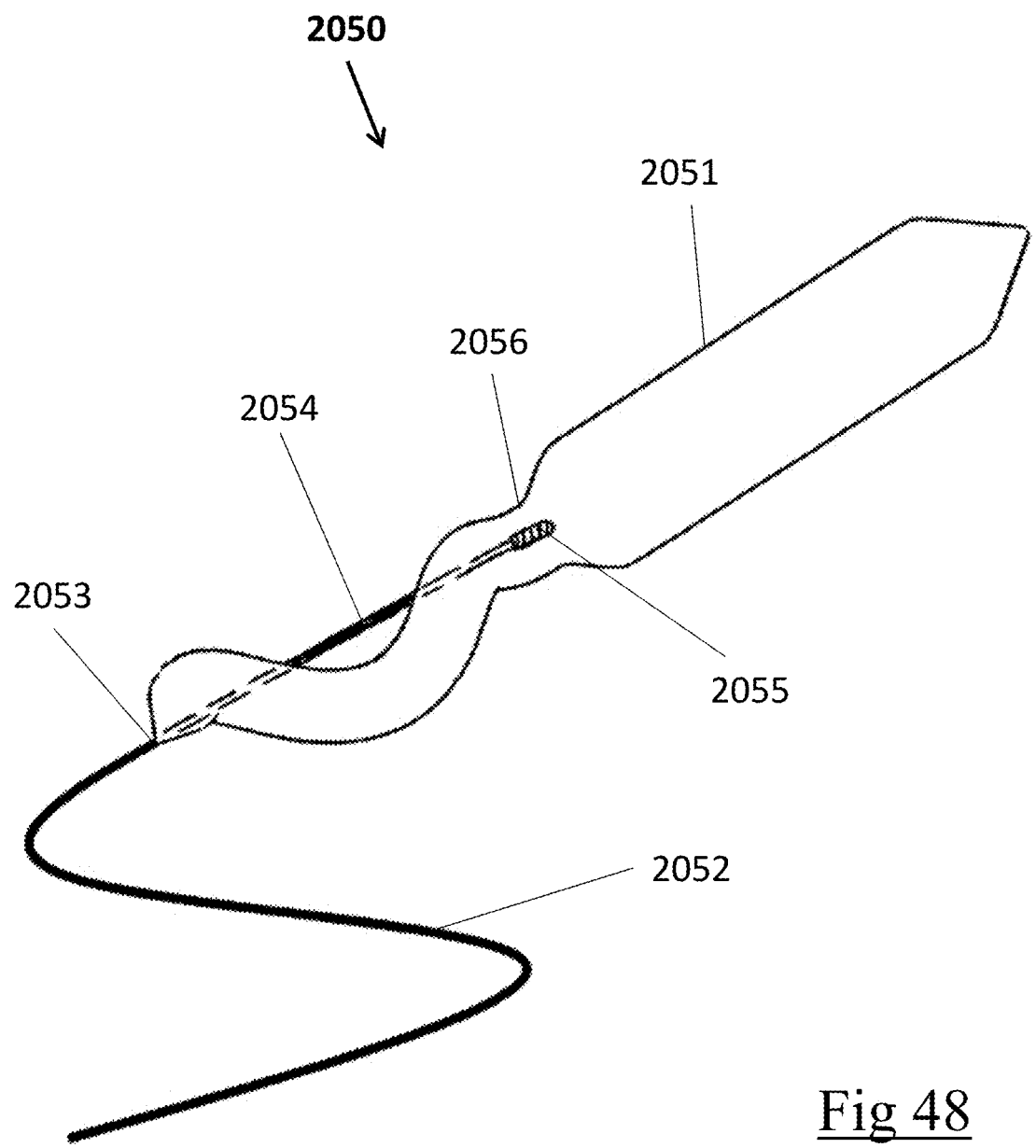
FIG. 48 illustrates another embodiment of the device in which an outer shaft and shape of spiral and body sections are illustrated.

FIG. 48 shows another embodiment 2050 of the device where only the shaft 2052 and the outer shape of the spiral and body sections 2051 are shown. In this embodiment the radiopaque marker 2055 which distinguishes the end of the spiral section 2056 is mounted on an extension 2054 to the proximal shaft 2052. This shaft extension 2054 continues distal of the proximal joint 2053 which connects the spiral section to the shaft 2052.

Figure 49A:
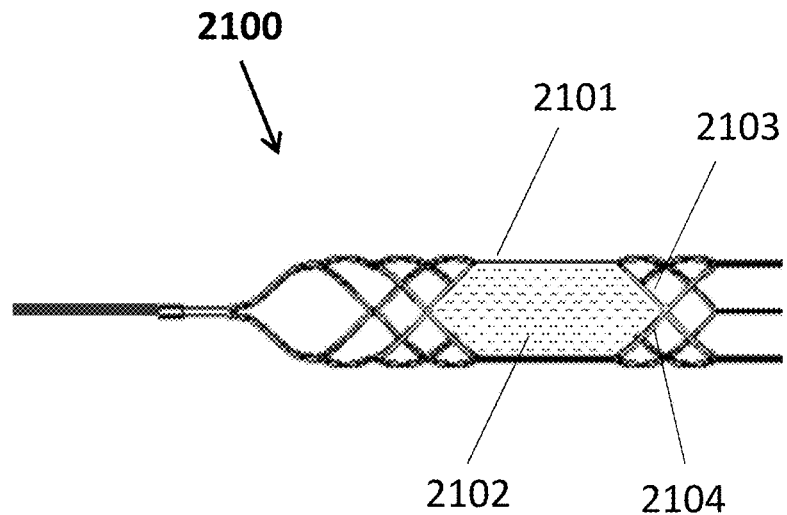
FIG. 49a is a partial plan view of the device of FIGS. 6a to 6d.
Figure 49B:
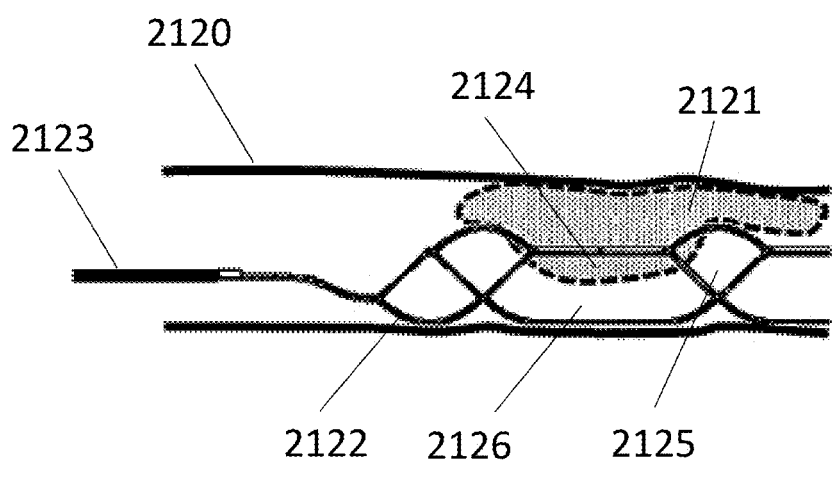
FIGS. 49b and 49c illustrate the device of FIG. 49a, in use.

FIG. 49a shows a partial plan view of the embodiment 2100 detailed previously in FIGS. 6a-d and illustrates the large cell area 2102 which promotes clot protrusion into the device so that it can be pinned against struts 2103 and 2104 when the device is re-sheathed with a microcatheter. In FIG. 49b the device 2122 is shown deployed in a clot 2121 which is located in an arterial vessel 2120. The device 2122 is connected to a proximal shaft 2123. On deployment of the device, the ring of struts and cells 2125 embed in the clot, while the clot section 2124 positioned over the large open cell section 2126 protrudes into the device. The large open cell section promotes clot protrusion into the device, minimising clot compression and subsequent increase in friction with the vessel wall 2120.

Figure 49C:
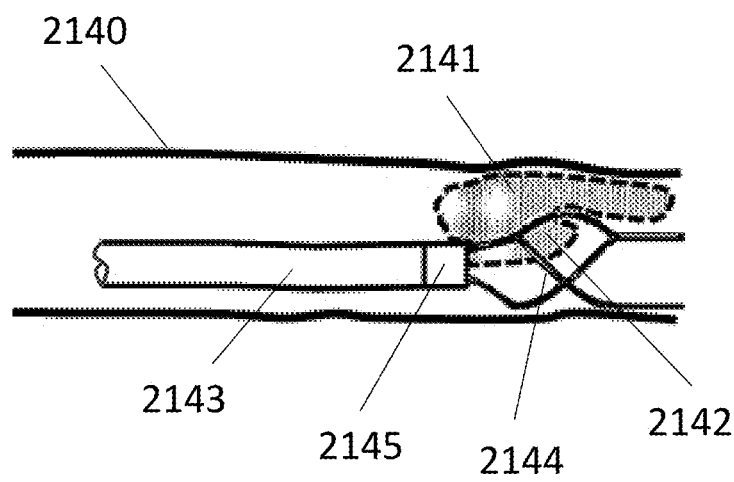

FIG. 49c illustrates how the protruding section 2142 of the clot 2141 is pushed against the ring of struts and crowns 2144 by the catheter tip 2145 to generate the grip on the clot to facilitate dislodgement and retrieval from the vasculature.

Figure 50A:
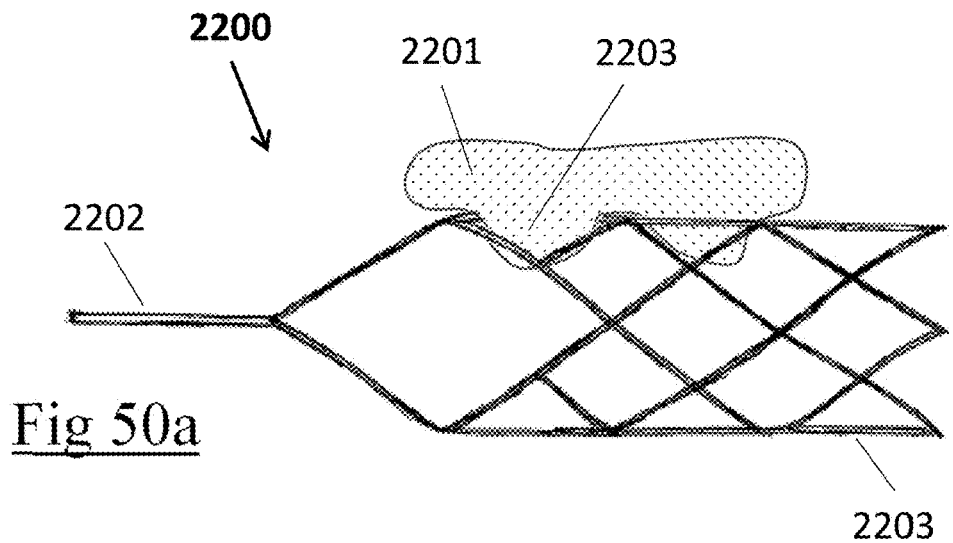
FIGS. 50a to c illustrate a prior art stent retriever type device being re-sheathed with a microcatheter.
Figure 50B:
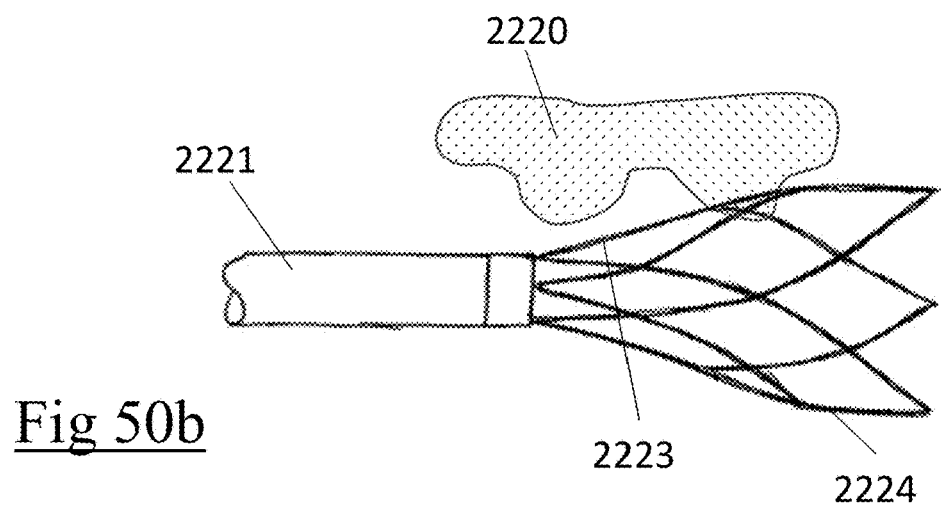
Figure 50C:
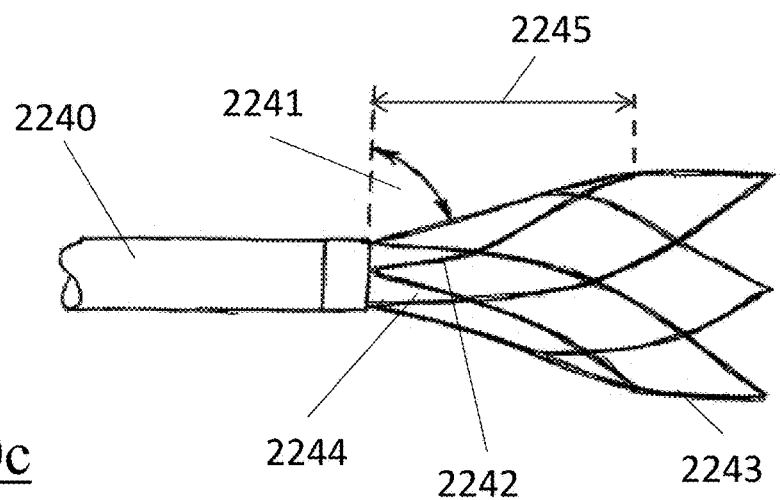

The invention disclosed here is more effective and reliable at generating a clot grip and pinch than existing stent retriever technology when re-sheathed with a catheter. FIG. 50a-c illustrates what happens when an existing stent retriever device 2200 (prior art) is re-sheathed with a microcatheter. FIG. 50a shows stent retriever 2203 deployed in a clot 2201. Strut embedding occurs in the clot 2201 and some clot protrudes into the open cells 2203. A typical stent retriever has an outer diameter in the range of 4 to 6 mm and as the device 2224 is re-sheathed as shown in FIG. 50b, it contracts and pulls away from the clot 2220. Therefore as the microcatheter 2221 is advanced, the struts 2223 which were embedded in the clot 2220 pull away from the clot surface and the clot protrusion in the cell is lost allowing the microcatheter to advance fully, re-sheathing the device underneath the clot. FIG. 50c shows how the strut length 2242 and crown opening angle 2244 dictate the re-sheathing angle 2241 of the device, as it is re-sheathed by catheter 2240. The greater this angle 2241 from the vertical, the more likely the device struts will pull away from the surface of the clot during re-sheathing. The length 2245 is the distance from the catheter tip that the device diameter starts to contract as the catheter is forwarded. This length increases as the re-sheathing angle increases (from vertical), reducing the contact of the device struts with the clot.

Figure 51A:
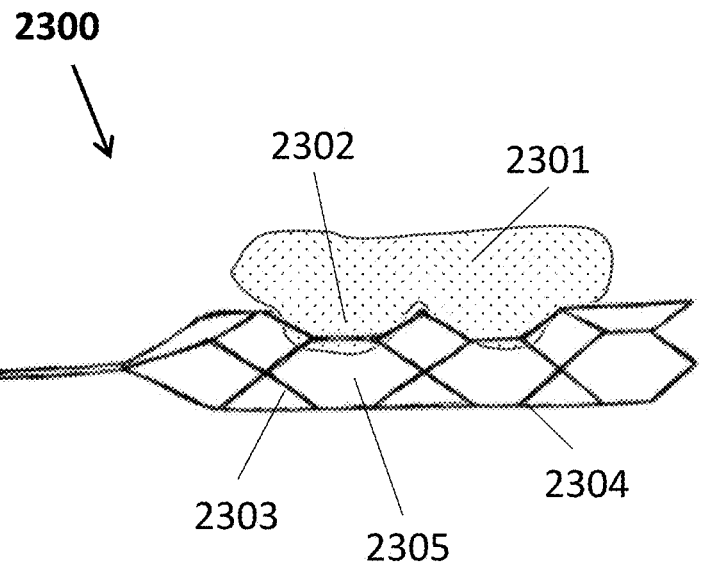
FIGS. 51a to c show a device of the invention deployed in a clot.
Figure 51B:
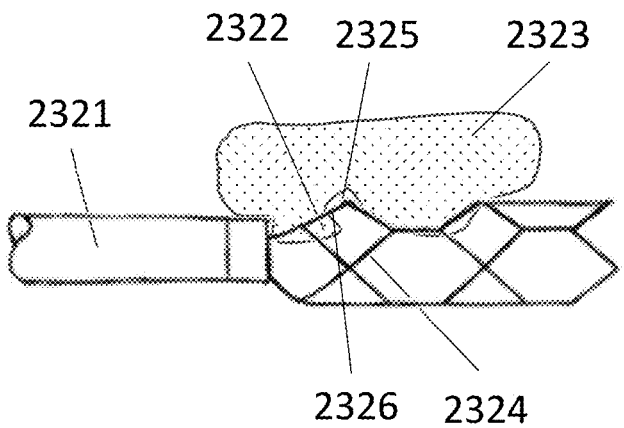
Figure 51C:
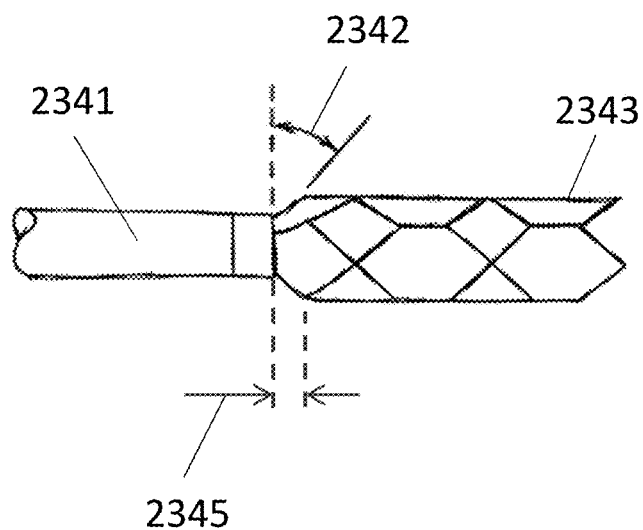

In comparison to FIGS. 50a-c of existing stent retriever technology, FIGS. 51a-c show an embodiment of the invention deployed in a clot. FIG. 51a illustrates a device 2300, similar to that described elsewhere in this patent, deployed in a clot 2301. The rings of struts 2303 embed into the clot and the clot 2302 protrudes into the large open cells 2305. As the device is re-sheathed with a catheter as shown in FIG. 51b, the strut length, crown configuration and radial force profile along the device length maintain strut embedding in the clot and clot protrusion in the cells as the catheter tip approaches. Therefore the clot 2322 is still protruding in the device cell during the re-sheathing process and is pushed against the adjacent strut 2326 and crown 2325, pinching it in position. Crown 2325 is also supported by the ring of struts 2324 to ensure it stays expanded and embedded in the clot for longer during the re-sheathing process. This performance characteristic is reflected in the reduced re-sheathing angle (from vertical) shown in FIG. 51c and the significantly reduced length 2345 showing that the device diameter does not contract except in the immediate vicinity of the catheter tip. This feature is further facilitated by the alternating higher and lower radial force profile along the device length as described previously in FIGS. 3a-d.

Figures 52A, 52B, 53:
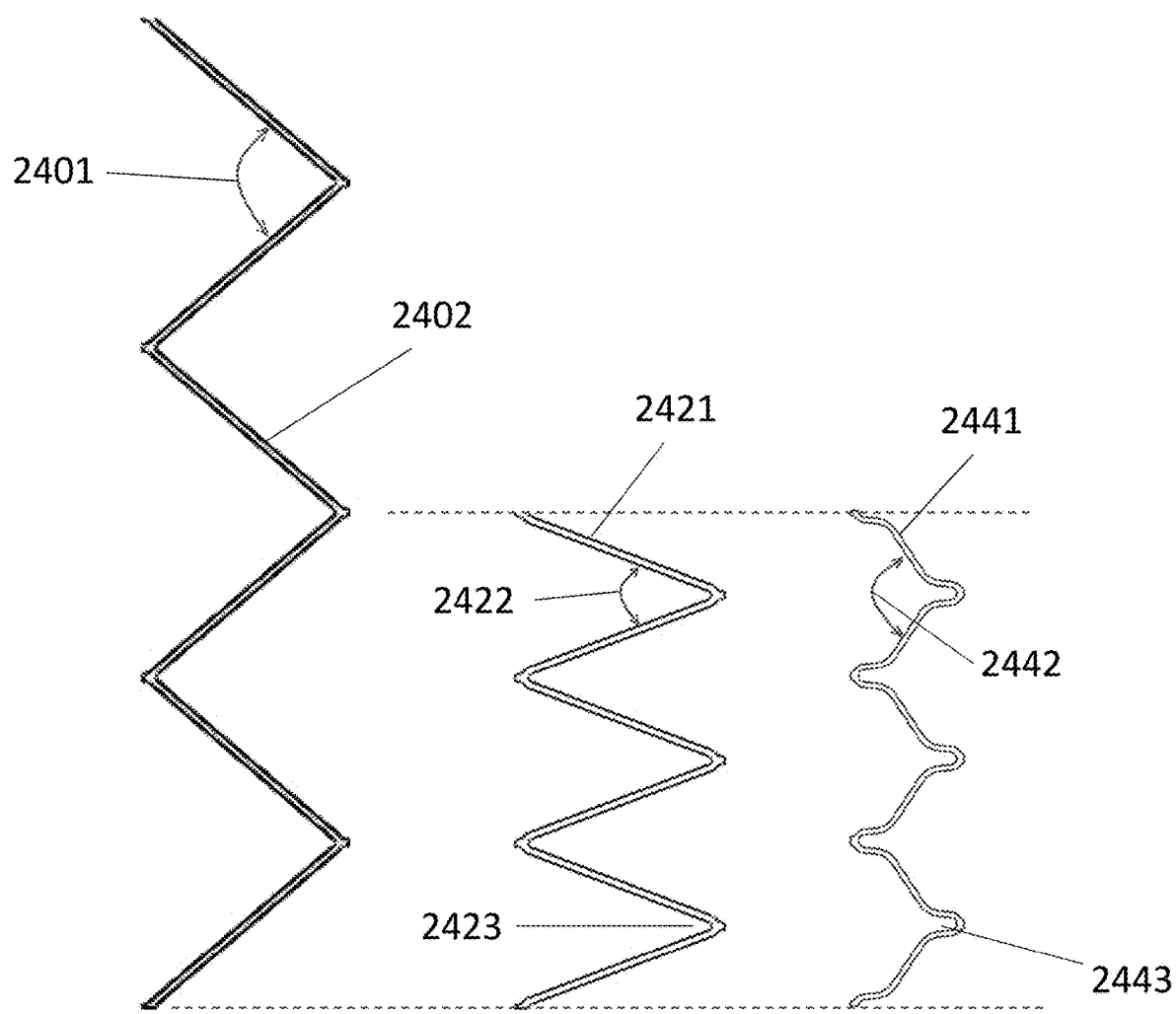
FIGS. 52a and 52b illustrate struts of a prior art stent retriever type device in an expanded (FIG. 52a) and contracted configuration (FIG. 52b)
FIG. 53 shows a strut configuration of a device of the invention.

The preferred embodiment of this device has an outer diameter of 2 to 3 mm which facilitates shorter strut lengths which allow higher crown expansion angles during the re-sheathing process than standard stent retrievers which typically expand to 4 to 6 mm. This is illustrated in FIGS. 52a and b where FIG. 52a shows the expanded struts 2402 of a 3 cell conventional stent retriever with a 4 mm outer diameter, which has been unrolled into a 2D configuration. This same device is shown in FIG. 52b when contracted to a 2 mm diameter, showing the strut length 2423 and how the crown opening angle has reduced from 2401 in FIGS. 52a to 2422 in FIG. 52b. In comparison a strut configuration of the invention is shown in FIG. 53 illustrating the large expanded angle 2442 of the struts plus the large crown ID 2443 to facilitate pinching. This device is still effective at 2 mm diameter as the clot engagement and retention is provided by pinching the clot between the microcatheter tip and the crown and struts of the device rather than pinning the clot partially or fully against the vessel wall by the device to maintain strut embedding and clot engagement.

Figure 54A:
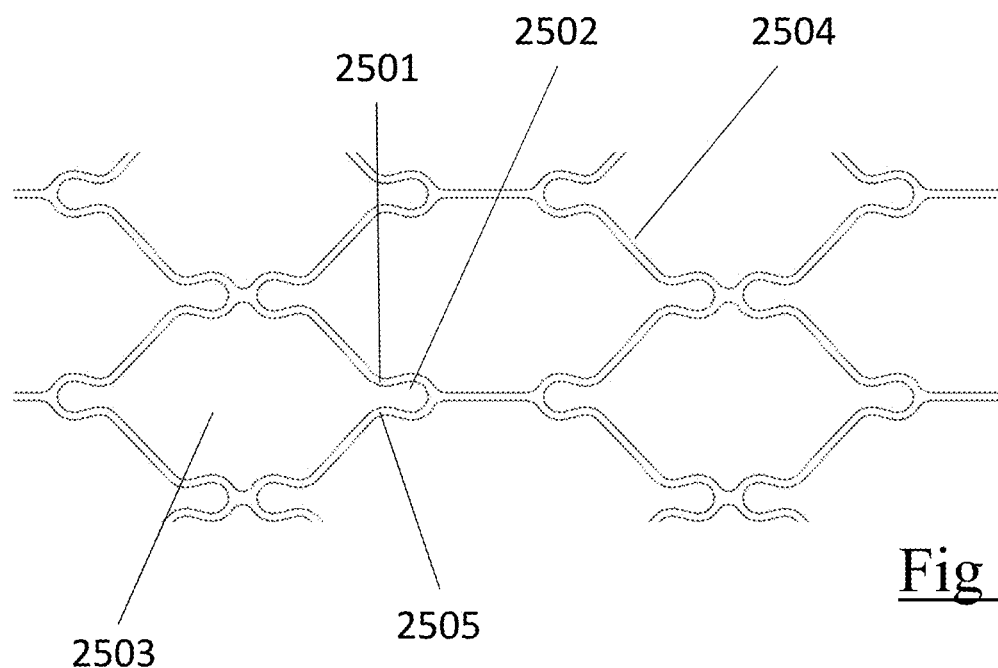
FIGS. 54a and 54b illustrates the strut configuration of a device of the invention.
Figure 54B:
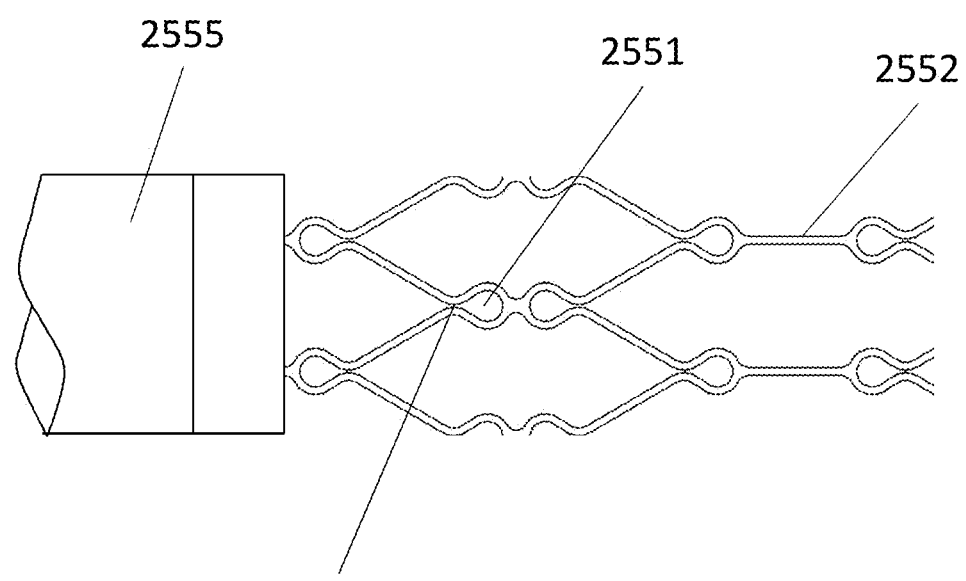
Figure 55:
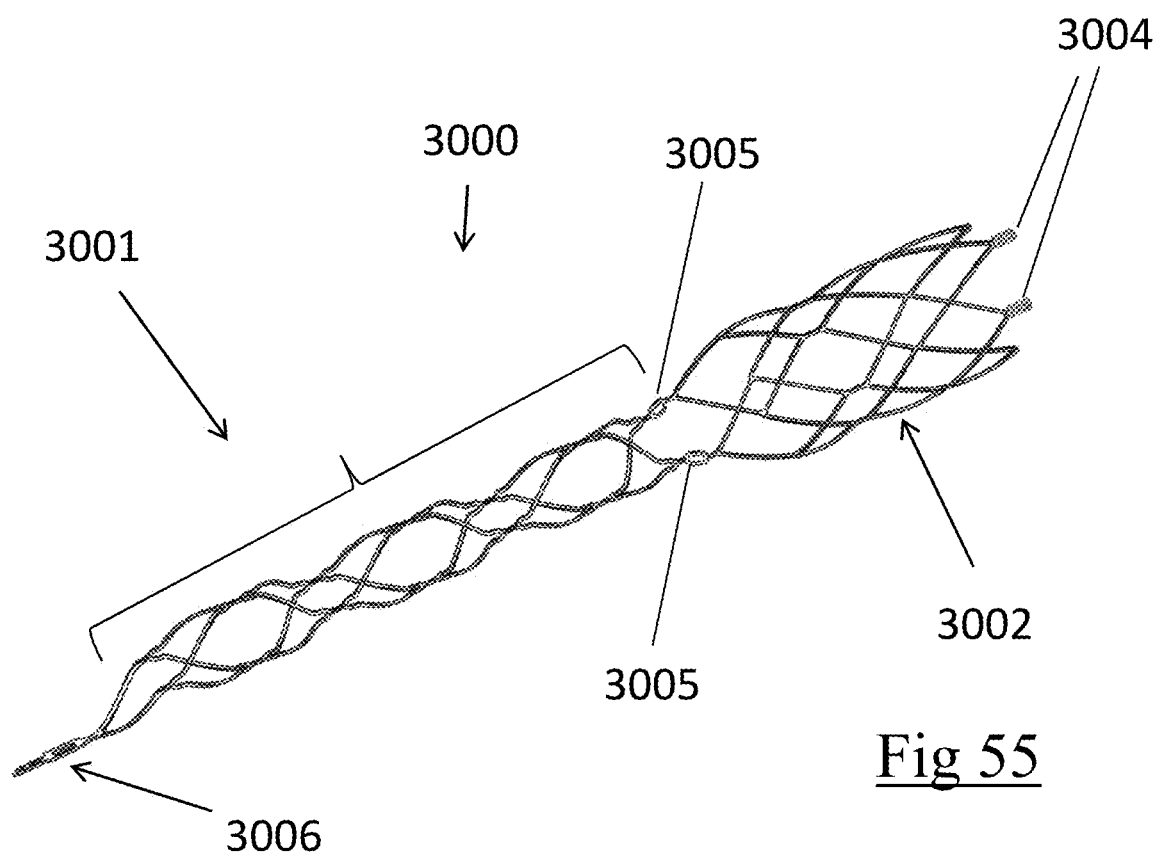
FIG. 55 is an isometric view of another device according to the invention.

The strut configuration shown in FIGS. 54a and 54b provide additional benefits to help generate a pinch and dislodge occlusive clots. The strut pattern of the device 2504 in FIG. 54a is shown unrolled into a 2D configuration. When the device 2504 is re-sheathed with a microcatheter, the outer diameter reduces causing the neck point 2505 to move towards the opposite neck point 2501. This can help grip the clot protruding in the cell 2503 and maintain the clot in this position as the microcatheter advances and pushes the clot against crown 2502, pinning it and generating a pinch grip. FIG. 54b further illustrates how the neck points 2553 close together providing additional grip on the clot (not shown) that is positioned between the microcatheter tip 2555 and the crown 2551, to facilitate pinching and also enhance the grip and retention of the clot as it is retracted past bends and branches to the access catheter.

Referring to FIGS. 55 to 58 there is illustrated another device 3000 according to the invention which has in some features which are similar to the devices described above. The device 3000 comprises a proximal pinch section 3001 and a distal section 3002 which in this case is of generally cylindrical or barrel shape having a larger diameter than the proximal section. The distal barrel section 3002 can have distal radiopaque markers which in this case comprise two platinum/tungsten coils 3004 which are attached to the distal most ends of two of the struts that form the distal barrel section 3002. Further radiopaque markers 3005, which may be of gold, are located at the transition between the proximal pinch section 3001 and the distal barrel section 3002. The markers 3005 can give an indication under fluoroscopy of how far to re-advance the microcatheter during the re-sheath process. The radiopaque markers 3005 are preferably offset longitudinally to minimise the profile of the device. Similarly, the radiopaque markers 3004 are also preferably offset longitudinally to minimise device profile.

The distal section 3002, which is similar to those described above, provides a number of advantages. For example, distal section 3002 is the first part of device 3000 to expand and contact the vessel wall as the microcatheter is retracted during device deployment. The distal section 3002 being expanded provides stability to the device 3000 and minimises twisting as the spiral portions of proximal pinch section 3001 is unsheathed in the vessel. This in turn facilitates uniform deployment and expansion of the device 3000 in the obstruction or clot.

Additionally, following deployment of the device 3000 in the clot, the device 3000 is retracted to retrieve the clot through the vasculature to the intermediate catheter, balloon guide catheter or sheath. During retraction, the pinch of a fibrin rich clot may be lost or the clot may contain segments of red blood cell rich 'soft' clot which is not gripped on the proximal pinch section 3001. In these scenarios, the distal barrel section 3002 can provide engagement with the clot and retrieve it through the increased diameter vessels, past the bends and branches to the access catheter or sheath. Further, distal end of distal barrel section 3002 facilitate in pulling a clot into the intermediate catheter, guide catheter or sheath during retrieval. The expanded cells and struts of distal section 3002 engage with the clot at the tip of the catheter during retraction and help pull it into the lumen of the catheter with minimal shear, as its petals go from an expanded configuration in the vessel to a reduced diameter within the catheter.

The device 3000 is preferably formed from a single tube of a shape memory material such as Nitinol which is laser cut to form the strut pattern. The distal barrel section 3002 is flared outwardly to form the barrel shape so that this section forms a larger diameter than that of the proximal pinch section 3001 in the expanded configuration illustrated. The device 3000 also has a proximal joint 3006 between the proximal end of the pinch section 3001 and an elongate shaft on which the device is mounted. The proximal joint is described in detail below.

In the expanded deployed configuration the diameter of the distal barrel section is typically about 4.5 mm (within a range of 3.5 to 8.0 mm) and the diameter of the proximal pinch section is about 2 mm (within a range of 1.5 to 4.0 mm).

Figure 56:
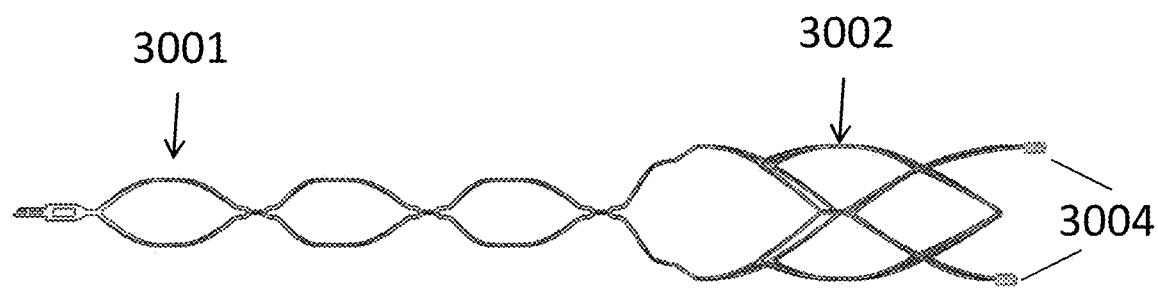
FIGS. 56 and 57 are further views of the device of FIG. 55.
Figure 57:
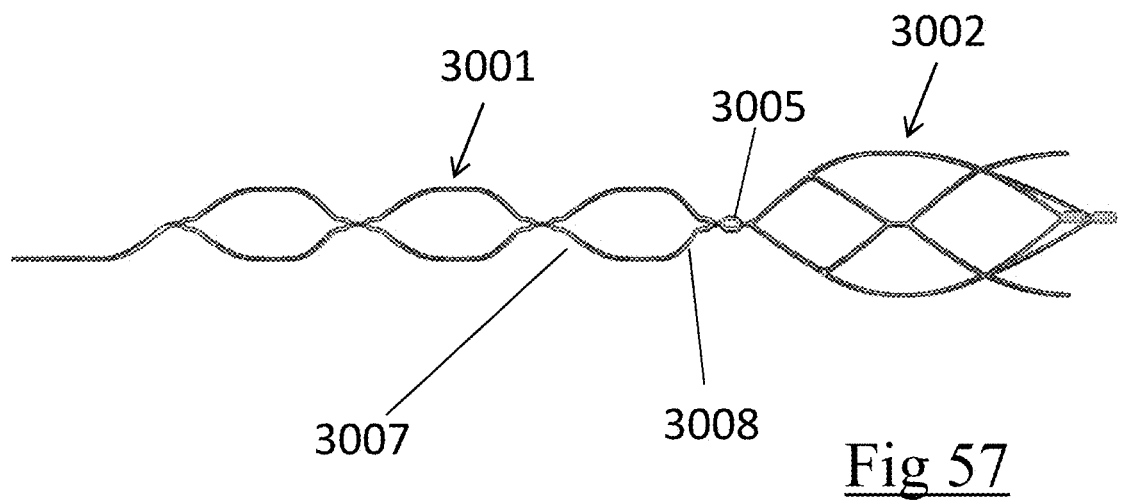
Figure 58:
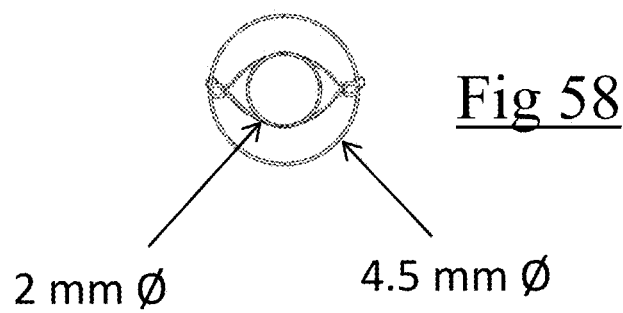
FIG. 58 is an end view of the device in the direction of FIG. 57.

As will be partially apparent from FIGS. 56 and 57 the length of at least some of the proximally facing struts 3007 is larger than the length of at least some of the distally facing struts 3008. The differences in strut length ensure that the radial force applied to a clot by the pinch section varies to achieve good grip on the clot whilst facilitating clot retrieval in association with a microcatheter.

The proximal pinch section 3001 of the device ensures engagement with difficult clots such as fibrin-rich clots whilst the larger distal section 3002 provides improved retention of soft clot, improved clot retrieval into a guide catheter tip and stability of the device on deployment and during retrieval as the device is retracted back through the vasculature and into a guide or sheath.

Figure 59:
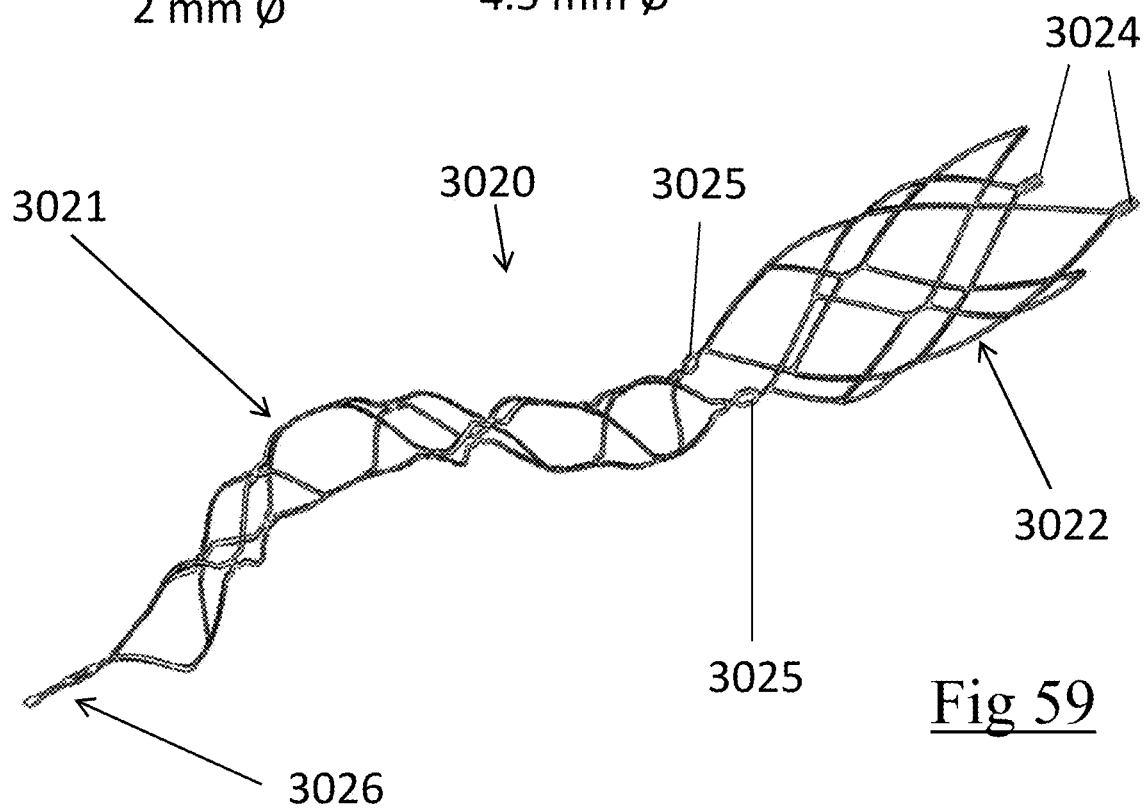
FIG. 59 is an isometric view of a further device according to the invention.

Referring to FIG. 59 there is illustrated another device 3020 according to the invention which is similar to the device of FIGS. 55 to 58 and comprises a proximal pinch section 3021, a distal section 3022, distal marker coils 3024 and radiopaque markers 3025. In this case the proximal pinch section 3021 is heat set into a spiral shape. The spiral may have the following features: spiral pitch-14 mm (within a range of 10-25 mm); spiral outer diameter-5 mm (within a range of 4.0 to 10 mm); and the spiral typically may form a 360° curve, or range from 180 to 720°.

Figure 60:
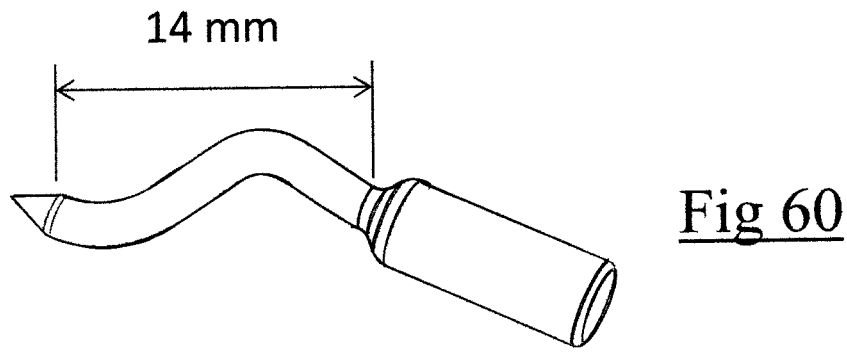
FIGS. 60 to 62 are illustrations of the profile and outer shape of the device of FIG. 59.
Figure 61:
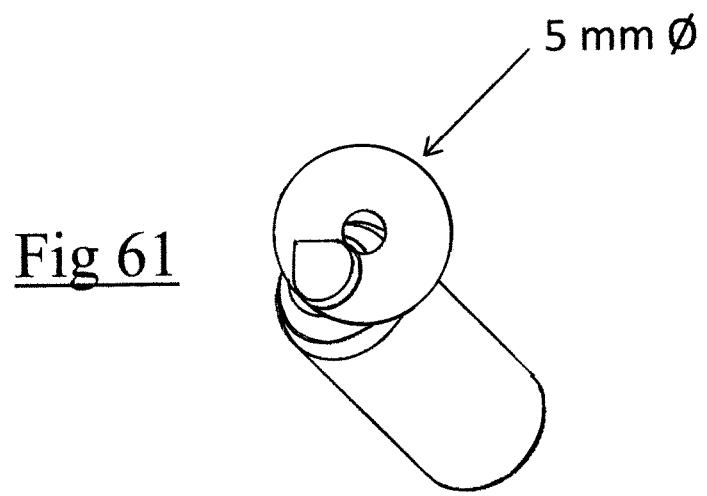
Figure 62:
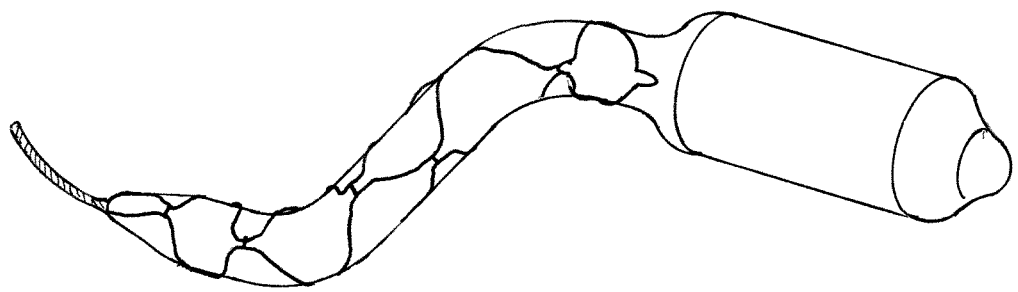

A longitudinal centre axis of the distal barrel section 3022 may be offset from a centre line of the spiral to assist in achieving uniform (low strain) connection between the sections. In this device the distal end of the spiral section is orientated so that it is perpendicular to the proximal face of the barrel section. In this orientation both the struts connecting the spiral section to the barrel section are equal length and have equivalent levels of strain regardless of the cut pattern orientation on the heat forming mandrel. In other iterations the spiral section may be orientated at an angle to the barrel section. The outline shape of the spiral and barrel sections are illustrated in FIGS. 60 to 62. FIG. 62 shows a former tool that may be used to shape the spiral and the flare the tube from which the spiral is made outwardly to form the distal barrel section 3022.

Figure 63:
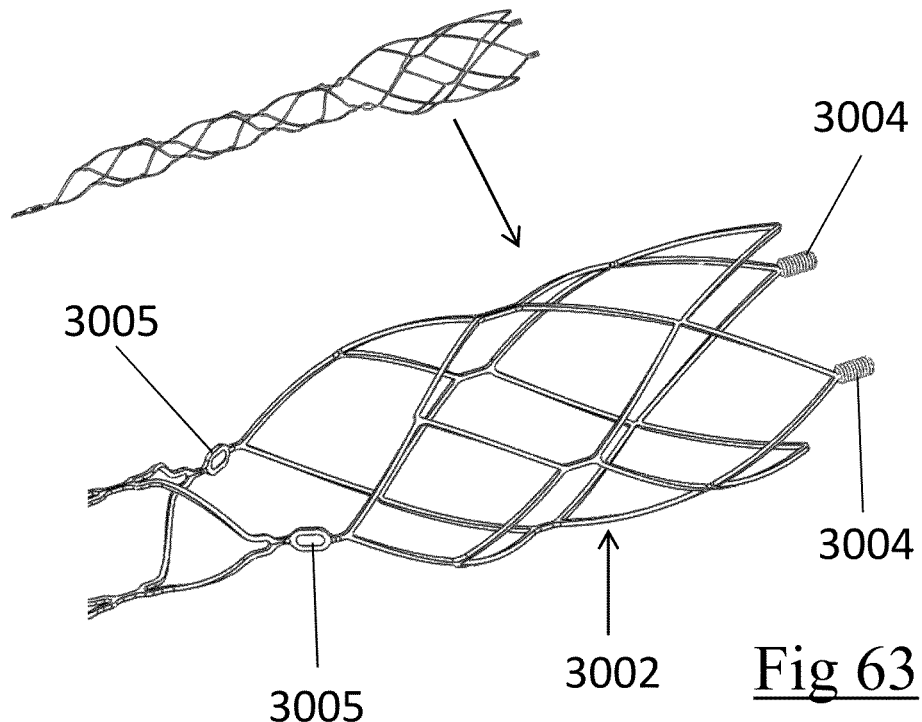
FIG. 63 is an enlarged view of a distal section of the device of FIGS. 55 and 59.
Figure 64:
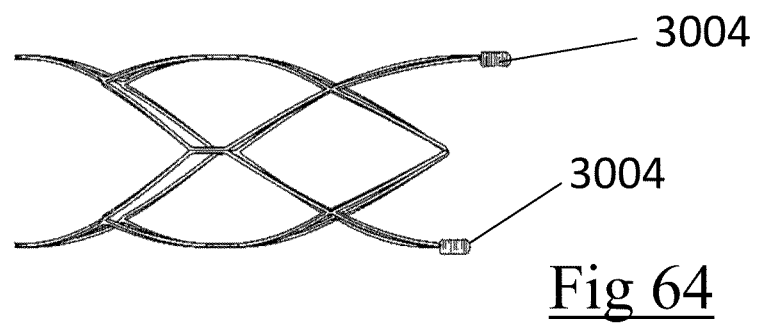
FIG. 64 is a plan view of portion of the distal section of FIG. 63.
Figure 65:
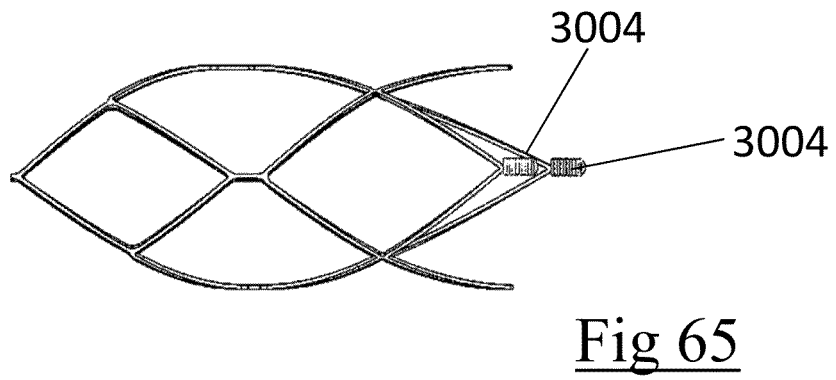
FIG. 65 is a side view of portion of the distal section of FIG. 63.
Figure 66:
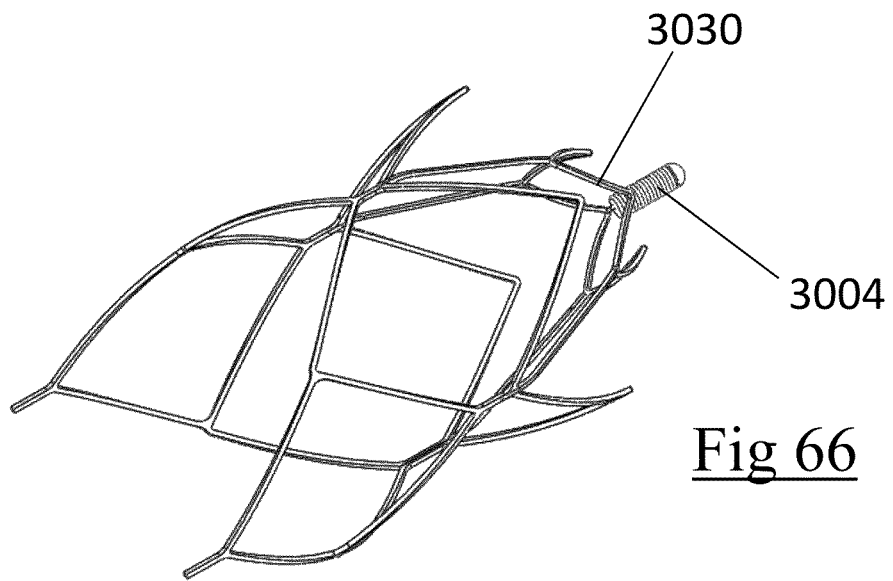
FIG. 66 is an isometric view of portion of a distal section of another device according to the invention.
Figure 67:
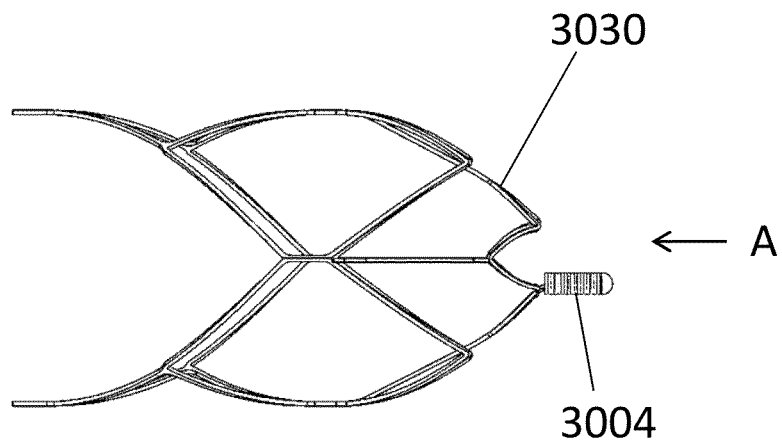
FIG. 67 is a plan view of the distal section of FIG. 66.
Figure 68:
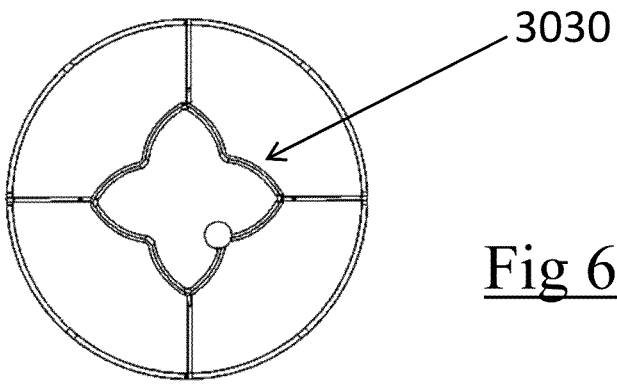
FIG. 68 is an end view in the direction of the arrow A in FIG. 67.
Figure 69:
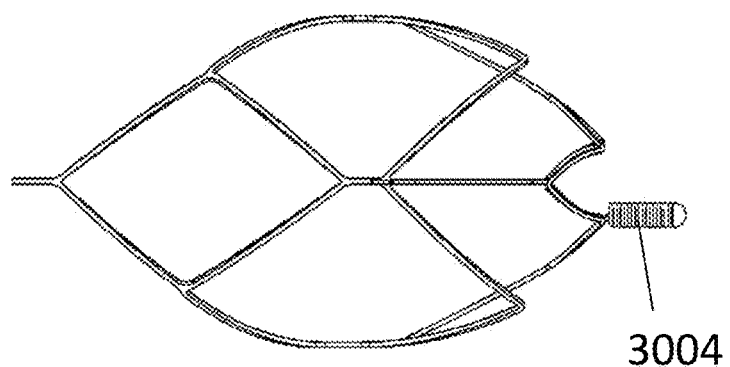
FIG. 69 is a side view of the distal section of FIG. 66.

The barrel section of the devices of FIGS. 55 to 62 is shown in more detail in FIGS. 63 to 65. The staggering of the radiopaque markers 3005, 3025 is particularly apparent in FIG. 63 and the longitudinal staggering of the markers 3004 is clearly apparent in FIG. 64.

FIGS. 66 to 69 illustrate an alternative distal barrel section of devices of the invention. In this case the barrel section has a closed distal end 3030 for fragment protection. Fragment protection may be provided or enhanced by a distal filter which may be mounted on a separate shaft extending through the device.

Figure 70:
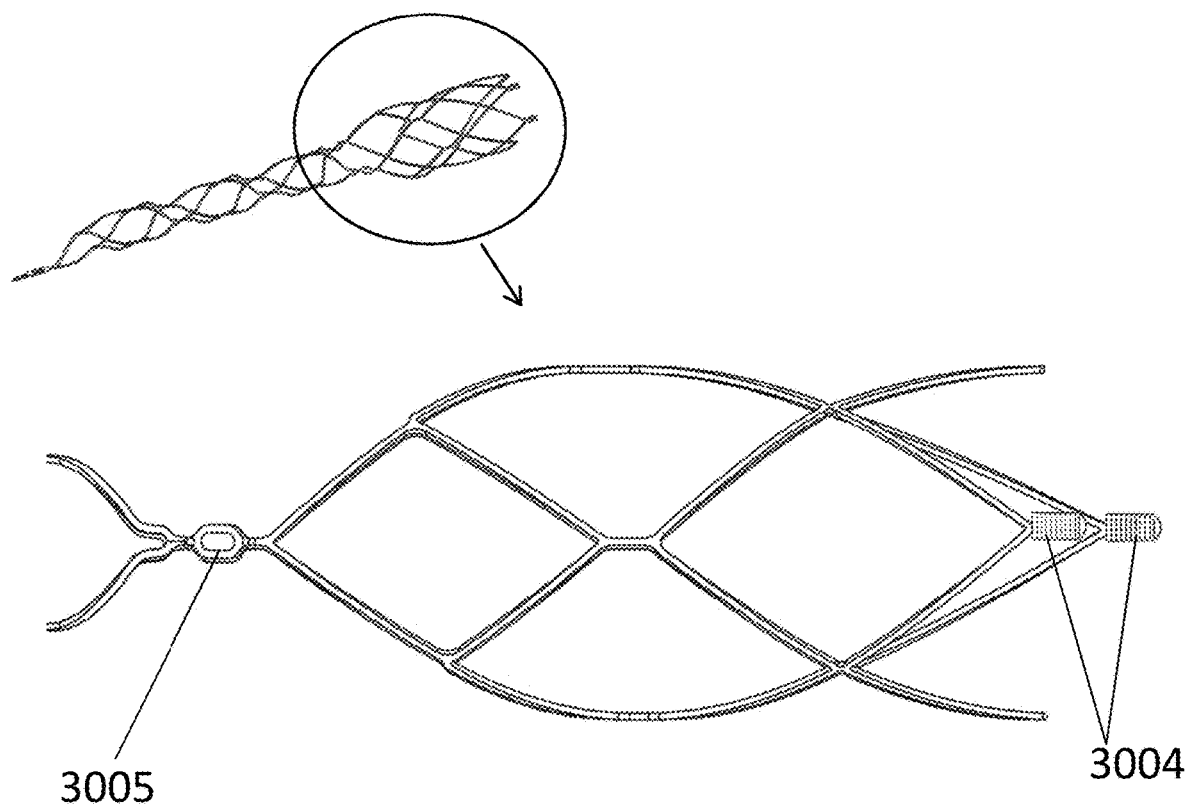
FIG. 70 is an isometric view of a distal portion of a device according to the invention illustrating the location of radiopaque markers.
Figure 71:
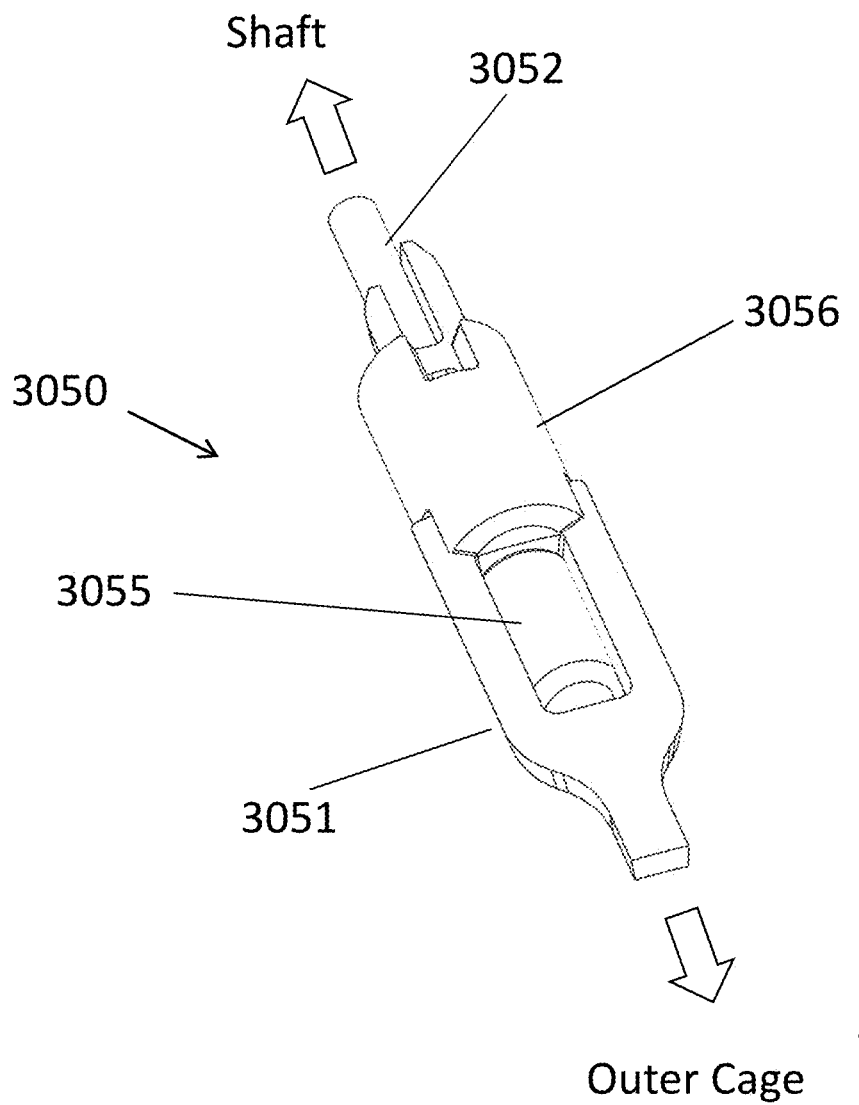
FIG. 71 is an isometric view of a joint between a proximal end of a device of the invention and a shaft.
Figure 72:
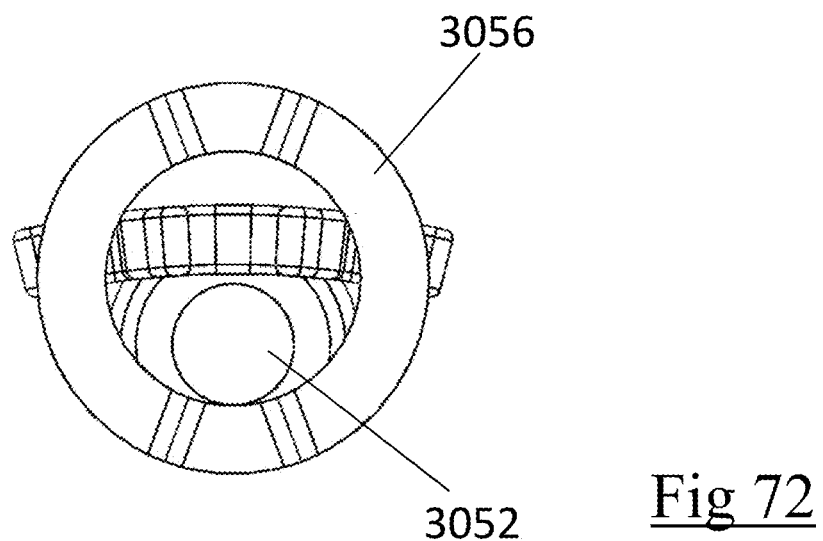
FIG. 72 is an end view of the joint of FIG. 71 illustrating the mechanical lock between a proximal strut and a step on the shaft.
Figure 73:
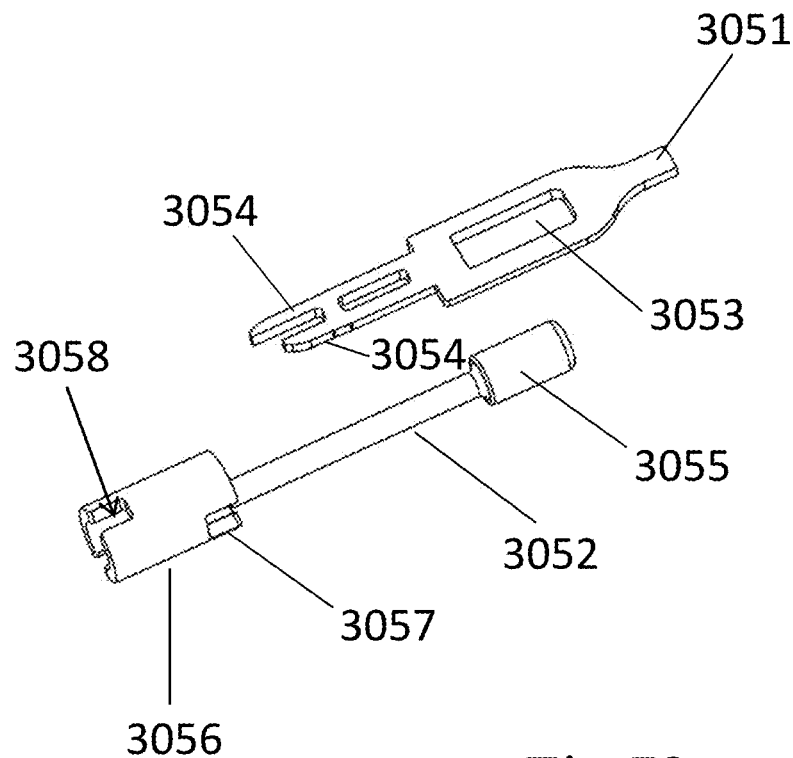
FIGS. 73 to 75 illustrate steps in the mounting of a proximal strut to the step on the shaft.

The configuration and location of the radiopaque markers 3004, 3024, 3005, 3025 are more clearly visible in FIG. 70.

The proximal end of the pinch section of the device of the invention is in some cases attached to a shaft using a mechanical locking system. The locking system may include a first receiver for a shaft and a second receiver for one or more proximal struts of the pinch section. The shaft may include a feature such as a step for engagement with the locking system. In some cases the locking system is configured to accommodate radiopaque markers. In some cases an end of a single strut may be configured for engagement with the locking system. In other cases the locking system is configured to engage with the ends of two or more struts.

Referring to FIGS. 71 to 75 there is illustrated a proximal joint 3050 between a proximal strut 3051 and a shaft 3052. The proximal strut 3051 in this case has a slot 3053 and terminates in two legs 3054, one of which is slightly longer than the other. The increased length of one leg 3054 makes it easier to align and position the collar during assembly of the proximal joint. In another iteration of the design the two legs 3054 are replaced with a single strut (not shown). Additional slots and connecting struts may be included in 3051 to improve the mechanical lock between the component and adhesive applied to the joint.

The shaft 3052 has an enlarged end 3055 which defines a step with the main part of the shaft 3052. A collar 3056 is slidable over the shaft end 3055 and has distally facing slots 3057 to accommodate the body of the strut end in the region of the slot 3053. The collar 3056 also has proximally facing slots 3058, so that the positioning of the collar 3056 on the shaft 3052 is not orientation specific. Part of the enlarged portion 3055 of the shaft 3052 is received in the slot 3053 in the strut 3051. The proximal face of the shaft end 3055 engages with the proximal face of slot 3053 to transmit load during pinching and retraction of the device during use. When the collar 3056 is in position, the slots 3057 constrain the proximal strut 3051 so that the proximal face of slot 3053 cannot disengage from the shaft end 3055. This mechanical lock ensures the ultimate joint strength of the assembly is based on material properties and not on adhesive or weld joint strength, as the joint requires the component materials to fail for the joint to separate.

Figure 74:
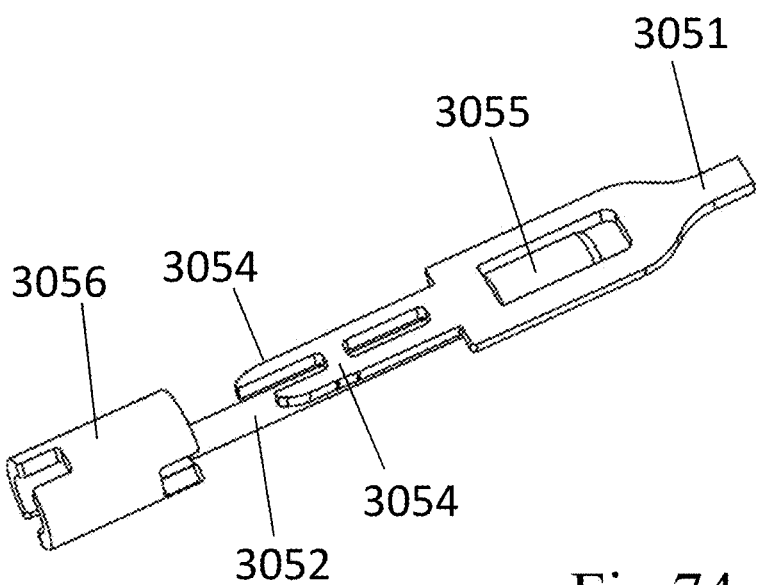
Figure 75:
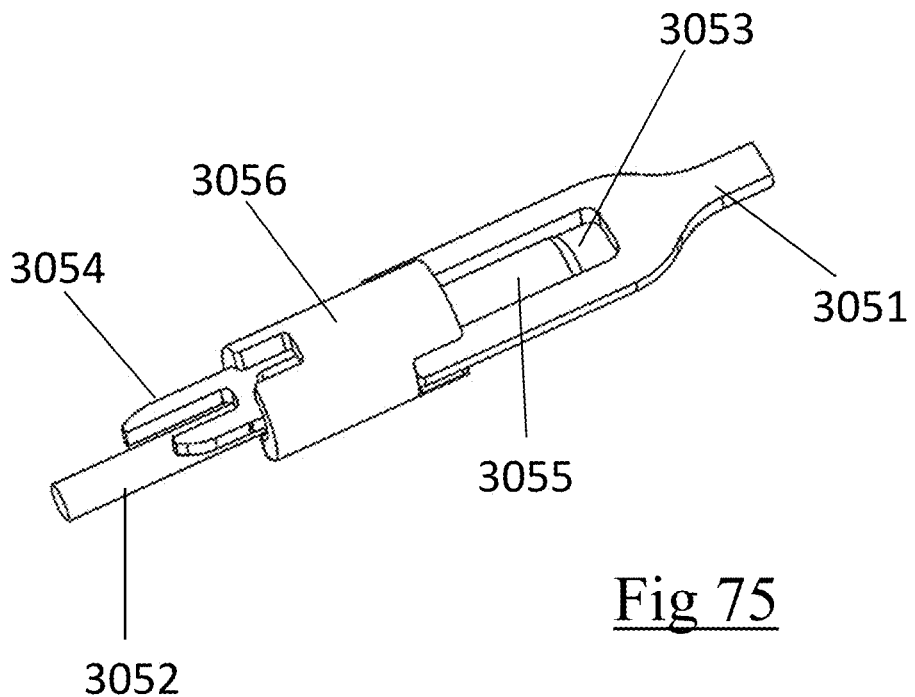
Figure 76:
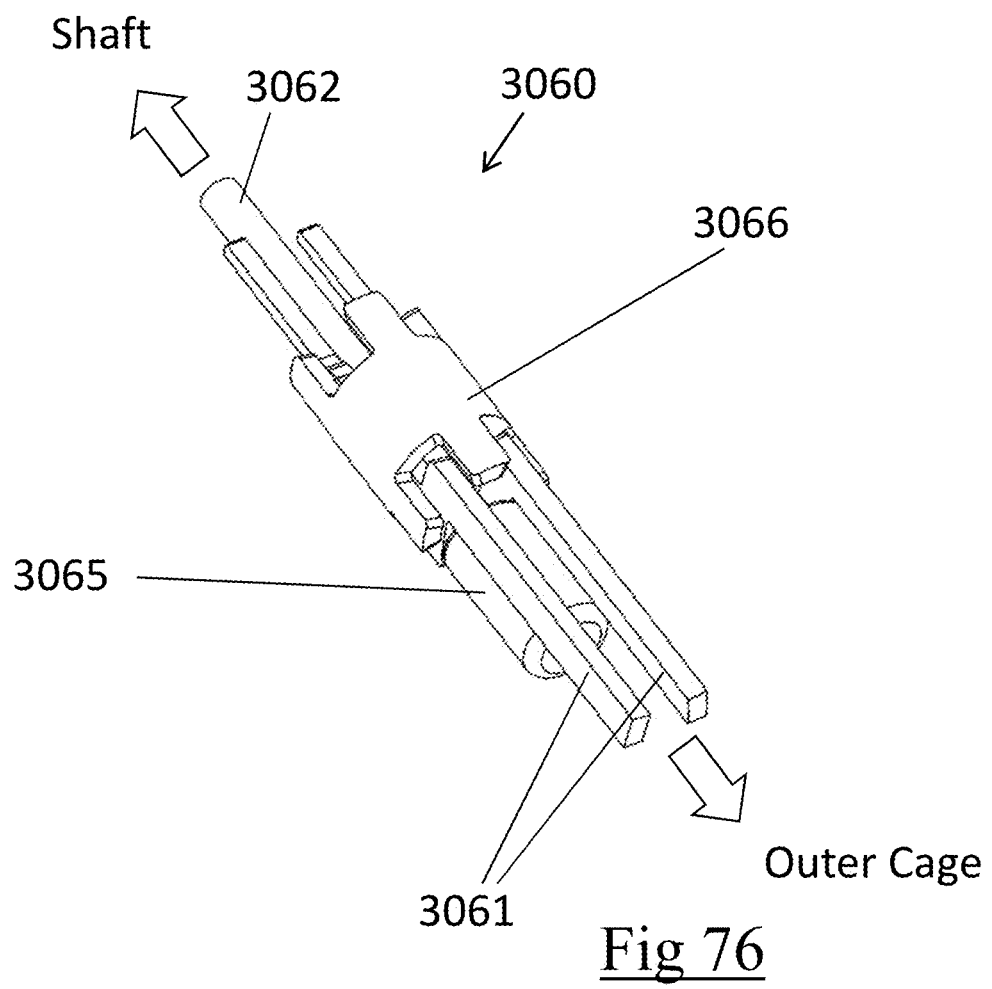
FIG. 76 is an isometric view of another joint between a proximal end of a device of the invention and a shaft.
Figure 77:
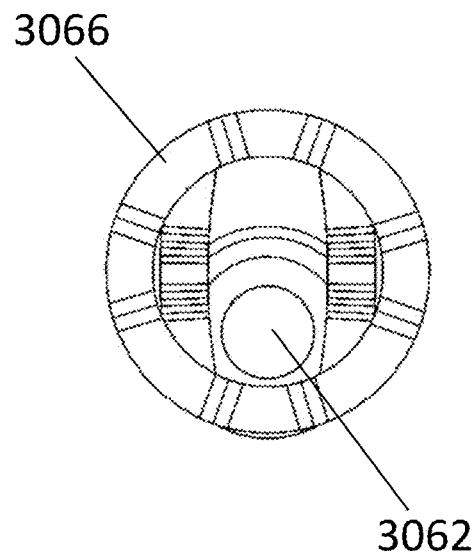
FIG. 77 is an end view of the joint of FIG. 76 illustrating the mechanical lock between proximal struts and a step on the shaft.
Figure 78:
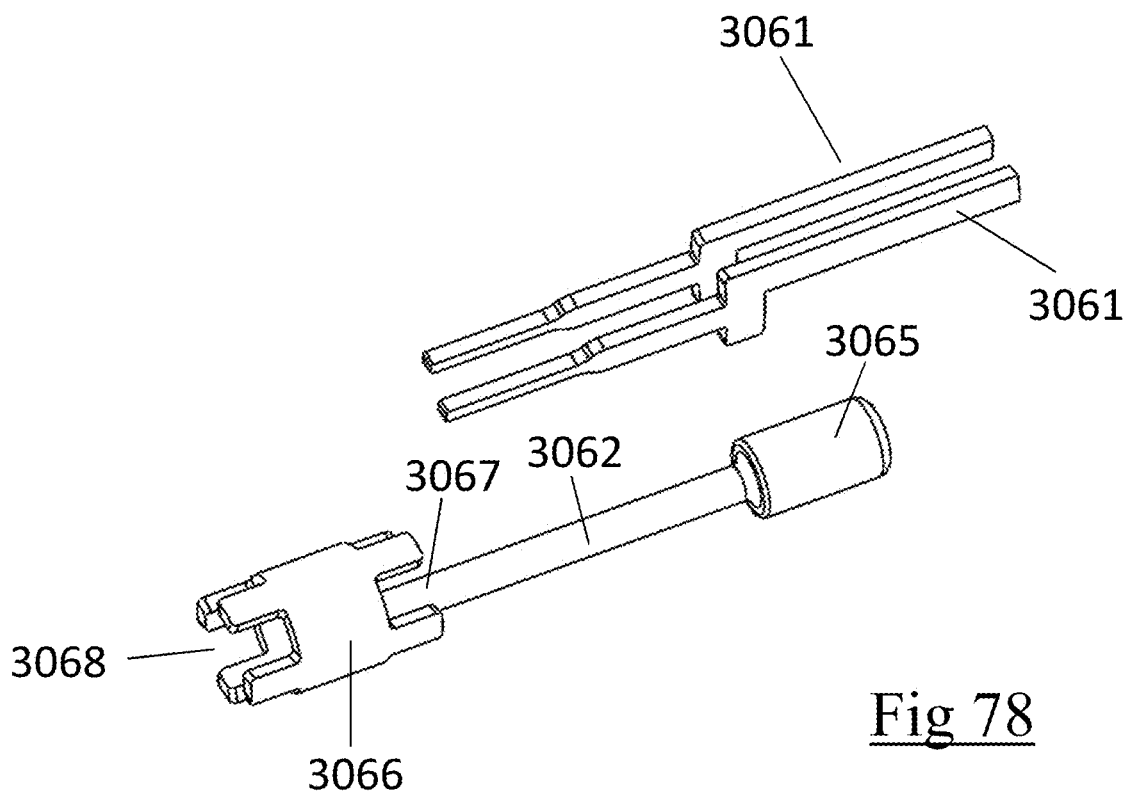
FIGS. 78 to 80 illustrate steps in the mounting of proximal struts to the step on the shaft to form the joint of FIG. 76.
Figure 79:
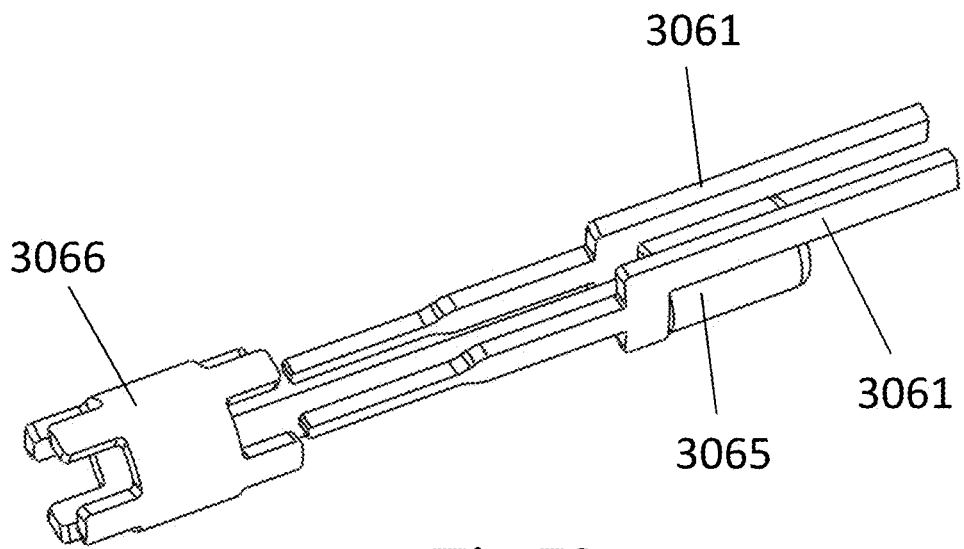
Figure 80:
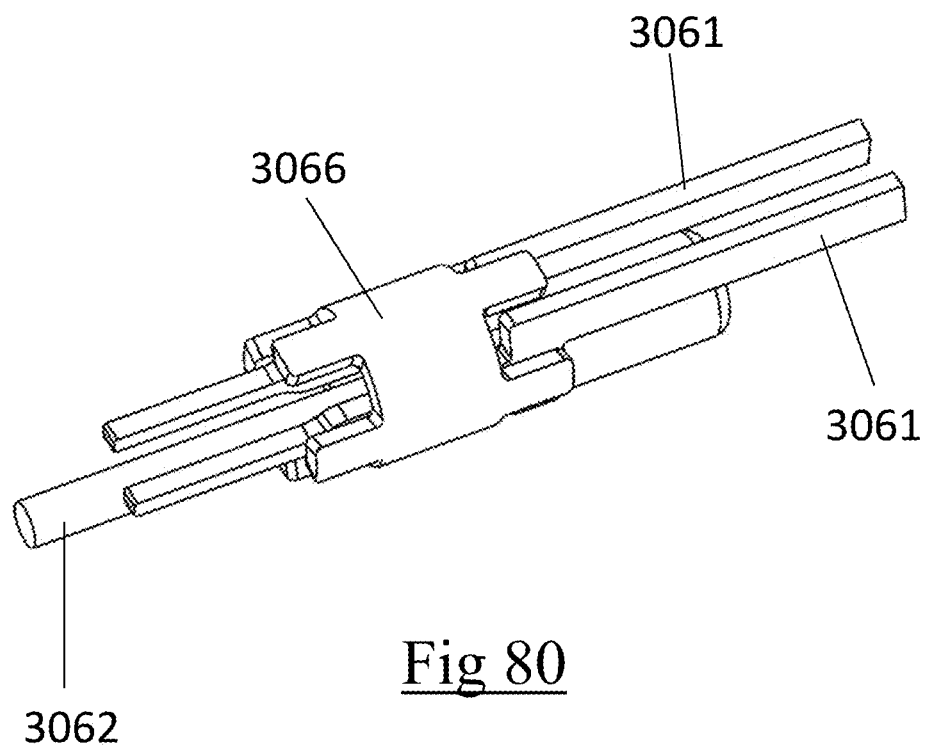

To form the proximal joint, the collar 3056 is first slid over the enlarged portion 3055 of the shaft and advanced along the shaft 3052 to the position illustrated in FIG. 74. The proximal strut 3051 is then positioned so that the enlarged portion 3055 of the shaft is received in the slot 3053 of the strut as illustrated in FIG. 74. The lock collar 3056 is then advanced to lock the strut 3051 to the shaft 3052 as illustrated in FIG. 75. Adhesive is then applied to the joint. A radiopaque marker may then be positioned adjacent to the joint. The configuration ensures that a low profile joint is achieved which has a robust mechanical lock with the tensile strength to facilitate resistant clot retrievals in challenging anatomy. Under compressive loading during delivery of the device through a microcatheter, the distal end of the enlarged portion 3055 may engage with the distal face of slot 3053 providing a face to face transfer of compressive load.

Another proximal joint 3060 is illustrated in FIGS. 76 to 80 which is similar to the proximal joint of FIGS. 71 to 75. In this case the joint 3060 is configured to accommodate the ends 3061 of two proximal struts, which are jointed to a shaft 3062 having an enlarged portion 3065. A lock collar 3066 is used to lock the shaft 3062 to the strut ends 3061. This configuration increases the face to face contact area between the struts of the expanded distal portion 3061 and the proximal face of the enlarged portion of the shaft 3065 improving the ability of the joint to transfer load. The collar 3066 has 4 slots to ensure the struts 3061 cannot disengage from the enlarged portion of the shaft 3065.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

The invention claimed is:

1. A clot removal device for removing a clot from a body vessel, comprising:
an expandable structure comprising a network of interconnected struts configured to engage with the clot and comprising a constrained delivery configuration, an expanded clot engaging deployed configuration, the network of interconnected struts being configured in the expanded clot engaging deployed configuration so at least a portion of the network interpenetrates the clot, the expandable structure comprising:
a distal section comprising an open distal end; and
a non-cylindrical proximal pinch section proximal of the distal section and comprising a diameter less than a diameter of the distal section, the proximal pinch section configured to pinch the clot on movement from the expanded clot engaging deployed configuration to the at least partially constrained clot pinching configuration,
the proximal pinch section being further configured such that when the network of interconnected struts is collapsed while in a state of interpenetration with the clot that at least a portion of the proximal pinch section pinches at least a portion of the clot; and an elongate member comprising a proximal end and a distal end connected to the proximal pinch section; and
at least a first cell and at least one second cell formed by the network of interconnected struts, each comprising a collapsed delivery configuration;
a clot engaging element configured to exert an outward radial force when deployed within the blood vessel having an inner diameter which is lower than that of the expanded deployed configuration,
the clot engaging element being configured to exert an outward radial force varying in a generally sinusoidal pattern along a length of the clot engaging element; and
a deployed expanded configuration with each cell further comprising an orifice, the orifice of at least some of the cells being configured to allow at least a portion of the clot body to interpenetrate the structure,
the expandable structure being configured to interpenetrate the clot defined by an extrusion of at least a portion of the clot through at least one of the first cells.

2. The device of claim 1, the distal section further comprising a distal barrel section flared outwardly to form a barrel shape with the open distal end, and
wherein the network of interconnected struts comprises at least a plurality of proximally facing struts and a plurality of distally facing struts,
a length of at least some of the proximally facing struts being larger than a length of at least some of the distally facing struts thereby varying an outward radial force of the device in the expanded clot engaging deployed configuration.

3. The device of claim 2, wherein the distal barrel section comprises distal radiopaque markers attached to distal most ends of at least two of the interconnected struts that form the distal barrel section.

4. The device of claim 2, further comprising:
a plurality of radiopaque markers positioned at a transition between the proximal pinch section and the distal barrel section.

5. The device of claim 1, wherein the proximal pinch section comprises a spiral form comprising a spiral pitch ranging between approximately 10-25 mm.

6. The device of claim 1, further comprising: a longitudinal axis extended through the distal section, the proximal pinch section extending around the longitudinal axis in a spiral.

7. The device of claim 1, wherein the elongate member is configured to retract the network with the network both interpenetrating the clot and at least a portion of the network pinching on at least a portion of the clot.

8. The device of claim 1, wherein the network of interconnected struts extends between crowns and are configured to pinch clot located in at least one of the first cells as the device is moved from the expanded deployed configuration to the at least partially constrained clot pinching configuration, wherein each of the cells has a proximally facing crown and a distally facing crown and wherein the proximally facing crown has a diameter which is larger than a diameter of the distally facing crown.

9. The device of claim 1, wherein the generally sinusoidal pattern comprises a wave pattern comprising an amplitude that decreases along a length of the clot engaging element, the amplitude being higher at a proximal end and lower at a distal end of the clot engaging element.

10. The device of claim 9, the clot engaging element further comprising a plurality of adjacent segments configured such that the outward radial force exerted by at least two adjacent segments differs from each other.

11. The device of claim 1, wherein at least some of the struts and/or crowns of the expandable structure are aligned with the generally sinusoidal pattern to enhance embedding of the clot.

12. The device of claim 1, wherein a size of a clot-receiving cell towards a proximal end of the expandable structure is smaller than a cell towards a distal end of the expandable structure.

13. The device of claim 1 further comprising a proximal joint between the elongate member and the expandable structure, the proximal joint comprising a step at the distal end of the elongate member.

14. The device of claim 13, wherein the proximal joint comprises a locking collar for engagement with the elongate member and the proximal end of the expandable structure.

15. The device of claim 1, wherein the distal end of the expandable structure comprises a recess configured for engagement with a step at the distal end of the elongate member.

16. The device of claim 1, wherein the distal end of the expandable structure comprises a slot configured for engagement with a step at the distal end of the elongate member.

17. A clot removal device for removing a clot from a body vessel, comprising:
an expandable structure comprising a network of interconnected struts configured to engage with the clot and comprising a constrained delivery configuration, an expanded clot engaging deployed configuration, the network of interconnected struts being configured in the expanded clot engaging deployed configuration so at least a portion of the network interpenetrates the clot, the expandable structure comprising:
a distal section comprising an open distal end; and
a non-cylindrical proximal pinch section proximal of the distal section and comprising a diameter less than a diameter of the distal section, the proximal pinch section configured to pinch the clot on movement from the expanded clot engaging deployed configuration to the at least partially constrained clot pinching configuration,
the proximal pinch section being further configured such that when the network of interconnected struts is collapsed while in a state of interpenetration with the clot that at least a portion of the proximal pinch section pinches at least a portion of the clot; and an elongate member comprising a proximal end and a distal end connected to the proximal pinch section; and
at least a first cell and at least one second cell formed by the network of interconnected struts, each comprising a collapsed delivery configuration;
a clot engaging element configured to exert an outward radial force when deployed within the blood vessel having an inner diameter which is lower than that of the expanded deployed configuration,
the clot engaging element being configured to exert an outward radial force varying in a generally sinusoidal pattern along a length of the clot engaging element; and
a deployed expanded configuration with each cell further comprising an orifice, the orifice of at least some of the cells being configured to allow at least a portion of the clot body to interpenetrate the structure,
the expandable structure being configured to interpenetrate the clot defined by an extrusion of at least a portion of the clot through at least one of the first cells,
wherein the generally sinusoidal pattern comprises a wave pattern comprising an amplitude that decreases along a length of the clot engaging element, the amplitude being higher at a proximal end and lower at a distal end of the clot engaging element.

18. A clot removal device for removing a clot from a body vessel, comprising:
an expandable structure comprising a network of interconnected struts configured to engage with the clot and comprising a constrained delivery configuration, an expanded clot engaging deployed configuration, the network of interconnected struts being configured in the expanded clot engaging deployed configuration so at least a portion of the network interpenetrates the clot, the expandable structure comprising:
a distal section comprising an open distal end; and
a non-cylindrical proximal pinch section proximal of the distal section and comprising a diameter less than a diameter of the distal section, the proximal pinch section configured to pinch the clot on movement from the expanded clot engaging deployed configuration to the at least partially constrained clot pinching configuration,
the proximal pinch section being further configured such that when the network of interconnected struts is collapsed while in a state of interpenetration with the clot that at least a portion of the proximal pinch section pinches at least a portion of the clot; and an elongate member comprising a proximal end and a distal end connected to the proximal pinch section; and
at least a first cell and at least one second cell formed by the network of interconnected struts, each comprising a collapsed delivery configuration;
a clot engaging element configured to exert an outward radial force when deployed within the blood vessel having an inner diameter which is lower than that of the expanded deployed configuration,
the clot engaging element being configured to exert an outward radial force varying in a generally sinusoidal pattern along a length of the clot engaging element; and
a deployed expanded configuration with each cell further comprising an orifice, the orifice of at least some of the cells being configured to allow at least a portion of the clot body to interpenetrate the structure,
the expandable structure being configured to interpenetrate the clot defined by an extrusion of at least a portion of the clot through at least one of the first cells, wherein at least some of the struts and/or crowns of the expandable structure are aligned with the generally sinusoidal pattern to enhance embedding of the clot.

\* \* \* \* \*